United States Patent
Zimmer et al.

(10) Patent No.: US 9,487,559 B2
(45) Date of Patent: Nov. 8, 2016

(54) COMPOSITIONS COMPRISING MULTIVALENT SYNTHETIC LIGANDS OF SURFACE NUCLEOLIN AND GLYCOSAMINOGLYCANS

(75) Inventors: Robert Zimmer, Mulhouse (FR); José Courty, Villecresnes (FR)

(73) Assignees: ELRO PHARMA SARL, Mulhouse (FR); CENTRE NATIONAL DE LA RECHERCHE SCIENTIFIQUE (CNRS), Paris (FR); UNIVERSITE PARIS 12—VAL DE MARNE, Creteil (FR)

( * ) Notice: Subject to any disclaimer, the term of this patent is extended or adjusted under 35 U.S.C. 154(b) by 0 days.

(21) Appl. No.: 13/877,490

(22) PCT Filed: Oct. 4, 2011

(86) PCT No.: PCT/EP2011/067337
§ 371 (c)(1),
(2), (4) Date: Jun. 18, 2013

(87) PCT Pub. No.: WO2012/045750
PCT Pub. Date: Apr. 12, 2012

(65) Prior Publication Data
US 2014/0080759 A1    Mar. 20, 2014

Related U.S. Application Data

(60) Provisional application No. 61/389,519, filed on Oct. 4, 2010.

(51) Int. Cl.
| | |
|---|---|
| *A61K 31/7068* | (2006.01) |
| *C07K 7/08* | (2006.01) |
| *A61K 31/726* | (2006.01) |
| *A61K 36/00* | (2006.01) |
| *A61K 36/02* | (2006.01) |
| *A61K 36/10* | (2006.01) |
| *A61K 38/06* | (2006.01) |
| *A61K 31/727* | (2006.01) |
| *A61K 38/16* | (2006.01) |

(52) U.S. Cl.
CPC ............ *C07K 7/08* (2013.01); *A61K 31/7068* (2013.01); *A61K 31/726* (2013.01); *A61K 31/727* (2013.01); *A61K 36/00* (2013.01); *A61K 36/02* (2013.01); *A61K 36/10* (2013.01); *A61K 38/06* (2013.01); *A61K 38/16* (2013.01)

(58) Field of Classification Search
None
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,340,535 A | 7/1982 | Voisin et al. |
| 4,366,241 A | 12/1982 | Tom et al. |
| 4,472,509 A | 9/1984 | Gansow et al. |
| 5,021,236 A | 6/1991 | Gries et al. |
| 5,891,737 A | 4/1999 | Baindur et al. |
| 6,235,716 B1 | 5/2001 | Ben-Sasson |
| 6,783,952 B1 | 8/2004 | Brown et al. |
| 7,741,280 B2 | 6/2010 | Guichard et al. |
| 8,497,349 B2 | 7/2013 | Courty et al. |
| 2004/0002457 A1 | 1/2004 | Hovanessian et al. |
| 2004/0047867 A1 | 3/2004 | Capron et al. |
| 2004/0186056 A1 | 9/2004 | Ruoslahti et al. |
| 2004/0248195 A1 | 12/2004 | Myllykallio et al. |
| 2005/0026860 A1 | 2/2005 | Lin et al. |
| 2008/0234464 A1 | 9/2008 | Ikeda et al. |
| 2011/0065649 A1 | 3/2011 | Courty et al. |
| 2011/0201559 A1 | 8/2011 | Briand et al. |
| 2014/0073555 A1 | 3/2014 | Courty et al. |

FOREIGN PATENT DOCUMENTS

| | | |
|---|---|---|
| EP | 2033655 | 3/2009 |
| WO | WO 95/29190 | 11/1995 |
| WO | WO 00/61597 | 10/2000 |
| WO | WO 2003/102207 | 12/2003 |
| WO | WO 2005/035579 | 4/2005 |
| WO | WO 2007/125210 | 4/2007 |
| WO | WO 2007/125210 | 11/2007 |
| WO | WO 2009/141687 | 11/2009 |
| WO | WO 2012/045750 | 4/2012 |

OTHER PUBLICATIONS

Abbondanzo et al., 1990.
Aldrian-Herrada et al., Nucleic Acids Res., vol. 26, p. 4910-4916, 1998.
Alete et al., Febs J., vol. 273, p. 4668-81, 2006.
Allred et al., 1990.
Alter, P. et al., Usefulness of cytokines interleukin-6 and interleukin-2R concentrations in diagnosing active infective endocarditis involving native valves, Am. J. Cardiol., vol. 89, p. 1400-1404, 2002.
Atherton, E. et al., Solid Phase peptide synthesis: a practical approach, Oxford, England, IRL Press, 1989.
Axen et al., Nature, vol. 214, p. 1302, 1987.
Bast, R. C. et al., New England, J. Med., vol. 309, p. 883-887, 1983.
Bates, P. et al., Antiproliferative activity of G-rich oligonucleotides correlates with protein binding, J. Biol. Chem., vol. 274, No. 37, p. 26369-26377, 1999.

(Continued)

*Primary Examiner* — Thomas S Heard
(74) *Attorney, Agent, or Firm* — Bryan D. Zerhusen; Locke Lord LLP

(57) ABSTRACT

The present invention relates to a composition comprising a Nucant multivalent synthetic compound and a glycosaminoglycan, the admixture of both compounds forming microspheres comprising both compounds, as well as their use for the treatment or prevention of diseases associated with deregulation of proliferation and/or angiogenesis, such as cancer, inflammatory disease, or for promoting wound healing.

17 Claims, 17 Drawing Sheets

(56) References Cited

OTHER PUBLICATIONS

Bates, P. J. et al., Discovery and development of the G-rich oligonucleotide AS1411 as a novel treatment for cancer, Exp. Mol. Pathol., 86(3), p. 151-164, 2009.
Bella, D. H. et al., Proc. Natl. Acad. Sci., USA, vol. 81, p. 3869-3873, 1984.
Blondet, B. et al., Exogeneous pleiotrophin applied to lesioned nerve impairs muscle reinnervation, Neurochem. Res., 31(7), p. 907-913, 2006.
Boado et al., J. Pharm. Sci., vol. 87, p. 1308-1315, 1998.
Boado, Adv. Drug Delivery Rev., vol. 15, p. 73-107, 1995.
Bucklin, S. E., An interleukin-6-induced acute-phase response does not confer protection against lipopolysaccharide lethality, Infect. Immun., vol. 61, No. 8, p. 3184-3189, 1993.
Callebaut, C. et al., Identification of V3 loop-binding proteins as potential receptors implicated in the binding of HIV particles to CD4(+) cells, J. Biol. Chem., vol. 273, No. 34, p. 21988-21997, 1998.
Callebaut, C. et al., Pseudopeptide TASP inhibitors of HIV entry bind specifically to a 95-kDa cell surface protein, J. Biol. Chem., vol. 272, No. 11, p. 7159-7166, 1997.
Callebaut, 1996, Virology, 218 pp. 181-192.
Capone, P. M. et al., Proc. Natl. Acad. Sci, USA, vol. 80, p. 7328, 1983.
Carpino, L. A., 1-Hydroxy-7-azabenzotriazole. An efficient peptide coupling additive, J. Am. Chem. Soc., 115(10), p. 4397-4398, 1993.
Carrasquillo,J. A. et al., Cancer Treat. Rep., vol. 68, p. 317, 1984.
Chan, H. J. et al., Nucleophosmin/B23-binding peptide inhibits tumor growth and up-regulates transcriptional activity of p53, Biochem. Biophys. Res. Commun., 333(2), p. 396-403, 2005.
Chiou, R. et al., Cancer REs., vol. 45, p. 6140-6146, 1985.
Christian, S. et al., Nucleolin expressed at the cell surface is a marker of endothelial cells in angiogenic blood vessels, J. Cell Biol., vol. 163, No. 4, p. 871-878, 2003.
Courtenay-Luck, N. et al., Lancet, vol. 1, p. 1441, 1984.
Cushman, Cushman, et al., Development of Methodology for the Synthesis of Stereochemically Pure Phe4i[CH2N]Pro Linkages in HIV Protease Inhibitors, J Org. Chem. 56, pp. 4161-4167, 1991.
Deguchi, T. et al., Cancer Res., vol. 46, p. 3751, 1986.
Deguchi, T. et al., Fed. Proc., vol. 44, p. 1684, 1985.
Destouches et al., A Simple Approach to Cancer Therapy Afforded by Multivalent Pseudopeptides that Target Cell-Surface Nucleoproteins, Cancer Res 2011;71:3296-3305.
Destouches, D. et al., Suppression of tumor growth and angiogenesis by a specific antagonist of the cell-surface expressed nucleolin, PLoS One, 3(6), p. 2518, 2008.
Dhanabal, M. et al., Endostatin induces endothelial cell apoptosis, J. Biol. Chem., 274(17), p. 11721-11726, 1999.
Di Segni, A. et al., Identification o fnucleolin as new ErbB receptor interacting protein, PLoS One, 3(6), p. 2310, 2008.
Drecoll, E. et al., Treatment of peritoneal carcinomatosis by targeted delivery of the radio-labeled tumor homing peptide bi-DTPA-[F3]2 into the nucleus of tumor cells, PloS One, 4(5), p. 5715, 2009.
Dumler, I. et al., urokinase-induced mitogenesis is mediated by casein kinase 2 and nucleolin, Curr. Bio., 9(24), p. 1468-1476, 1999.
El Khoury et al., Targeting Surface Nucleolin with A Multivalent Pseudopeptide Delays Development of Spontaneous Melanoma in RET Transgenic Mice, BMC Cancer 2010, 10:325, pp. 1-12.
Elass, E. et al., Lactoferrin inhibits the lipposaccharaide-induced expression and proteoglycan-binding ability of IL-8 in human entothelial cells, Infect. Immun., vol. 70, No. 4, p. 1860-1866, 2002.
Embleton, M. J. et al., Br. J. Cancer, vol. 49, p. 559, 1984.
Emerich, D. F. et al., Cell Transplant, vol. 8, p. 47-59, 1999.
Engleton et al., Peptides, vol. 9, p. 1431-1439, 1997.
Epenetos, A. A. et al., Cancer, vol. 55, p. 984-987, 1985.
Ettinger, D. S. et al., Cancer Treat. Rep., vol. 66, p. 289-297, 1982.
Fazekas, 2001, Microvascular Research, 62 pp. 440-444.
Feuerstein, N. et al., Identificaiotn of numatrin, the nuclear matrix protein associated with induction of mitogenesis, as the nucleolar protein B23. Implication for the role of the nucleolus in early transduction of mitogenic signals, J. Biol. Chem., 263(22), p. 10608-10612, 1988.
Fogal, V. et al., Cell surface nucleolin antagonist causes endothelial cell apoptosis and normalization of tumor vasculature, Angiogenesis, 12(1), p. 91-100, 2009.
Fournel, S. et al., C3-symmetric peptide scaffolds are functional mimetics of trimeric CD4OL, Nat. Chem. Biol., vol. 1, No. 7, p. 377-382, 2005.
Ginsty, H. et al., Structure and functions of nucleolin, J. Cell Science, vol. 112, p. 761-772, 1999.
Goldenberg, D. M. et al., Cancer Res., vol. 41, p. 4353, 1981.
Goldenberg, D. M. et al., Gastroenterol., vol. 84, p. 524-532, 1983.
Goldenberg, D. M. et al., J. A. M. A., vol. 250, p. 630-635, 1983.
Goldenberg, D. M. et al., New England J. Med., vol. 298, p. 1384-1388, 1978.
Gregoriadis, Liposome Technology, vols. I-III, $2^{IId}$ ed, CRC Press, Boca Raton, Florida, 1993.
Grinstein, E. et al., Cell cycle-controlled interaction of nucleolin with the retinoblastoma protein and cancerous cell transformation, J. Biol. Chem., 281(31), p. 22223-22235, 2006.
Harms, G. et al., Identification of nucleolin as a new L-selectin ligand, Biochem. J., 360(Pt 3), p. 531-538, 2001.
Hayes, D. F. et al., J. Clin. Invest., vol. 75, p. 1671, 1985.
Hedin, A. et al., Proc. Natl. Acad. Sci., USA, vol. 80, p. 3470, 1983.
Herlyn, D. et al., proc. Natl. Acad. Sci., USA, vol. 79, p. 4761, 1982.
Herlyn, M. et al., J. Clin. Immunol., vol. 2, p. 135, 1982.
Houghton, A. N. et al., Proc. Natl. Acad. Sci., USA, vol. 82, p. 1242, 1985.
Hovanessian et al., The cell-surface-expressed nucleolin is associated with the actin cytoskeleton, Exp. Cell Res., vol. 261, p. 312-328, 2000.
Hovanessian, et al., Surface Expressed Nucleolin is Constantly Induced in Tumor Cells to Mediate Calcium-Dependent Ligand Internalization, PLoS One Dec. 2010, 5(12) : pp. 1-13.
Hruby et al., Conformational and Topographical Considerations in Designing Agonist Peptidomimetics from Peptide Leads, Current Medicinal Chemistry, 2000, 7, pp. 945-970.
Huang, Y. et al., The angiogenesis function of nucleolin is mediated by vascular endothelial growth factor and nonmuscle myosin, Blood, vol. 107, No. 9, p. 3564-3571, 2006.
Hurwitz, H. I., New agents in colon cancer, Clin. Adv. Hematol. Oncol., vol. 1, No. 7, p. 404405, 2003.
Hwang, K. M. et al., J. Natl. Cancer Inst., vol. 76, p. 849-855, 1986.
Inder, K. L. et al., Nucleophosmin and nucleolin regulate K-Ras plasma membrane interactions and MAPK signal transduction, J. Biol. Chem., 284(41), p. 28410-28933, 2009.
Ishiwata et al., Chem. Pharm. Bull., vol. 43, p. 1005-1011, 1995.
Jolliet-Riant, et al., Fundam. Clin. Pharmacol., vol. 13, p. 16-26, 1999.
Jones, D. H. et al., Int. J. Cancer, vol. 35, p. 715, 1985.
Kabbinavar, F. et al., Phase II, randomized trial comparing bevacizumab plus fluorouracil (FU)/leucovorin (LV) with FU/LV alone in patients with metastatic colorectal cancer, J. Clin. Oncol., vol. 21, No. 1, p. 60-65, 2003.
Kaltovich, F. A. et al., J. Nucl. Med., vol. 27, p. 897, 1986.
Kannan, K. et al., Animal models of rheumatoid arthritis and their revalence to human disease, Pathophysiology, vol. 12, p. 167-181, 2005.
Kaprowski, H. et al., Proc. Natl. Acad. Sci., USA, vol. 81, p. 216, 1984.
Karima, R. et al., The molecular pathogenesis of endotoxic shock and organ failure, Mol. Med. Today, p. 123-132, 1999.
Kevil, C. G. et al., Essential role of ICAM-1 in mediating monocyte adhesion to aortic endothelial cells, Am. J. Physiol. Cell Physiol., vol. 281, p. 1442-1447, 2001.
Killian, C. S. et al., Cancer Res., vol. 45, p. 886, 1985.
Killian, C. S. et al., J. Natl. Cancer Inst., vol. 76, p. 179, 1986.
Klug, T. L. et al., Cancer Res., vol. 44, p. 1048, 1984.
Kreuter et al., Brain Res., vol. 674, p. 171-174, 1995.
Krust et al., Suppression of Tumorigenicity of Rhabdoid Tumor Derived G401 Cells by the Multivalent HB-19 Pseudopeptide that Targetrs Surface Nucleolin, Biochimie. Mar. 2011;93(3):426-433.

(56) References Cited

OTHER PUBLICATIONS

Krust et al., Targeting Surface Nucleolin with Multivalent HB-19 and Related Nucant Pseudopeptides Results in Distinct Inhibitory Mechanisms Depending on the Malignant Tumor Cell Type, BMC Cancer 2011, 11:333, pp. 1-22.
Krust et al., The anti-HIV pentameric pseudopeptide HB-19 is preferentially taken up in vivo by lymphoid organs where it forms a comples with nucleolin, PNAS, vol. 98, No. 24, p. 1409014095, Nov. 20, 2001.
Lange, P. H. et al., Surgery, vol. 98, p. 143, 1985.
Larrucea, S. et al., Cellular adhesion mediated by factor J, a complement inhibitor. Evidence for nucleolin involvement, J. Biol. Chem., 273(48), p. 31718-31725, 1998.
Lasic et al., Chem. Rev., vol. 95, p. 2601-2627, 1995.
Legrand, D. et al., Surface nucleolin participates in both the binding and endocytosis of lactoferrin in target cells, Eur. J. Biochem., vol. 271, p. 303-317, 2004.
Ling, Y. et al., Endostar induces apoptotic effects in HUVECs through activation of caspase-3 and decrease of Bc1-2, Anticancer Res., 29(1), p. 411-417, 2009.
Liu, M.A. et al., Proc. Natl. Acad. Sci., USA, vol. 82, p. 8648-8652, 1985.
Majno, G. et al., Apoptosis, oncosis, and decrosis. An overview of cell Death, Am. J. Pathol., 146(1), p. 3-15, 1995.
Merrifield, R. B., Solid Phase Peptide Synthesis. I. The Synthesis of a Tetrapeptide, J. Am. Chem. Soc., 85(14), p. 2149-2154, 1963.
Metzgar, R. S. et al., Proc. Natl. Acad. Sci., USA, vol. 81, p. 5242, 1984.
Nakamura et al., 1987.
Nepom, G. T. et al., Proc. Natl. Acad. Sci., USA, vol. 81, p. 2864, 1984.
Nisole S. et al., The HB-19 pseudopeptide 5[Kpsi(CH2N)PR]-TASP inhibits attachment of T lymophocyte- and macrophage-tropic HIV to permissive cells, AIDS Res. Hum. Retroviruses, 16(3): 237-49, Feb. 10, 2000.
Nisole, S. et al., Anchorage of HIV on permissive cells leads to coaggregation of viral particles with surface nucleolin at membrane raft microdomains, Exp. Cell Res., vol. 276, p. 155-173, 2002.
Nisole, S. et al., The anti-HIV pentameric Pseudopeptide HB-19 binds the C-terminal end of nucleolin an dprevents anchorage of virus particles in the plasma membrane of target cells, J. Biol. Chem., vol. 227, No. 23, p. 20877-20886, 2002.
Nisole, S. et al., The anti-HIV Pseudopeptide HB-19 forms a complex with the cell-surfaceexpressed nucleolin independent of heparin sulfate proteoglycans, J. Biol. Chem., vol. 274, No. 39, p. 27875-27884, 1999.
Okawa et al., Journal of Immunological Methods, vol. 149, p. 127, 1992.
Order, S. E. et al., Int. J. Radiother. Oncol. Bio. Phys., vol. 8, p. 121, 1982.
O'Reilly, M. S. et al., Endostatin: an endogenous inhibitor of angiogenesis and tumor growth, Cell, 88(2), p. 277-285, 1997.
Otake, Y. et al., Overexpression of nucleolin in chronic lymphocytic leukemia cells induces stabilization of bc12 mRNA, Blood, 109(7), p. 3069-3075, 2007.
Otake, Y. et al., Retinoid-induced apoptosis in HL-60 cells is associated with nucleolin down-regulation and destabilization of Bc1-2 mRNA, Mol. Pharmacol., 67(1), p. 319-326, 2005.
Page, N. et al., The spliceosomal phosphopeptide P140 controls the lupus disease by interacting with the HSC70 protein and via a mechanism mediated by hammadelta T cells, PLos One, 4(4), p. 5273, 2009.
Papsidero, L. D. et al., Cancer. Res., vol. 44, p. 4653, 1984.
Pardridge et al., PNAS USA, vol. 92, p. 5592-5596, 1995.
PCT International Search Report for WO 2007/125210 dated Jun. 30, 2008.
PCT International Search Report for WO 2009/141687 dated Sep. 2, 2009.
PCT International Search Report for PCT/EP2011/067337.

Peifer, C. et al., New approaches to the treatment of inflammatory disorders small molecule inhibitors of p38 MAP kinase, Curr. Top. Med. Chem., vol. 6, No. 2, p. 113-149, 2006.
Pekary, A. E. et al., Clin. Chem., vol. 30, p. 1213-1215, 1984.
Perez, P. et al., J. Exper. Med., Vo.. 163, p. 166-178, 1986.
Phase I Trial in Patients with Malignant Melanoma, Proc. Natl. Acad. Sci., USA, vol. 82, pp. 1242-1246, 1985.
Philben, V. J. et al., Cancer, vol. 57, p. 571-576, 1986.
Pimm, M. V. et al., Cancer Immunol. Immunother., vol. 12, p. 125-134, 1982.
Prog. Neuropsychopharmacol. Biol. Psychiatry, vol. 23, p. 941-949, 1999.
Qi, W. et al., NSC348884, a nucleophosmin inhibitor disrupts oligomer formation and induces apoptosis in human cancer cells, Oncogene, 27(30), p. 4210-4220, 2008.
Remington's Pharmaceutical Sciences, Mack Publishing Co., A. R. Gennaro edit, 1985.
Reyes-Reyes, E. M. et al., Cell-surface nucleolin is a signal transducing P-selectin binding protein for human colon carcinoma cells, Exp. Cell Res., 314(11-12), p. 2212-2223, 2008.
Rot, A., Neutrophil attractant/activation protein-1 (intrleukin-8) induces in vitro neutrophil migration by haptotactic mechanism, Eur. J. Immunol., vol. 23, p. 303-306, 1993.
Said, A. E. et al., Pleiotrophin inhibits Hiv infection by binding the cell surface-expressed nucleolin, Febs J., vol. 272, p. 4646-4659, 2005.
Said, A. E. et al., The anti-HIV cytokine midkine binds the cell surface-expressed nucleolin as a low affinity receptor, J. Biol, Chem., vol. 277, No. 40, p. 37492-37502, 2002.
Sakarellos-Daltsiotis et al., Vaccine (2000) 18, 302-310.
Schroeder, et al., Diffusion Enhancement of Drugs by Loaded Nanoparticles in Vitro, Prog. Neuropsychopharmacol. Biol. Psychiatry, vol. 23, pp. 941-949, 1999.
Schulz, G. et al., Proc. Natl. Acad. Sci., USA, vol. 80, p. 5407, 1983.
Sears, H. F. et al., Cancer Res., vol. 45, p. 5910, 1985.
Seko, Y. et al., the role of cytokine mRNA stability in the pathogenesis of autoimmune disease, Autoimmun. Rev., vol. 5, p. 299-305, 2006.
Semenkovich, C. F. et al., A protein partially expressed on the surface of HepG2 cells that binds lipoproteins specifically is nucleolin, Biochemistry, vol. 29, p. 9708-9713, 1990.
Sengupta, T. K. et al., Identification of nucleolin as an AU-rich element binding protein involved in bc1-2 mRNA stabilization, J. Biol. Chem., 279(12), p. 10855-10863, 2004.
Shi, H. et al., Nucleolin is a receptor that mediates antiangiogenic and antitumor activity of endostatin, Blook, 110(8), 1899-1906, 2007.
Shun, C. T. et al., Glucosyltransferases of viridans streptococci are modulins of interleukin-6 induction in infective endocarditis, Infec. Immun., vol. 73, No. 6, p. 3261-3270, 2005.
Siccardi, A. G. et al., Cancer Res., vol. 46, p. 4817-4822, 1986.
Soundararajan, S. et al., the nucleolin targeting aptamer AS1411 destabilizes Bc1-2 messenger RNA in human breast cancer cells, Cancer Res., 68(7), p. 2358-2365, 2008.
Srivastava, M. et al., Molecular dissection of nucleolin's role in growth and cell proliferation: new insights, Fasteb J., vol. 13, p. 1911-1922, 1999.
Stepanova, V. et al., Nuclear translocation of urokinase-type plasminogen activator, Blood, 112(1), p. 100-110, 2008.
Stewart, J. M. et al., Solid phase peptide synthesis, $2^{nd}$ edition, Rockford, Pierce Chemical Company, 91, 1984.
Takagi, M. et al., Regulation of p53 translation and induction after DNA damage by ribosomal protein L26 and nucleolin, Cell, 123(1), p. 49-63, 2005.
Tate, A. et al., Met-Independent Hepatocyte Growth Factor-mediated regulation of cell adhesion of human prostate cancer cells, BMC Cancer, vol. 6, p. 197, 2006.
Turck, N. et al., Effect of laminin-1 on intestinal cell differentiation involves inhibition of nuclear nucleolin, J. Cell. Physio., 2006(2), p. 545-555, 2006.

(56) References Cited

OTHER PUBLICATIONS

Tyler et al., Febs lett., vol. 421, p. 280-284, 1999.
Tyler et al., PNAS USA, vol. 96, p. 7053-7058, 1999.
Ugrinova, I. et al., Inactivation of nucleolin leads to nucleolar disruption, cell cycle arrest and defects in centrosome duplication, BMC Mol. Biol., 8(1), p. 66, 2007.
Uhr, J. W. et al., Monoclonal Antibodies and Cancer, Academic press, Inc., p. 85-98, 1983.
Vitetta, E. S. et al., Biotechnology and Biol. Frontiers, Ed. P. H. Abelson, p. 73-85, 1984.
Vitetta, E.S. et al., Sci., vol. 219, p. 644-650, 1983.
Xu et al., J. Biol. Chem., vol. 276, p. 43221, 2001.
Zalcberg, J. R. et al., J. Natl. Cancer Inst., vol. 72, p. 697, 1984.
Zanotti et al., Cytokine modulation in sepsis and septic shock, Expert Opin. Investig. Drugs, vol. 11, p. 1061-1075, 2002.
Yip, George W., et al., "Therapeutic value of glycosaminoglycans in cancer", Mol. Cancer Ther., Sep. 2006, pp. 2139-2148.
U.S. Appl. No. 13/877,491, filed Jun. 2013.

A. Protein structure of nucleolin   B. HB-19 binding

RGG domain aa 644- KGEGGFGGRGGGRGGFGGRGGGRGGRGGFGGRG
RGGFGGRGGFRGGRGGGGDHKPQGKKTKFE - aa 707

A

K-P-R-K-K-K-G-P-K-E-K-AhxCONH$_2$

HB-19

B
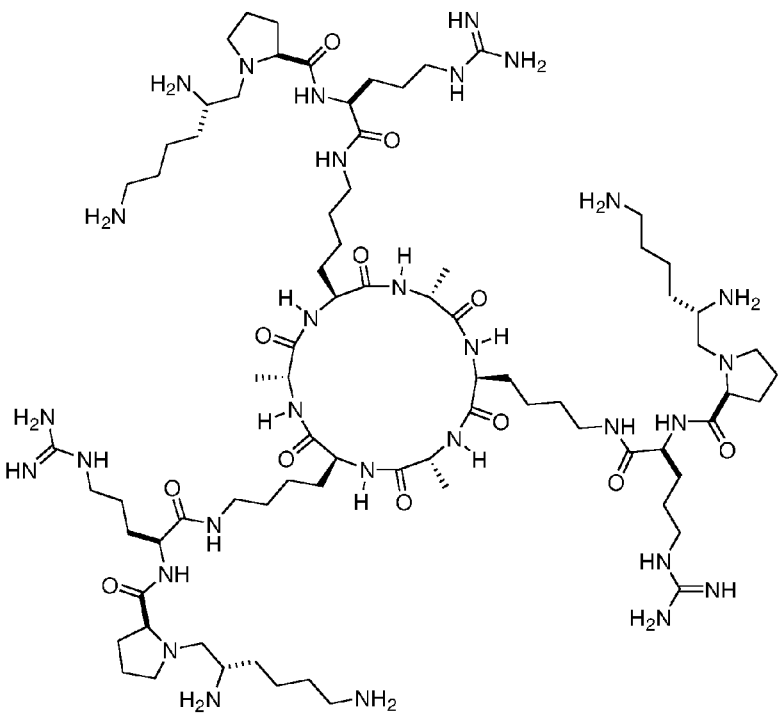
Nucant 01
C
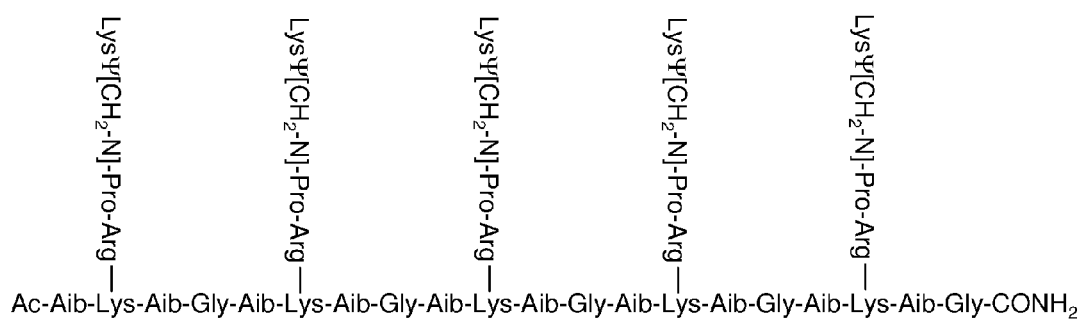
Nucant 2
Figure 2B and C

D
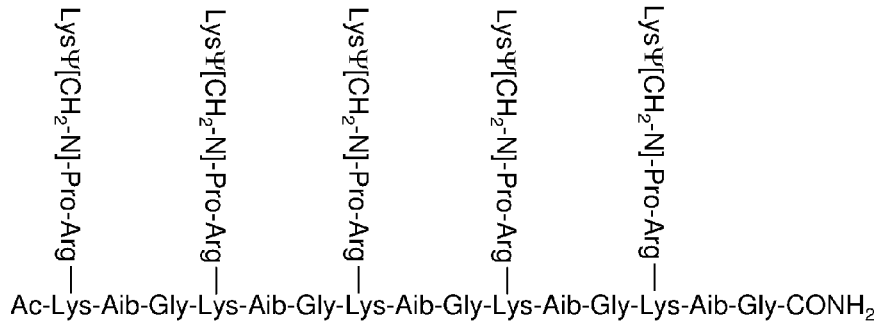
Nucant 3
E
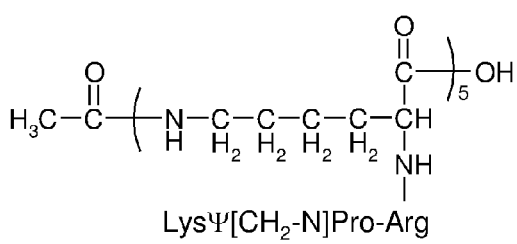
Nucant 4
F
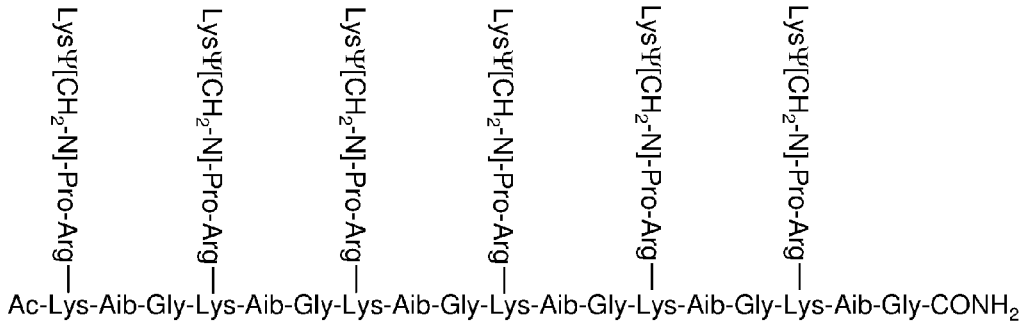
Nucant 6
Figure 2D, E and F G
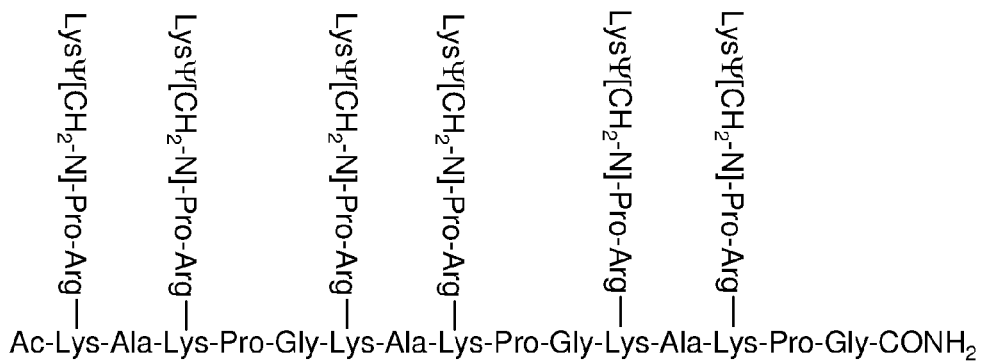
Nucant 7
H
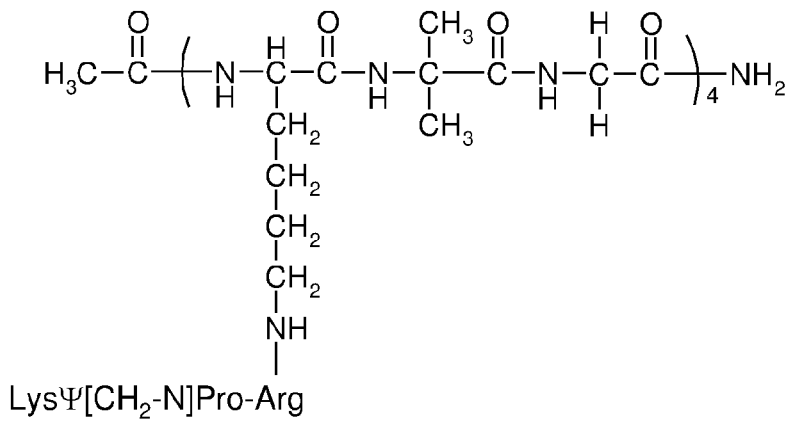
Nucant 8
I
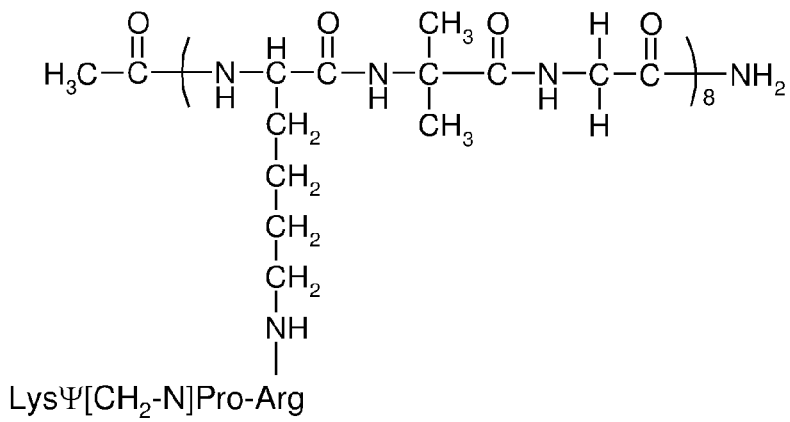
Nucant 9
Figure 2G, H and I

A

B

COMPOSITIONS COMPRISING MULTIVALENT SYNTHETIC LIGANDS OF SURFACE NUCLEOLIN AND GLYCOSAMINOGLYCANS

This application incorporates by reference the contents of a 18.6 kb text file created on Apr. 1, 2013 and named "pctep2011067337sequencelisting.txt," which is the sequence listing for this application.

FIELD OF THE INVENTION

The present invention relates to compositions comprising a multivalent synthetic compound and a glycosaminoglycan (GAG), and their use for the treatment of cancer, diseases involving angiogenesis, inflammatory diseases, and for promoting wound healing.

BACKGROUND

Mitosis is the cell division process used by eurkaryotic cells in order to support growth, repair, tissue regeneration, and/or to replace dead cells.

In cancer cells, regulation of mitosis is defective and this is why these cells divide anarchically and give rise to tumours. Thus, one effective therapeutic route to prevent the development of cancer consists in blocking the division of cancerous cells using molecules with anti-mitotic or other anti-cancer properties.

Nevertheless, current anti-mitotic molecules (paclitaxel, better known under the name taxol, or colchicine for example) act without cell specificity on all cells without distinction, thus causing many unwanted side effects. It is therefore essential to develop anti-mitotic molecules with fewer harmful effects.

Every tumour needs nutrients and oxygen in order to grow. These elements are provided by intratumoral blood vessels which result from a mechanism known as angiogenesis. In fact, if these vessels are absent, tumour cells undergo a cell necrosis process, and tumour growth slows down then stops. An example of another therapeutic route to combat cancer therefore consists in blocking the angiogenesis process by blocking the molecules controlling this mechanism.

The plurality of current anti-angiogenic molecules are specific to one angiogenic factor. This monospecificity gives rise to resistance phenomena. Inhibition of one angiogenic factor type produces expression of another type by angiogenic compensation mechanisms. It is therefore beneficial to have available anti-angiogenic molecules with a broad spectrum of activity against the factors implicated.

However, inhibition of the angiogenesis process alone is generally found to be insufficient to effectively block tumour growth. In addition, it does not block the formation of metastases.

It would therefore be extremely useful to have available new anti-cancer molecules capable of inhibiting both tumour cell proliferation and the angiogenesis process in the tumour. In fact, a recent study has shown that a combination of two therapeutic molecules, one anti-mitotic and the other anti-angiogenic, produces a synergetic effect and significantly increases the efficacy of overall treatment compared to treatment with only one of these molecules.

Heretofore, no molecule with both these effects, anti-mitotic and anti-angiogenic, has been reported.

Moreover, the majority of current anti-cancer agents are not truly specific to tumour cells and therefore also target healthy cells, thus giving rise to many, and at times serious, side effects. This problem has been resolved in some cases by the development of antibodies which target the surface molecules of some tumours. However, the use of antibodies poses other serious problems and the development of effective therapeutic antibodies that are non-toxic is a lengthy, uncertain and expensive procedure. Moreover, the production of antibodies on a large scale and under strict health and safety conditions is particularly difficult. As a result, treatments based on specific antibodies are still far and few between and extremely costly.

Another problem linked to conventional anti-cancer drugs, such as paclitaxel, is that these molecules are often highly hydrophobic which makes it necessary to develop complicated and expensive pharmaceutical formulations in order to achieve acceptable bioavailability in vivo. The problem of in vivo bioavailability is all the more acute in the case of treatment using nucleic acids since it is extremely difficult for them to reach their target cells in an efficacious and specific manner.

It would therefore be extremely useful to have available new anti-cancer molecules which present the following characteristics: much improved efficacy as a result of their dual inhibitory action on tumour proliferation and angiogenesis such that they can be effective alone, without the use of conventional chemotherapy or radiotherapy and thus greatly the limit side effects linked to these types of treatment, a fairly broad spectrum of activity against angiogenic factors to prevent resistance to treatment, very few side effects as a result of greater specificity towards tumour cells, a synthesis process that is easily adaptable to an industrial scale, easier to use, notably as a result of better bioavailability and/or longer half-life in vivo, in particular as a result of direct specificity for tumour cells, with good solubility in aqueous media and improved resistance to in vivo breakdown processes.

Thus, there is a need in the field for compositions and methods for the inhibition of detrimental forms of cell proliferation, and notably cancer cell growth.

WO2007/125210 discloses polyvalent or multivalent synthetic peptides made of at least three particular pseudopeptide units grafted to a support. This family of compounds (which have been named Nucant compounds), has been shown to interact with surface nucleolin RGG domain and to have both anti-proliferative and anti-angiogenic properties and to be useful for the treatment of cancer or inflammatory diseases. They have a fairly broad spectrum of activity against angiogenic factors, a good solubility in aqueous media, improved resistance to in vivo breakdown processes (due to the presence of a modified bond in pseudopeptide units), showed very few side effects, and have a synthesis process that is easily adaptable to an industrial scale. Specific exemplified compounds include compound HB19 and compounds Nucant 1, 2, 3, 6 and 7 (see FIG. 2 of this document). This document is herein incorporated in its entirety.

WO2009/141687 discloses improved Nucant compounds, in which lysine residues in the pseudopeptide units are all in the same L or D configuration. This document notably describes compound Nucant 6L (N6L), which corresponds to compound Nucant 6 as disclosed in WO2007/125210, in which all lysine residues of the pseudopeptide units are in L configuration. This compound showed improve anti-cancer activity compared to complex compound Nucant 6 in which the lysine residue of each pseudopeptide unit may be in L or D configuration. The compounds were also shown to improve wound healing. This document is herein incorporated in its entirety. WO2009/141687 also discloses compounds Nucant 4, 8 and 9 (see claim 10 of this document).

While the Nucant compounds disclosed in the two above mentioned documents are very interesting as such, it would still be desirable to further improve their anti-proliferative and anti-angiogenic properties. Indeed, this would permit to decrease the amount that would be therapeutically effective, thus decreasing the cost of treatment and further limiting side effects.

SUMMARY

The present invention relates to the surprising and unexpected discovery that Nucant compounds or multivalent synthetic entities of the invention interact with glycosaminoglycans (GAGs) to mediate and/or enhance their beneficial therapeutic activity, e.g., anti-proliferative activity. For example, a combination of a Nucant with a GAG, e.g., heparin, can significantly increase the anti-cancer potency of the Nucant.

In one aspect, the invention thus provides a composition, notably a therapeutic composition, comprising a Nucant and at least one glycosaminoglycan (GAG). Accordingly, in certain embodiments the invention provides a composition, notably a therapeutic composition, comprising a complex of a GAG and a Nucant as described herein. In certain embodiments, the Nucant is a peptide or pseudopeptide, e.g., HB-19 or N6L. In any of the compositions described herein, the therapeutic compositions provided by the invention optionally include a pharmaceutically acceptable carrier, excipient or adjuvant.

In another aspect, the invention provides methods for treating and/or preventing the proliferation of a cell comprising administering a composition comprising an effective amount of a Nucant and at least one GAG, and/or of a complex of a Nucant as described herein and a GAG to a subject, in vitro, in vivo or ex vivo, wherein the composition is effective in inhibiting or preventing the proliferation of the cell. In an exemplary embodiment of this aspect, the subject is a cell or an individual. In certain embodiments, the Nucant is a peptide or pseudopeptide, e.g., HB-19 or N6L. In certain embodiments, the cell is a eukaryotic cell, e.g., a cancer cell or other proliferating cell.

In another aspect, the invention provides methods for treating and/or preventing a disease or disorder related to the growth and/or proliferation of a cancer cell in an individual comprising administering a composition comprising an effective amount of a Nucant as described herein and a GAG to an individual, wherein the composition is effective in inhibiting or preventing the growth and/or proliferation the cancer cell.

It has also been surprisingly and unexpectedly discovered that the Nucants as described herein form microspheres when admixed with a GAG. Therefore, in certain aspects the invention also provide a composition, notably a therapeutic composition, comprising microspheres including a Nucant as described herein and a GAG. In an additional aspect, the invention provides methods for forming the Nucant/GAG microspheres comprising admixing a Nucant together with a GAG, wherein the components spontaneously form microspheres. In an additional aspect, the invention provides methods of treating a disease or disorder, e.g., cancer, comprising the step of administering to a subject or an individual an effective amount of a therapeutic composition comprising microspheres of a Nucant and a GAG. In certain embodiments, the microspheres are formed prior to administration. In an additional embodiment, the microspheres are formed after administration to the subject or patient, e.g., in vivo.

The present invention further provides any invention described herein.

The preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference, and for convenience are listed in the appended bibliography.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

DETAILED DESCRIPTION

Figure 1:
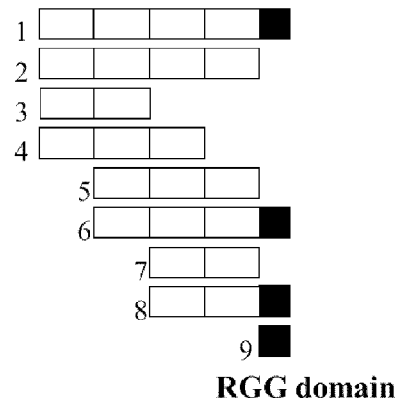
FIG. 1. Structure of nucleolin protein. A. Human nucleolin consists of 707 amino acids. Nucleolin can be broken down into two main parts (Ginisty, H., Sicard, H., Roger, B., and Bouvet, P. Structure and functions of nucleolin. (1999) J. Cell Science 112, 761-772; Srivastava, M., and Pollard, H. B. Molecular dissection of nucleolin's role in growth and cell proliferation: new insights. (1999) FASEB J. 13, 1911-1922): N-terminal (aa 1-308), and C-terminal (aa 309-707). The N-terminal domain consists of 4 long acidic domains, consisting of an uninterrupted repetition of glutamic acid and aspartic acid (A1, A2, A3, A4). The C-terminal domain, consists of alternating hydrophobic and hydrophilic regions forming 4 RNA Binding Domains (RBD I, II, III, and IV), and its extremity (aa 644-707) carries the highly basic RGG domain comprised of Arg-Gly-Gly repetitions. B. Identification of the binding domain of compound HB19 to nucleolin requires the RGG domain. Nucleolin constructions corresponding to the N- and C-terminal areas were obtained by in vitro transcription/translation in a system using rabbit reticulocyte lysates. Thus, whole nucleolin and the N- and C-terminal parts contain amino acids 1-707, 1-308 and 309-707 respectively labelled with [$^{35}$S] Met/Cys were produced. The labelled crude product was then incubated with biotinylated HB19 and the complexes were purified on an avidin-agarose column. As expected, whole nucleolin interacts with HB19. On the other hand, the N-terminal part of the nucleolin rich in acid residues does not interact at all with the compound whereas the C-terminal part of nucleolin contains the target for HB19 (Nisole, S., Said, E. A., Mische, C., Prevost, M. C., Krust, B., Bouvet, P., Bianco, A., Briand, J. P., and Hovanessian, A. G. The anti-HIV pentameric compose HB-19 binds the C-terminal end of nucleolin and prevents anchorage of virus particles in the plasma membrane of target cells. (2002) J. Biol. Chem. 277, 20877-20886). Having identified that the C-terminal part of the nucleolin contains the target for HB19, various constructions (FIG. 2, nos. 1 to 9) of this region were made up. The first construction corresponds to cDNA coding for the C-terminal part of human nucleolin including the 4 RBDs and the RGG domain, in fusion with GST protein (Glutathione S-Transferase) to allow detection with anti-GST antibodies. The other constructions, also in fusion with GST, correspond to this same part but one or more domains shorter. All these proteins are produced by E. coli. The capacity of HB19 to interact with each construction was tested by incubating crude bacterial extracts, expressing different nucleolin constructions, with biotinylated HB19 which was then purified by fixing to Avidine-agarose. These samples were then analysed by polyacrylamide gel and GST, and revealed by immunodetection (Western Blot) using anti-GST antibodies. The results show that the presence of the RGG domain is necessary for the interaction between HB19 with the C-terminal part of nucleolin. Moreover, the RGG domain alone is enough for this interaction.
Figure 1:
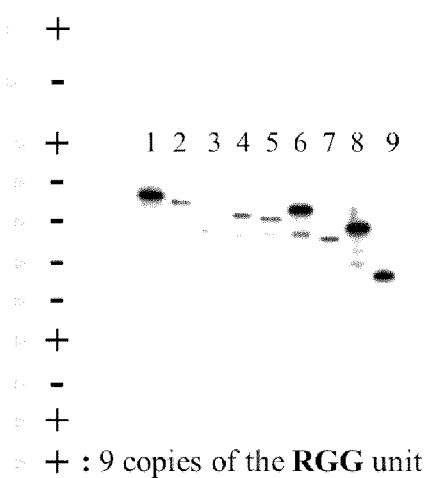

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific term's used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

Unless defined otherwise, all technical and scientific terms used herein have the meaning commonly understood by a person skilled in the art to which this invention belongs. The following references, the entire disclosures of which are incorporated herein by reference, provide one of skill with a general definition of many of the terms used in this invention: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ Ed., R. Rieger et al. (eds.), Springer Verlag (1991); and Hale & Marham, the Harper Collins Dictionary of Biology (1991). As used herein, the following terms may have meanings ascribed to them below, unless specified otherwise. However, it should be understood that other meanings that are known or understood by those having ordinary skill in the art are also possible, and within the scope of the present invention. All publications, patent applications, patents, and other references mentioned herein are incorporated by reference in their entirety. In the case of conflict, the present specification, including definitions, will control. In addition, the materials, methods, and examples are illustrative only and not intended to be limiting.

It must be noted that as used herein and in the appended claims, the singular forms "a", "and", and "the" include plural references unless the context clearly dictates otherwise. All technical and scientific terms used herein have the same meaning.

In order that the present invention may be more readily understood, certain terms are first defined.

As used herein, "derivatives" are compositions formed from the native compounds either directly, by modification, or by partial substitution. As used herein, "analogs" are compositions that have a structure similar to, but not identical to, the native compound.

The term "peptides" can mean, but is in no way limited to, recombinant polypeptide having at least 4 amino acids connected by peptide bonds. Furthermore, peptides of the invention may include amino acid mimentics, and analogs. Recombinant forms of the peptides can be produced according to standard methods and protocols which are well known to those of skill in the art, including for example, expression of recombinant proteins in prokaryotic and/or eukaryotic cells followed by one or more isolation and purification steps, and/or chemically synthesizing peptides or portions thereof using a peptide synthesizer.

The term, "biologically active" or "bioactive" can mean, but is in no way limited to, the ability of an agent, such as the Nucants provided by the invention, to effectuate a physiological change or response. The response may be detected, for example, at the cellular level, for example, as a change in growth and/or viability, gene expression, protein quantity, protein modification, protein activity, or combination thereof; at the tissue level; at the systemic level; or at the organism level. Techniques used to monitor these phenotypic changes include, for example, measuring: the binding of a ligand to its receptor in or on a cell, activation of cell signaling pathways, stimulation or activation of a cellular response, secretion or release of bioactive molecules from the cell, cellular proliferation and/or differentiation, or a combination thereof. In one example, the biological activity of a peptide provided by the invention can be determined by detecting its ability to inhibit the growth and/or proliferation of a cell.

The term "effective amount/dose," "pharmaceutically effective amount/dose," "pharmaceutically effective amount/dose" or "therapeutically effective amount/dose" can mean, but is in no way limited to, that amount/dose of the active pharmaceutical ingredient sufficient to prevent, inhibit the occurrence, ameliorate, delay or treat (alleviate a symptom to some extent, preferably all) the symptoms of a condition, disorder or disease state. The effective amount depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 1000 mg/kg body weight/day of active ingredients is administered dependent upon potency of the agent. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population).

The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The term "pharmacological composition," "therapeutic composition," "therapeutic formulation" or "pharmaceutically acceptable formulation" can mean, but is in no way limited to, a composition or formulation that allows for the effective distribution of an agent provided by the invention, which is in a form suitable for administration to the physical location most suitable for their desired activity, e.g., systemic administration.

Non-limiting examples of agents suitable for formulation with the, e.g., Nucants provided by the instant invention include: cinnamoyl, PEG, phospholipids or lipophilic moieties, phosphorothioates, P-glycoprotein inhibitors (such as Pluronic P85) which can enhance entry of drugs into various tissues, for example the CNS (Jolliet-Riant and Tillement, 1999, Fundam. Clin. Pharmacol., 13, 16-26); biodegradable polymers, such as poly(DL-lactide-coglycolide) microspheres for sustained release delivery after implantation (Emerich, D F et al, 1999, Cell Transplant, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999). The term "pharmaceutically acceptable" or "pharmacologically acceptable" can mean, but is in no way limited to, entities and compositions that do not produce an adverse, allergic or other untoward reaction when administered to an animal, or a human, as appropriate.

The term "pharmaceutically acceptable carrier" or "pharmacologically acceptable carrier" can mean, but is in no way limited to, any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "systemic administration" refers to a route of administration that is, e.g., enteral or parenteral, and results in the systemic distribution of an agent leading to systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect. Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compositions of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful.

The term "conservative mutations" refers to the substitution, deletion or addition of nucleic acids that alter, add or delete a single amino acid or a small number of amino acids in a coding sequence where the nucleic acid alterations result in the substitution of a chemically similar amino acid. Amino acids that may serve as conservative substitutions for each other include the following: Basic: Arginine (R), Lysine (K), Histidine (H); Acidic: Aspartic acid (D), Glutamic acid (E), Asparagine (N), Glutamine (Q); hydrophilic: Glycine (G), Alanine (A), Valine (V), Leucine (L), Isoleucine (I); Hydrophobic: Phenylalanine (F), Tyrosine (Y), Tryptophan (W); Sulfur-containing: Methionine (M), Cysteine (C). In addition, sequences that differ by conservative variations are generally homologous.

The term "binding" can mean, but is in no way limited to, the physical or chemical interaction, direct or indirect, between two molecules (e.g., compounds, amino acids, nucleotides, polypeptides, or nucleic acids). Binding includes covalent, hydrogen bond, ionic, non-ionic, van der Waals, hydrophobic interactions, and the like.

The term "cell" can mean, but is in no way limited to, its usual biological sense, and does not refer to an entire multicellular organism. The cell can, for example, be in vivo, in vitro or ex vivo, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

The present invention relates to the surprising and unexpected discovery that Nucant compounds or entities as described herein interact with GAGs to mediate and/or enhance their beneficial therapeutic activity, e.g., anti-proliferative activity. For example, a combination of a Nucant with a GAG, e.g., heparin, can significantly increase the anti-cancer potency of the Nucant.

Thus, in certain embodiments, the invention provides a composition, preferably a therapeutic composition comprising an effective amount of a Nucant, e.g., HB-19 or N6L, as described herein, in combination with at least one glycosaminoglycan (GAG).

The invention also provides a composition, notably a therapeutic composition, comprising a complex of a GAG and a Nucant as described herein.

It has also been surprisingly and unexpectedly discovered that the Nucants as described herein form microspheres when admixed with a GAG. Therefore, in certain aspects, the invention also provides a composition, notably a therapeutic composition, comprising microspheres including a Nucant as described herein and a GAG. In an additional embodiment, the invention provides a microsphere or plurality of microspheres comprising a combination of a Nucant and a GAG. In certain embodiments, the Nucant is a peptide or pseudopeptide, e.g., HB-19 or N6L. As used herein, the term "Nucant" can mean but is in no way limited to a nucleolin-binding compound or entity, e.g., a nucleolin antibody or nucleolin antagonist, including, for example, a nucleolin binding peptide or pseudopeptide, derivative or analog thereof (collectively "Nucant peptide"). In certain embodiments, the Nucant compounds comprise a support on which at least 3 pseudopeptide units are grafted, said compound being of Formula (I):

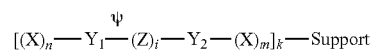

wherein
each X independently represents any amino acid;
$Y_1$ and $Y_2$ are selected independently from amino acids having a basic side chain;
Z is selected from proline, optionally substituted at γ, β or δ; a natural or non N-alkylamino acid; a dialkylamino acid; a cyclic dialkylamino acid; pipecolic acid or a derivative thereof;
n and i independently are 0 or 1;
m is an integer between 0 and 3
k is an integer greater than or equal to 3; and
Ψ represents a modified peptide bond which is significantly more resistant to at least one protease than a standard peptide bond.

In the context of the invention, the term "support" refers to any pharmaceutically acceptable molecule, in other words without intrinsic toxicity, on which at least 3 pseudopeptide units of formula (I) can be grafted. An acceptable support therefore has to be of sufficient size to allow at least 3 pseudopeptide units of formula (I) to be grafted on it, preferably 3 to 8 pseudopeptide units of formula (I). Such an acceptable support should also preferably be large enough to allow at least 3, preferably 3 to 8, pseudopeptide units of formula (I) can come together to interact in the RGG domain of one or more nucleolin molecules. In addition, the support must not be immunogenic.

Such a support can be selected from a linear peptide or cyclic peptide, a peptoid (N-substituted glycine oligomer) that is linear or cyclic, a foldamer (oligomer or polymer with a strong tendency to adopt a compact, well-defined and predictable conformation in solution), a linear polymer or a spherical dendrimer (macromolecule consisting or polymers which combine according to a tree like process around a multifunctional central core) a sugar or a nanoparticle. Advantageously, said support is selected from a linear or a cyclic peptide or even a linear or cyclic peptoid.

The use of a linear peptide (see structure of Nucant peptides HB19, Nucant 2-3, and 6-9 in FIG. 2) allows the support to be synthesised easily and the results obtained by the inventors with compounds HB19 and N6L show that such a support does in effect resolve the technical problems posed by this application. A linear peptide acting as a support in the invention can advantageously contain a proportion of lysine greater than 25%. More precisely, when a linear peptide is used as a support in the invention, the pseudopeptide units are preferably grafted in position g of lysine. When a linear peptide is used as the support in the invention, it therefore preferably includes at least as many lysine as the number of pseudopeptide units which are to be grafted on.

For example, a support linear peptide can have a sequence selected from KKKGPKEKGC (SEQ ID NO:1), KKKKGC (SEQ ID NO:2), KKKKGPKKKKGA (SEQ ID NO:3) or KKKGPKEKAhxCONH$_2$ (SEQ ID NO:4), wherein Ahx represents hexanoic amino acid and CONH$_2$ represents the fact that the acid group is replaced by an amide group, AhxCONH$_2$, representing (2S)-2-aminohexanamide, or a linear sequence consisting of 2-4 units (KAKPG, SEQ ID NO:12), namely sequence AcKAKPGKAKPGKAKPG-CONH$_2$ (SEQ ID NO:13, where Ac represents an acetyl group CH$_3$—CO—, and CONH$_2$ means that the acid group COOH of glycine is replaced by an amide group CONH$_2$). Advantageously, the support linear peptide can be peptide KKKGPKEKAhxCONH$_2$ (see for example HB19 in FIG. 2A, SEQ ID NO:5, which has this linear peptide as support.), or peptide AcKAKPGKAKPGKAKPGCONH$_2$ (SEQ ID NO:13, where Ac represents an acetyl group CH$_3$—CO— and CONH$_2$ means that the acid group COOH of glycine is replaced by an amide group CONH$_2$, for example, Nucant 7 in FIG. 2G, SEQ ID NO:17, which has this linear peptide as a support).

Among the linear peptides, some are known to adopt a helicoidal structure. These linear peptides can also be used as supports in the invention. Such linear peptide supports from a helicoidal structure comprised of supports consisting of an integer greater than or equal to 3, namely 3 to 8, repetitions of the peptide units of sequence Aib-Lys-Aib-Gly (SEQ ID NO:6) or Lys-Aib-Gly (SEQ ID NO:7) respectively where Aib represents 2-amino-isobutyric acid. As each of these units consists of a single lysine residue (Lys), as many repetitions of these units are needed as are to be grafted on pseudopeptide units of formula (I).

For example, to obtain a quadrivalent compound with 4 pseudopeptide units of formula (I), the support can be a linear peptide forming a helicoidal structure of formula Ac-Lys-Aib-Gly-Lys-Aib-Gly-Lys-Aib-Gly-Lys-Aib-Gly-CONH$_2$ (SEQ ID NO:22), where Ac represents a CH$_3$—CO— group and CONH$_2$ means that the acid group COOH of glycine is replaced by an amid group CONH$_2$ (see for example Nucant 8 in FIG. 2H, SEQ ID NO:23, which has this peptide as a support).

Alternatively, to obtain a pentavalent compound with 5 pseudopeptide units of formula (I), the support can be a linear peptide forming a helicoidal structure of formula Aib-Lys-Aib-Gly-Aib-Lys-Aib-Gly-Aib-Lys-Aib-Gly-Aib-Lys-Aib-Gly-Aib-Lys-Aib-Gly (SEQ ID NO:8) or Lys-Aib-Gly-Lys-Aib-Gly-Lys-Aib-Gly-Lys-Aib-Gly-Lys-Aib-Gly (SEQ ID NO:9). Advantageously, a linear peptide forming a helicoidal structure of formula derived from SEQ ID NO:8 and 9 is used. This formula is selected from Ac-Aib-Lys-Aib-Gly-Aib-Lys-Aib-Gly-Aib-Lys-Aib-Gly-Aib-Lys-Aib-Gly-Aib-Lys-Aib-Gly-CONH$_2$ (SEQ ID NO:18, where Ac represents an acetyl group CH$_3$—CO— and CONH$_2$ means that the COOH acid group of glycine is replaced by an amide group CONH$_2$, see for example Nucant 2 in FIG. 2C, SEQ ID NO:20, which has this peptide as a support) or Ac-Lys-Aib-Gly-Lys-Aib-Gly-Lys-Aib-Gly-Lys-Aib-Gly-Lys-Aib-Gly-CONH$_2$ (SEQ ID NO:19, where the Ac group represents an acetyl group CH$_3$—CO— and CONH$_2$ means that the COOH acid group of glycine is replaced by an amide group CONH$_2$, see for example Nucant 3 in FIG. 2D, SEQ ID NO:21, which has this peptide as a support).

Alternatively, to obtain a hexavalent compound with 6 pseudopeptide units of formula (I), the support used can be a linear peptide forming a helicoidal structure of formula Ac-Aib-Lys-Aib-Gly-Aib-Lys-Aib-Gly-Aib-Lys-Aib-Gly-Aib-Lys-Aib-Gly-Aib-Lys-Aib-Gly-Aib-Lys-Aib-Gly-CONH$_2$ (SEQ ID NO:14, where Ac represents a CH$_3$—CO— group and CONH$_2$ means that the acid group COOH of glycine is replaced by an amide group CONH$_2$) or Ac-Lys-Aib-Gly-Lys-Aib-Gly-Lys-Aib-Gly-Lys-Aib-Gly-Lys-Aib-Gly-Lys-Aib-Gly-CONH$_2$ (SEQ ID NO:15, where Ac represents a CH$_3$—CO— group and CONH$_2$ means that the acid group COOH of glycine is replaced by an amid group CONH$_2$, see for example Nucant 6 in FIG. 2F, SEQ ID NO:17, which has this peptide as a support).

Alternatively, to obtain an octavalent compound with 8 pseudopeptide units of formula (I), the support used can be a linear peptide forming a helicoidal structure of formula Ac-Lys-Aib-Gly-Lys-Aib-Gly-Lys-Aib-Gly-Lys-Aib-Gly-Lys-Aib-Gly-Lys-Aib-Gly-Lys-Aib-Gly-Lys-Aib-Gly-CONH$_2$ (SEQ ID NO:24), where Ac represents a CH$_3$—CO— group and CONH$_2$ means that the acid group COOH of glycine is replaced by an amid group CONH$_2$ (see for example Nucant 9 in FIG. 2I, SEQ ID NO:25, which has this peptide as a support).

A cyclic peptide or peptoid can also be advantageously used as support. In particular, this allows the flexibility of the structure to be restricted. A support cyclic peptide or peptoid can be mainly be selected from hexa-, octa-, deca- or dodeca-cyclic peptide, preferably consisting of amino acid residues in the L (levorotatory) and D (dextrorotatory) configuration in alternation (D,L-cyclopeptide) or a chain of N-alkyl Glycine residue (cyclic peptoid). An example of a compound with such a support is a cyclic hexapeptide consisting of alternate alanine (A) residues of configuration D and lysine residues (K) of configuration L with 3 KPR units with a Φ (—CH$_2$N—) bond between K and P as shown in FIG. 2B (compound Nucant 01).

A support made of 5 lysine residues linked by amide bonds at the ε amino group of each Lysine residue may also be used (see compound Nucant 4 in FIG. 2E).

Advantageously, the support for a compound of formula (I) according to the invention is a support selected from a cyclic hexapeptide consisting of:
alternating alkaline (A) residues of configuration D and Lysine (K) residues of configuration L (see compound Nucant 01 in FIG. 2B),
5 lysine residues linked by amide bonds at the ε amino group of each Lysine residue (see compound Nucant 4 in FIG. 2E), and
a linear peptide of sequence SEQ ID NO:1, SEQ ID NO:2, SEQ ID NO:3, SEQ ID NO:4, SEQ ID NO:8, SEQ ID NO:9, SEQ ID NO:13, SEQ ID NO:14, SEQ ID NO:15, SEQ ID NO:18, SEQ ID NO:19, SEQ ID NO:22 and SEQ ID NO:24.

In the context of the invention, the term "grafted" for the pseudopeptide units means being bound to the support by means of a covalent bond, either directly or through the intermediate of a spacer compound between the pseudopeptide and support. As a result of this, in one particular embodiment, the pseudopeptide units are grafted directly on the support without a spacer compound between them and the support. In another embodiment, the pseudopeptide units are grafted on the support through the intermediate of a spacer. Examples of acceptable spacers include compounds of the type ethylene glycol, piperazine or an amino acid of the type aminohexanoic acid or beta-alanine.

In the case where the support is a linear or cyclic peptide and where the pseudopeptide units are grafted directly on the peptide, bonding between the peptide and the pseudopeptide units is preferably carried out at the lysine residue of the peptide support, at the amino group in the α or ε position, preferably at the amino group in the position (on the side chain) of lysine. Thus, direct grafting of pseudopeptide units on the peptide support is advantageously carried out by means of an amide bond between the acid group COOH of the amino acid in the C-terminal position of the pseudopeptide unit and an amino group of the lysine residue, preferably the amino group in the ε position (on the side chain) of lysine.

In the compounds according to the invention, at least 3 pseudopeptide units are grafted on the support. In fact, the inventors' results show the importance of binding to the RGG domain of nucleolin (see FIG. 1) for exceptional anti-tumour efficacy of compound HB19 and derivative compounds or analogues. Binding to the RGG domain of nucleolin is obtained by means of multivalent presentation of several pseudopeptide units such as those incorporated into formula (I). For compounds for which the support is a linear peptide of sequence KKKGPKEKGC, KKKKGC, KKKKGPKKKKGA or KKKGPKEKAhxCONH$_2$, the inventors have shown that below 3 units (k<3), the efficacy of binding to nucleolin is lower and anti-tumour efficacy is probably less. The compounds according to the invention therefore include at least 3 pseudopeptide units grafted on the support, k being an integer greater than or equal to 3. The compounds according to the invention therefore advantageously present 3-8 pseudopeptide units (3≤k≤8) grafted on the support. Moreover, the inventors have shown that activity was optimal with 5 or 6 pseudopeptide units grafted on the support (k=5), since the efficacy of binding to nucleolin does not increase with a higher number of pseudopeptide units. Advantageously, in the compounds of formula (I), k is therefore between 3 and 8, preferably between 4 and 7, between 4 and 6, between 4 and 5, or between 5 and 6. Even more advantageously, in compounds of formula (I), k is equal to 5 or even better 6.

In the context of the invention, the term "any amino acid" means any natural or synthetic amino acid, possibly modified by the presence of one or more substituents. More precisely the term amino acid means an alpha aminated amino acid with the following general structure:

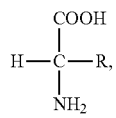

where R represents the side chain of the amino acid. In the context of the invention, R therefore represents the side chain of a side or non-side amino acid. The term "natural amino acid" means any amino acid which is found naturally in vivo in a living being. Natural amino acids therefore include amino acids coded by mRNA incorporated into proteins during translation but also other amino acids found naturally in vivo which are a product or by-product of a metabolic process, such as for example ornithine which is generated by the urea production process by arginase from L-arginine. In the invention, the amino acids used can therefore be natural or not. Namely, natural amino acids generally have the L configuration but also, according to the invention, an amino acid can have the L or D configuration. Moreover, R is of course not limited to the side chains of natural amino acid but can be freely chosen.

In the pseudopeptide units of compounds of formula (I), Z is either absent (i=0), or present (i=1) and is then selected from:
proline, possibly substituted at γ, β or δ by hydroxyl groups, amine, $C_1$-$C_{10}$ alkyl, $C_1$-$C_{10}$ alkenyl, alkynyl, $C_5$-$C_{12}$ aryl, $C_5$-$C_{14}$ aralkyl, $C_5$-$C_{12}$ heteroaryl (advantageously a $C_5$ heteroaryl), these groups themselves possibly being substituted by 1 to 6 substituents selected from a halogen atom, $NO_2$, OH, $C_1$-$C_4$ alkyl, $NH_2$, CN, trihalomethyl, $C_1$-$C_4$ alkyloxy, $C_1$-$C_4$ dialkylamino, guanadino group, thiol group;
N-alkylamino acid, natural or not;
dialkylamino acid (for example isobutyric amino acid);
cyclic dialkylamino acid; or
pipecolic acid or derivatives thereof.

The term "$C_1$-$C_i$ alkyl" means a linear or branched saturated hydrocarbon radical of formula —$C_jH_{2j+1}$, where 1≤j≤i. The $C_1$-$C_{10}$ alkyl therefore includes $C_1$ alkyls (methyl), $C_2$ (ethyl), $C_3$ (n-propyl, or isopropyl), $C_4$ (n-butyl, isobutyl, sec-butyl or tert-butyl), $C_5$ (eg: n-pentyl, neopentyl, isopentyl, tert-pentyl), and $C_6$ to $C_{10}$ alkyls. The term "$C_1$-$C_{10}$ alkanyl" means a linear or branched unsaturated hydrocarbon radical consisting of 1 to 10 carbon atoms and including at least one C=C double bond. The term "$C_1$-$C_{10}$ alkynyl" means a linear or branched unsaturated hydrocarbon radical with 1 to 10 carbon atoms and at least one C≡C triple bond. The term "$C_5$-$C_{12}$ aryl" means an aromatic polycyclic or monocyclic hydrocarbon radical with 5-12 carbon atoms. The term "$C_5$-$C_{14}$ alalkyl" means a combination of an alkyl and an aryl with a total of 5 to 14 carbon atoms. The term "$C_5$-$C_{12}$ heteroaryl" means an aryl group where at least one carbon atom on the hydrocarbon chain normally carrying 5 to 12 carbon atoms is substituted by another atom selected from N, O, or S. The term "$C_5$ heteroaryl" therefore means an aryl group where at least 1 of the 5 carbon atoms on the hydrocarbon chain is substituted by another atom selected from N, O or S. The term "$C_1$-$C_4$ alkyloxy" means a group of formula —O(O)C—($C_1$-$C_4$ alkyl), —O(O)C—($C_4$-$C_{12}$cycloalkyl), —O(O)C—($C_4$-$C_{12}$ aryl), —O(O)C—($C_4$-$C_{12}$ arylalkyl, or —O(O)C—($C_4$-$C_{12}$ heteroaryl). Advantageously, in the compound of formula (I), such an "$C_1$-$C_4$ alkyloxy" is selected from the group of formula —O(O)C—($C_1$-$C_4$ alkyl), —O(O)C—($C_4$ cycloalkyl), —O(O)C—($C_4$ aryl) —O(O)C—($C_4$ arylalkyl), or —O(O)C—($C_4$ heteroaryl). The term "$C_1$-$C_4$ dialkylamino" means a radical of formula —N($C_1$-$C_4$ alkyl)$_2$ where each alkyl is identical or different.

The term "N-alkylamino acid" means any amino acid in which one of the hydrogen atoms in the amine group is substituted by a $C_1$-$C_{10}$ alkyl chain or a $C_5$-$C_{14}$ arylalkyl group, preferably $C_5$-$C_{10}$, namely $C_{10}$, possibly substituted. Examples of N-alkylamino acids include N-methylglycine or sarcosine, N-methylisoleucine acid, N-methylvaline acid, etc. . . . The term "dialkylamino acid" means any amino acid in which 2 hydrogen atoms (on the central carbon or amine groups) are substituted by a $C_1$-$C_{10}$ alkyl chain or a $C_5$-$C_{14}$ arylalkyl group, preferably $C_5$-$C_{10}$, namely $C_{10}$, possibly substituted. Examples of dialkylamino acids include 2-amino-isobutyric acid (Aib), aminocyclopropane carboxylic acid, etc.

Advantageously, Z is present and therefore i=1. Also advantageously, when Z is present (i=1), then Z is a proline, possibly substituted at γ, β or δ as described previously.

In the pseudopeptide units of the compound of formula (I), $Y_1$ and $Y_2$ are selected from amino acids with a basic side chain. The term "amino acid with a basic side chain" means any natural or non-natural amino acid whose side chain R has a pKa value greater than 7 (pKa(R)>7). Thus, any amino acid can be used for $Y_1$ and $Y_2$, as long as its side chain has a pKa value greater than 7, preferably greater than 7.5, greater than 8, greater than 8.5 or greater than 9. In particular, among the natural amino acids those whose side chain has a pKa value greater than 7 include lysine (K, pKa(R)≈10.5), arginine (R, pKa(R)≈12.5), ornithine (inferior homologue of lysine, pKa(R)≈10.8), generally considered to be natural basic amino acids. Thus, in an advantageous embodiment, $Y_1$ and $Y_2$ are independently selected from arginine (R), lysine (K) and ornithine. Even more advantageously, $Y_1$ is a lysine (K) and $Y_2$ is an arginine (R). However, other non-natural amino acids can be used instead as long as the pKa value of their side chain R is greater than 7, preferably greater than 7.5, greater than 8, greater than 8.5, or greater than 9.

In the compounds of the invention, the pseudopeptide unit that is essential for binding to the RGG domain of nucleolin is the sub-unit of formula (II)

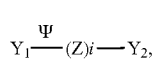
(II)

wherein $Y_1$ and $Y_2$ are as defined above. Nevertheless, the presence at one or the other end of this essential sub-unit consisting of several amino acids as defined above is not such that it would prevent binding to nucleolin. This is why the essential sub-unit of formula (II) can include at one and/or the other end 0 to 3 of any amino acids represented in the formula (I) by (X)n and (X)m respectively, where n is equal to 0 or 1 and m is an integer between 0 and 3. Advantageously, the number of the amino acids present at one and/or other end of the essential sub-unit of formula (II) is low, in other words, n is advantageously 0 and m is advantageously an integer between 0 and 2, advantageously 0 or 1, advantageously 0. Thus in an advantageous embodiment, n and m are equal to 0.

In the compounds of the invention, the sub-unit of formula (II) includes a modified peptide bond ψ, significantly more resistant to at least one protease than a standard peptide.

The term "standard peptide bond" means an amide bond of formula (—CONH—) which is normally present between 2 amino acids in a natural protein. Such a bond is sensitive to the action of proteases. The term "modified peptide bonds ψ" means a chemical bond between 2 amino acids of chemical formula distinct from the standard peptide bond of formula (—CONH—). This modified bond ψ is such that it is significantly more resistant to at least one protease than a standard peptide bond of formula (—CONH—). The term "protease", also known as "peptidase" or "proteolytic enzyme", means any enzyme which cleaves the standard peptide bonds in proteins. This process is known as proteolytic cleavage. This involves the use of a water molecule which is what leads to proteases being classified as hydrolases. The proteases namely include proteases known as N-peptidases which carry out the cleavage of the N-terminal end of proteins. These proteases are particularly inconvenient in terms of the in vivo stability of peptides without modified peptide bonds. This is why pseudopeptide units of the compounds of formula (I) include a modified bond ψ between $Y_1$ and Z (if i=1) or $Y_1$ and $Y_2$ (if i=0) such that the resistance of the sub-unit of formula (II) is significantly increased which is essential for binding to nucleolin, namely to these N-peptidases. The ψ bond should therefore make it possible to significantly increase resistance to at least one N-peptidase. This makes it possible to significantly increase the half-life of compounds of formula (I) in vivo and in vitro. For example, HB19, which has a modified bond w, has a half-life of more than 24 hours in human serum or foetal calf serum at 37° C. whereas the same compound with a standard peptide bond instead of the ψ bond only has a half-life of one hour under these same conditions.

Moreover, the inventors have found that the presence of this modified bond ψ also makes it possible to significantly increase the efficacy of binding to nucleolin. This phenomenon may be due to the fact that this allows the Nucant peptide to form an irreversible complex with nucleolin.

Various chemical bonds likely to significantly increase resistance to at least one protease are known. Thus, in an advantageous embodiment, ψ represents a reduced bond (—CH$_2$NH—) or (—CH$_2$N—) in the case where bonding takes place at the level of a secondary amine group as is the case with the bond with proline), a retro-inverso bond (—NHCO—), a methyleneoxy bond (—CH$_2$—O—), a thiomethylene bond (—CH$_2$—S—), a carba bond (—CH$_2$—CH$_2$—), a ketomethylene bond (—CO—CH$_2$—), a hydroxyethylene bond (—CHOH—CH$_2$—), a (—N—N—) bond, an E-alkene bond or a (—CH=CH—) bond. Namely, the inventors have shown that using a reduced bond (—CH$_2$—NH—) makes it possible to significantly increase resistance to at least one protease. Advantageously, ψ therefore represents a reduced bond (—CH$_2$NH—).

Although only the ψ between $Y_1$ and Z (if i=1) or $Y_1$ and $Y_2$ (if i=0) is systematically present in compounds of formula (I), it is also possible that other peptide bonds of the pseudopeptide units may be modified as described earlier. In particular, in the context of the invention, the bonds between the amino acids which are not specified can equally well be standard peptide bonds or modified ψ bonds as described earlier. The presence of additional ψ bonds may make it possible to further increase resistance to proteases of compounds of formula (I). Nevertheless, the increase linked to the presence of the first Y bond between $Y_1$ and Z (if i=1) or $Y_1$ and $Y_2$ (if i=0) is already highly significant and the addition of other ψ bonds complicates synthesis of the pseudopeptide units and therefore of compounds of formula (I). The presence of additional ψ bonds is therefore possible but optional.

Figure 2A:
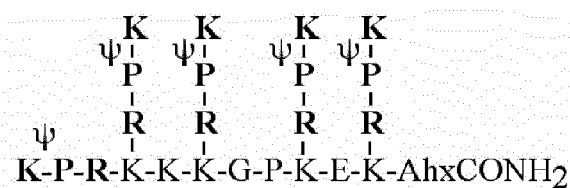
FIG. 2. A. Structure of compound HB19. B. Structure of trivalent compound Nucant 01 with a cyclic hexapeptide consisting of alternating alanine residues (A) of configuration D and lysine residues (K) of configuration L as the support. Three pseudopeptide units KψPR (with ψ=CH$_2$—N) are covalently bound to the ε amino group of each of the lysine residues. C. Structure of pentavalent compound Nucant 2 (SEQ ID NO:20) with a linear peptide as a support having a helicoidal structure of sequence SEQ ID NO:18 in which 5 pseudopeptide units KψPR (with ψ=CH$_2$—N) are covalently bound to the ε amino group of each of the 5 lysine residues, Ac represents a CH$_3$—CO— group. D. Structure pentavalent compound Nucant 3 (SEQ ID NO:21) with a linear peptide as a support having a helicoidal structure of sequence SEQ ID NO:19 in which 5 pseudopeptide units KψPR (with ψ=CH$_2$—N) are covalently bound to the ε amino group of each of the 5 lysine residues, Ac represents a CH$_3$—CO— group. E. Structure of pentavalent compound Nucant 4 with a support comprising 5 lysine residues linked by amide bonds at the ε amino group of each Lysine residue, to which 5 pseudopeptide units KψPR (with ψ=CH$_2$—N) are covalently bound to the alpha-carbon amino group of each of the 5 lysine residues. F. Structure of hexavalent compound Nucant 6 (SEQ ID NO:16) with a linear peptide as a support having a helicoidal structure of sequence SEQ ID NO:15 in which 5 pseudopeptide units KψPR (with ψ=CH$_2$—N) are covalently bound to the ε amino group of each of the 6 lysine residues, Ac represents a CH$_3$—CO— group. G. Structure of hexavalent compound Nucant 7 (SEQ ID NO:17) with a linear peptide as a support having a helicoidal structure of sequence SEQ ID NO:13 in which 6 pseudopeptide units KψPR (with ψ=CH$_2$—N) are covalently bound to the ε amino group of each of the 6 lysine residues, Ac represents a CH$_3$—CO— group. H. Structure of quadrivalent compound Nucant 8 (SEQ ID NO:23) with a support made of a linear peptide having a helicoidal structure (SEQ ID NO:22, comprising 4 Lys-Aib-Gly (SEQ ID NO: 7) units), to which 4 pseudopeptide units KψPR (with ψ=CH$_2$—N) are covalently bound to the ε amino group of each of the 4 lysine residues. I. Structure of octavalent compound Nucant 9 (SEQ ID NO:25) with a support made of a linear peptide having a helicoidal structure (SEQ ID NO:24, comprising 4 Lys-Aib-Gly (SEQ ID NO: 7) units), to which 8 pseudopeptide units KψPR (with ψ=CH$_2$—N) are covalently bound to the ε amino group of each of the 8 lysine residues.

Examples of compounds that can be used in the invention include in particular the compounds (see FIG. 2 and Examples):

HB19 (FIG. 2A, SEQ ID NO: 5, a compound which has as a support a linear peptide of SEQ ID NO:4 in which the 5 pseudopeptide units KψPR (with ψ=CH$_2$—N) are covalently bound to the ε amino group of each of the 5 lysine residues), Nucant 01 (FIG. 2B), a compound which has a support a cyclic hexapeptide consisting of alternating alanine residues (A) of configuration D and lysine residue (K) of configuration L, where the 3 pseudopeptide units KψPR (with ψ=CH$_2$—N) are covalently bound to the ε amino group of each of the 3 lysine residues (K); see FIG. 2B), Nucant 2 (FIG. 2C, SEQ ID NO: 20, a compound which has as a support a linear peptide with a helicoidal structure of sequence SEQ ID NO:18 in which 5 pseudopeptide units KψPR (with ψ=CH$_2$—N) are covalently bound to the ε amino group of each of the 5 lysine residues), Nucant 3 (FIG. 2D, SEQ ID NO: 21, a compound which has as a support a linear peptide with a helicoidal structure of sequence SEQ ID NO:19 in which 5 pseudopeptides KψPR (with ψ=CH$_2$—N) are covalently bound to the ε amino group of each of the 5 lysine residues), Nucant 4 (FIG. 2E, a compound having a support comprising 5 lysine residues linked by amide bonds at the ε amino group of each Lysine residue, to which 5 pseudopeptide units KψPR (with ψ=CH$_2$—N) are covalently bound to the alpha-carbon amino group of each of the 5 lysine residues), Nucant 6 (FIG. 2F, SEQ ID NO: 16, a compound which has as a support a linear peptide with a helicoidal structure of sequence SEQ ID NO:15 in which 6 pseudopeptide units KψPR (with ψ=CH$_2$—N) are covalently bound to the ε amino group of each of the 6 lysine residues), Nucant 7 (FIG. 2G, SEQ ID NO: 17, a compound which has a support a linear peptide of sequence SEQ ID NO:13 in which 6 pseudopeptide units KψPR (with ψ=CH₂—N) are covalently bound to the ε amino group of each of the 6 lysine residues), Nucant 8 (FIG. 2H, SEQ ID NO:23, a compound which has as a support a linear peptide with a helicoidal structure (SEQ ID NO:22) comprising 4 units of sequence Lys-Aib-Gly (SEQ ID NO:7), to which 4 pseudopeptides KψPR (with ψ=CH₂—N) are covalently bound to the ε amino group of each of the 4 lysine residues), and Nucant 9 (FIG. 2I, SEQ ID NO:25, a compound which has as a support a linear peptide with a helicoidal structure (SEQ ID NO:24) comprising 8 units of sequence Lys-Aib-Gly (SEQ ID NO:7), to which 8 pseudopeptides KψPR (with ψ=CH₂—N) are covalently bound to the ε amino group of each of the 8 lysine residues).

In one embodiment, the Nucant provided by the invention is a pseudopeptide bearing one or more KψPR tripeptides on a template structure, and includes, for example, compound HB19 and Nucant peptides 1-4, and 6-9 of FIG. 2. The tripeptides can be linked to the template through a linker sequence comprising 1 to 6 residues.

In certain embodiments, the Nucant peptide comprised in compositions of the invention comprises or consists of a pentavalent peptide having Formula III (herein, "HB-19", corresponding to FIG. 2A):

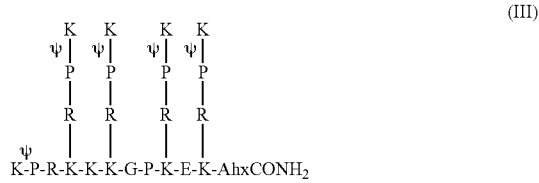

(III)

The general formula of the HB-19 pseudopeptide is also referred to herein by the following: 5[Kψ(CH₂N)PR]-TASP, wherein Ψ represents a reduced peptide bond (i.e., CH₂N). HB-19 is the prototype of the Nucant family; it is a specific ligand for surface nucleolin. HB-19 is a pentavalent construct of a tripeptide KψPR supported by a polylysin matrix. For a detailed discussion of the HB-19 peptide see: Nisole et al., *AIDS Res. Hum. Retroviruses,* 2000 Feb. 10; 16(3): 237-49; Nisole et al., *J. Biol. Chem.,* 2002 Jun. 7; 277(23) 20877-86; Nisole et al., *J. Biol. Chem.,* 1999 Sep. 24; 274(39):27875-84; Krust et al., *PNAS,* 2001 Nov. 20; 98(24):14090-095; Alete et al., *FEBS J.,* 2006; 273:4668-81; which are hereby incorporated herein by reference in their entirety for all purposes.

Located essentially in the nucleus of normal cells where it is protected, nucleolin is, however, abundant at the surface of the cells which are proliferating as well as that of active endothelial cells where it can be a target for the Nucants as described herein and their derivatives, and congeners, which binds with specificity to surface nucleolin and/or glycoaminoglycans (GAGs).

Other exemplary members of the Nucant family differ by the matrix structure. Examples are displayed in FIG. 2B to 2I.

For example, in a preferred embodiment the invention, the Nucant peptide comprised in compositions of the invention comprises or consists of Nucant 6L ("N6L", see FIG. 2F).

The Nucant compounds present in the compositions of the invention may or may not be optically pure, which means that the lysine residues in the pseudopeptide units may either be in random L or D configuration (not optically pure), or be all in D configuration or all in L configuration (optically pure). Advantageously, Nucant compounds comprised in compositions of the invention are optically pure, i.e. the lysine residues in the pseudopeptide units are all in D configuration or all in L configuration, preferably all in L configuration. Such optically pure Nucant compounds can be obtained by the method described in WO2009/141687.

Immunochemical assays useful for practicing methods of the invention are well known to those skilled in the art, as described, for example, in Klug, T. L. et al, Cancer Res., 44:1048 (1984), Herlyn, M. et al, J. Clin. Immunol., 2:135 (1982), Metzgar, R. S. et al, Proc. Natl. Acad. Sci., USA. 81:5242 (1984), Papsidero, L. D. et al, Cancer Res., 44:4653 (1984), Hayes, D. F. et al, J. Clin. Invest., 75:1671 (1985), Killian, C. S. et al, J. Natl. Cancer Inst., 76:179 (1986), Killian, C. S. et al, Cancer Res., 45:886 (1985), Hedin, A. et al, Proc. Natl. Acad. Sci., USA. 80:3470 (1983), Pekary, A. E. et al, Clin. Chem., 30:1213-1215 (1984), Bast, R. C. et al, New England J. Med., 309:883-887 (1983) and Bellet, D. H. et al, Proc. Natl. Acad. Sci., USA, 81:3869-3873 (1984), all of which are specifically incorporated herein by reference.

An advantage of Nucant peptides is that they demonstrate dual activity; they are capable of blocking independently both tumor proliferation and angiogenesis. None of the current products on the market exhibit this dual activity. Another major advantage of the present Nucant-drug conjugate is that is demonstrates an excellent safety profile. Additionally, because of its small size the Nucant peptide is not immunogenic and manufacturing and cost goods will be at a reasonable level.

The Nucants as described herein bind surface nucleolin, which is present in active endothelial cells responsible for angiogenesis as well as in cancer cells, in a quasi irreversible manner. Nucants have shown a binary effect: direct blockade of the growth of tumor cells and inhibition of the angiogenesis which led to the complete eradication of implanted tumor in animal models. The specific binding occurs with the RGG domain located in the C-terminal region of the protein. After interaction the complex is internalized rapidly through a temperature dependent mechanism. Nucants can be considered as a stable and irreversible ligand of the surface nucleolin. After internalization the Nucant remains in the cytoplasm and does not cross the nuclear membrane.

As used herein, the term "Nucant" also encompasses peptides having minor modifications, for example, conservative amino acid modifications, chemical modification to mimic valence properties, and modifications that serve to increase its stability, solubility, biouptake and/or bioavailability; for example, absorption from the gut or penetration through the blood-brain barrier (BBB). For a review of strategies for increasing bioavailability of peptides and peptide drugs in the brain, and of methods for determining the permeability of peptides through the BBB using in vitro and in vivo assays, see Engleton et al., *Peptides* 9:1431-1439 (1997), the teachings of which are incorporated herein by reference. A pharmaceutically acceptable carrier can contain physiologically acceptable compounds that include carbohydrates such as glucose, sucrose or dextrans; antioxidants, such as ascorbic acid or glutathione; chelating agents; and low molecular weight proteins. Additional modifications to a Nucant peptide that can increase its bioavailability include conjugating the peptide to a lipophilic moiety, such as a lipophilic amino acid or compound.

The term "Nucant" is further intended to encompass pseudopeptides bearing one or more KψPR tripeptide or KψPRR tetrapeptide on a template structure, and which have one or several minor modifications to the Nucant sequence. Contemplated modifications include chemical or enzymatic modifications (e.g. acylation, phosphorylation, glycosylation, etc.), and substitutions of one or several amino acids to the Nucant sequence. Those skilled in the art recognize that such modifications can be desirable in order to enhance the bioactivity, bioavailability or stability of the peptide, or to facilitate its synthesis or purification.

In an additional embodiment, the Nucant described herein can be conjugated to one or more of a carrier, a diagnostic agent or a cytotoxic agent, either directly or indirectly, e.g., via a linker moiety. Alternatively, the cytotoxic agent may be covalently bound to a linker moiety, which is in turn covalently bound to the carrier. A linker moiety can be, for example, amino acid (including mimetics, analogs, and derivatives), a peptide or polypeptide (including mimetics, analogs, and derivatives), a sterically labile compound, lipid, aliphatic group, carbohydrate, glyceride, a nucleotide or nucleic acid, peptide nucleic acid, nucleic acid derivative, and the like. An example of a conjugate in which Nucant 6L is conjugated to cytotoxic drug 5-fluoro-uracyl ("5-FU") is shown below:

function of the Nucant. Furthermore, non-linear variants of the Nucant sequence, including branched sequences and cyclic sequences, and variants that contain one or more D-amino acid residues in place of their L-amino acid counterparts, may be made.

In additional embodiments, the Nucant carrier can be incorporated into liposomes (Gregoriadis, *Liposome Technology*, Vols. I to III, 2nd ed. (CRC Press, Boca Raton Fla. (1993)). Liposomes, which consist of phospholipids or other lipids, are nontoxic, physiologically acceptable and metabolizable carriers that are relatively simple to make and administer. In still further embodiments, the Nucant carrier can be prepared as nanoparticles. Adsorbing peptide compounds onto the surface of nanoparticles has proven effective in delivering peptide drugs to the brain (see Kreuter et al., *Brain Res.* 674:171-174 (1995)). Exemplary nanoparticles are colloidal polymer particles of poly-butylcyanoacrylate with HB-19P adsorbed onto the surface and then coated with polysorbate 80.

Those skilled in the art can determine which residues and which regions of the Nucant sequence are likely to be KψPR   KψPR   KψPR   KψPR   KψPR   KψPR
  |      |      |      |      |      |
Ac-K-Aib-G-K-Aib-G-K-Aib-G-K-Aib-G-K-Aib-G-K-Aib-G-C(5FU)-CONH$_2$ Aib = α-amino isobutyric acid Contemplated amino acid substitutions to the Nucants provided by the invention, e.g., Nucant peptides, include conservative changes, wherein a substituted amino acid has similar structural or chemical properties (e.g., replacement of an apolar amino acid with another apolar amino acid; replacement of a charged amino acid with a similarly charged amino acid, etc.). Those skilled in the art also recognize that nonconservative changes (e.g., replacement of an uncharged polar amino acid with an apolar amino acid; replacement of a charged amino acid with an uncharged polar amino acid, etc.) can be made without affecting the tolerant of modification and still retain the ability to bind nucleolin with clinically relevant affinity. For example, amino acid substitutions, or chemical or enzymatic modifications, at residues that are less well conserved between species are more likely to be tolerated than substitutions at highly conserved residues. Therefore, in certain embodiments the carrier may be modified so that the modified version of the carrier may be more easily conjugated to a diagnostic agent.

The Nucant peptides described herein can be produced using well known recombinant methods or via well known synthetic methods. There are several well known methods for performing peptide synthesis including liquid-phase and solid-phase synthesis. Detailed discussions of various methods can be found at, for example, Atherton, E.; Sheppard, R. C. (1989). *Solid Phase peptide synthesis: a practical approach*. Oxford, England: IRL Press; Stewart, J. M.; Young, J. D. (1984). *Solid phase peptide synthesis*, 2nd edition, Rockford: Pierce Chemical Company, 91; R. B. Merrifield (1963). "Solid Phase Peptide Synthesis. I. The Synthesis of a Tetrapeptide". *J. Am. Chem. Soc.* 85 (14): 2149-2154; L. A. Carpino (1993). "1-Hydroxy-7-azabenzotriazole. An efficient peptide coupling additive". *J. Am. Chem. Soc.* 115 (10): 4397-4398; which are hereby incorporated by reference in their entirety for all purposes.

The most abundant heteropolysaccharides in the body are the glycosaminoglycans (GAGs). These molecules are long unbranched polysaccharides containing repeating disaccharide units. The disaccharide units contain either of two modified sugars, N-acetylgalactosamine (GalNAc) or N-acetylglucosamine (GlcNAc), and an uronic acid such as glucuronate or iduronate. GAGs are highly negatively charged molecules, with extended conformation that imparts high viscosity to the solution. GAGs are located primarily on the surface of cells or in the extracellular matrix (ECM). Along with the high viscosity of GAGs comes low compressibility, which makes these molecules ideal for a lubricating fluid in the joints. At the same time, their rigidity provides structural integrity to cells and provides passageways between cells, allowing for cell migration. The specific GAGs of physiological significance are hyaluronic acid, dermatan sulfate, chondroitin sulfate, heparin, heparan sulfate, and keratan sulfate. Although each of these GAGs has a predominant disaccharide component (see Table I below), heterogeneity does exist in the sugars present in the make-up of any given class of GAG.

Some examples of glycosaminoglycan uses in nature include heparin as an anticoagulant, hyaluronan as a component in the synovial fluid lubricant in body joints, and chondroitins, which can be found in connective tissues, cartilage, and tendons. Members of the glycosaminoglycan family vary in the type of hexosamine, hexose or hexuronic acid unit they contain (e.g. glucuronic acid, iduronic acid, galactose, galactosamine, glucosamine) (Table I) They also vary in the geometry of the glycosidic linkage.

According to the present invention, a GAG present in the composition may be natural or synthetic. By "natural", it is intended to mean that the GAG may be isolated from natural sources, although it may also be obtained by chemical or biochemical synthesis. In contrast, by "synthetic", it is intended to mean that said GAG does not exist in nature and may only be obtained by chemical or biochemical synthesis. In addition, the GAG chain may further have been modified by addition of various substituents.

Examples of natural GAGs are described in following Table I:

TABLE I

Structure of several natural GAGs.

| Name | Hexuronic acid/ Hexose | Hexosamine | Linkage geometry between predominant monomeric units | Unique features |
|---|---|---|---|---|
| Chondroitin sulfate | GlcUA or GlcUA(2S) | GalNAc or GalNAc(4S) or GalNAc(6S) or GalNAc(4S,6S) | -4GlcUAβ1-3GalNAcβ1- | Most prevalent GAG |
| Dermatan sulfate (formerly known as Chondroitin sulfate B) | GlcUA or IdoUA or IdoUA(2S) | GalNAc or GalNAc(4S) or GalNAc(6S) or GalNAc(4S,6S) | -4IdoUAβ1-3GalNAcβ1- | Distinguished from chondroitin sulfate by the presence of iduronic acid, although some hexuronic acid monosaccharides may be glucuronic acid. |
| Keratan sulfate | Gal or Gal(6S) | GlcNAc or GlcNAc(6S) | -3Gal(6S)β1-4GlcNAc(6S)β1- | Keratan sulfate type II may be fucosylated. |
| Heparin | GlcUA or IdoUA(2S) | GlcNAc or GlcNS or GlcNAc(6S) or GlcNS(6S) | -4IdoUA(2S)α1-4GlcNS(6S)α1- | Highest negative charge density of any known biological molecule |
| Heparan sulfate | GlcUA or IdoUA or IdoUA(2S) | GlcNAc or GlcNS or GlcNAc(6S) or GlcNS(6S) | -4GlcUAβ1-4GlcNAcα1- | Highly similar in structure to heparin, however heparan sulfates disaccharide units are organised into distinct sulfated and non-sulfated domains. |
| Hyaluronan | GlcUA | GlcNAc | -4GlcUAβ1-3GlcNAcβ1- | The only GAG that is exclusively non-sulfated |

GlcUA: β-D-glucuronic acid;
GlcUA(2S) = 2-O-sulfo-β-D-glucuronic acid;
IdoUA = α-L-iduronic acid;
IdoUA(2S) = 2-O-sulfo-α-L-iduronic acid;
Gal = β-D-galactose;
Gal(6S) = 6-O-sulfo-β-D-galactose;
GalNAc = β-D-N-acetylgalactosamine;
GalNAc(4S) = β-D-N-acetylgalactosamine-4-O-sulfate;
GalNAc(6S) = β-D-N-acetylgalactosamine-6-O-sulfate;
GalNAc(4S,6S) = β-D-N-acetylgalactosamine-4-O, 6-O-sulfate;
GlcNAc = α-D-N-acetylglucosamine;
GlcNS = α-D-N-sulfoglucosamine;
GlcNS(6S) = α-D-N-sulfoglucosamine-6-O-sulfate.

In Table I above, "Chondroitin sulfate" refers to several distinct GAGs, depending on the site(s) of sulfation, as described in Table II below:

TABLE II

Various types of condroitin sulfate depending on the site(s) of sulfation

| Letter identification | Site of sulfation | Systematic name |
| --- | --- | --- |
| Chondroitin sulfate A | carbon 4 of the N-acetylgalactosamine (GalNAc) sugar | chondroitin-4-sulfate |
| Chondroitin sulfate C | carbon 6 of the GalNAc sugar | chondroitin-6-sulfate |
| Chondroitin sulfate D | carbon 2 of the glucuronic acid and 6 of the GalNAc sugar | chondroitin-2,6-sulfate |
| Chondroitin sulfate E | carbons 4 and 6 of the GalNAc sugar | chondroitin-4,6-sulfate |

"Chondroitin sulfate B" is an old name for dermatan sulfate, which is however no longer classified as a form of chondroitin sulfate.

The majority of GAGs in the body are linked to core proteins, forming proteoglycans (also called mucopolysaccharides). The GAGs extend perpendicularly from the core in a brush-like structure. The linkage of GAGs to the protein core involves a specific trisaccharide composed of two galactose residues and a xylose residue (GAG-GalGalXyl-O—$CH_2$-protein). The trisaccharide linker is coupled to the protein core through an O-glycosidic bond to a S residue in the protein. Some forms of keratan sulfates are linked to the protein core through an N-asparaginyl bond. The protein cores of proteoglycans are rich in S and T residues, which allows multiple GAG attachments.

In any of the embodiments of the compositions or methods described herein, the Nucant provided by the invention can be admixed or complexed with a GAG, wherein the GAG is at least one of Chondroitin sulfate, Dermatan sulfate, Keratan sulfate, Heparin, Heparan sulfate, Hyaluronan or a combination thereof.

Advantageously, in compositions or methods according to the invention described herein, the GAG is selected from Chondroitin sulfate, Dermatan sulfate, Keratan sulfate, Heparin, or a combination thereof. More preferably, in compositions or methods according to the invention described herein, the GAG is selected from Heparin, Chondroitin sulfate (in particular Chondroitin sulfate A or C,), and Dermatan sulfate (also known as Chondroitin sulfate B), or a combination thereof. Indeed, particularly advantageous results have been obtained using these particular GAGs, while results obtained with Heparan sulfate and Hyaluronan are less advantageous (see Example 1).

Particularly preferred compositions of the invention comprise one Nucant compound selected from HB19 (preferably HB19L or HB19D), Nucant 1 (preferably Nucant 1L or Nucant 1D), Nucant 2 (preferably Nucant 2L or Nucant 2D), Nucant 3 (preferably Nucant 3L or Nucant 3D), Nucant 6 (preferably Nucant6L or Nucant 6D, more preferably Nucant6L), Nucant 7 (preferably Nucant 7L or Nucant 7D), Nucant 8 (preferably Nucant 8L or Nucant 8D) and Nucant 9 (preferably Nucant 9L or Nucant 9D) in combination with heparin, chondroitin sulfate (in particular chondroitin sulfate A or C) and/or dermatan sulfate (also known as chondroitin sulfate B). Particularly preferred compositions of the invention comprise HB19 or Nucant 6L (N6L) in combination with, chondroitin sulfate (in particular chondroitin sulfate A or C) and/or dermatan sulfate (also known as chondroitin sulfate B). Examples of preferred compositions thus include:

HB19 and heparin,
HB19 and chondroitin sulfate A,
HB19 and dermatan sulfate (also known as chondroitin sulfate B),
HB19 and chondroitin sulfate C,
N6L and heparin,
N6L and chondroitin sulfate A,
N6L and dermatan sulfate (also known as chondroitin sulfate B),
N6L and chondroitin sulfate C.

In compositions of the invention, Nucant concentration is preferably at least 1 μM, preferably at least 2.5 μM, in order to ensure potentialization of its properties by GAGs.

In certain embodiments, the therapeutic composition provided by the invention comprises a combination of a Nucant and a GAG, wherein the molar ratio of Nucant to GAG varies from 1:1000 to 1000:1, and encompasses all ratios therebetween.

The inventors have found that, in particular at low Nucant concentrations, a range of weight ratio of Nucant to GAG in the composition should be respected to guaranty potentialization of Nucant properties by GAGs. Thus, advantageously, in compositions according to the invention, the weight ratio of Nucant to GAG is at most 24, preferably at most 20, preferably at most 15, preferably at most 14, preferably at most 13, preferably at most 12, preferably at most 11, preferably at most 10, preferably at most 9, preferably at most 8. In compositions of the invention, the weight ratio of Nucant to GAG is also advantageously at least 0.01, at least 0.05, at least 0.08, preferably at least 0.1, preferably at least 0.2, preferably at least 0.3, preferably at least 0.4, preferably at least 0.5, preferably at least 0.6, preferably at least 0.7, preferably at least 0.8, preferably at least 0.9, preferably at least 1. In advantageous embodiments of compositions according to the invention, the weight ratio of Nucant to GAG is between 0.01 and 24, between 0.05 and 20, between 0.1 and 15, between 0.1 and 10, between 0.1 and 8, between 0.2 and 8, between 0.3 and 8, between 0.4 and 8, between 0.5 and 8, between 0.6 and 8, between 0.7 and 8, between 0.8 and 8, between 0.9 and 8, between 1 and 8.

The lowest the Nucant concentration in the composition, the more important is the fact that the weight ratio of Nucant to GAG is comprised in above mentioned ranges.

For compound Nucant 6L (N6L), optimal ranges of the weight ratio of N6L to GAG have been determined depending on N6L concentration in the composition (see Example 2)

N6L at 5 μM (corresponding to 20 μg/ml): weight ratio N6L/GAG between 0.2 and 2,
N6L at 20 μM (corresponding to 80 μg/ml): weight ratio N6L/GAG between 0.8 and 8.

In a composition of the invention comprising microspheres of a Nucant and a GAG, the Nucant/GAG microspheres advantageously have a diameter of less than 5 mm; or from about 1 nm to about 1 mm; or from about 1 nm to about 10 μm; or from about 10 nm to about 500 nm.

In any of the compositions described herein, the therapeutic compositions provided by the invention optionally includes a pharmaceutically acceptable carrier, excipient or adjuvant.

The invention also provides methods for the manufacture of a composition comprising microspheres of a Nucant and a GAG, comprising admixing a Nucant and a GAG in amounts sufficient to create a microsphere or plurality of microspheres. Preferably, Nucant and GAG are admixed in a weight ratio comprised in ranges described above.

In another aspect, the invention provides compositions as described herein and methods, for treating and/or preventing a disease or disorder related to the detrimental growth and/or proliferation of a cell, e.g., a cancer cell.

Any composition of the invention as described herein may thus be for use in the treatment and/or prevention of a disease or disorder related to the detrimental growth and/or proliferation of a cell, e.g., a cancer cell. The invention also relates to the use of any composition of the invention as described herein for the manufacture of a medicament for treating and/or preventing a disease or disorder related to the detrimental growth and/or proliferation of a cell, e.g., a cancer cell.

In certain embodiments, the method comprises administering a composition comprising an effective amount of a Nucant and a GAG, as described herein, to a subject, in vivo, ex vivo, or in vitro, wherein the composition is effective in inhibiting or preventing the growth and/or proliferation of a cancer cell.

Indeed, Nucant compounds are known from WO2007/125210 to be useful for the treatment of a disease involving deregulation of cell proliferation and/or angiogenesis.

The term "disease involving deregulation of cell proliferation and/or angiogenesis" means, in the context of the invention, any human or animal disease affecting one or more organs in which one or more abnormal cell proliferation phenomena are observed, as well as groups of cells or tissues and/or abnormal neovascularisation. Evidently, such diseases include all types of cancer, such as adenoma, sarcoma, carcinoma, lymphoma, and especially cancer of the ovary, breast, pancreas, lymphatic ganglion, skin, blood, lung, brain, kidney, liver, nasopharyngeal cavity, thyroid, central nervous system, prostate, colon, rectum, uterine neck, testicles or bladder. They also include non-cancerous diseases of the skin such as epidermal or dermal cysts, psoriasis, angiomas, as well as ocular diseases such as age related macular degeneration (ARMD), diabetic retinopathy or neovascular glaucoma. Neurodegenerative diseases such as multiple sclerosis, Parkinson's and Alzheimer's or autoimmune diseases such as lupus or rheumatoid polyarthritis, as well as diseases related to atherosclerosis.

Any composition of the invention as described herein may thus be for use in the treatment of disease involving deregulation of cell proliferation and/or angiogenesis. The present invention also relates to the use of a composition of the invention as described herein for the manufacture of a medicament for the treatment of disease involving deregulation of cell proliferation and/or angiogenesis.

Indeed, as demonstrated in FIGS. 3-6 and 9-19, the anti-cancer potency, in fact anti-proliferative potency on cancer cells, of multivalent Nucants provided by the invention is enhanced by the incorporation of the Nucants into microspheres with GAGs.

The invention thus also provides compositions of the inventions and methods, for treating and/or preventing a disease or disorder related to the growth and/or proliferation of a cancer cell in an individual.

Any composition of the invention as described herein may thus be for use in the treatment and/or prevention of a disease or disorder related to the growth and/or proliferation of a cancer cell in an individual, in particular for the treatment and/or prevention of cancer. The invention also relates to the use of a composition of the invention as described herein for the preparation of a medicament for the treatment and/or prevention of a disease or disorder related to the growth and/or proliferation of a cancer cell in an individual, in particular for the treatment and/or prevention of cancer.

The methods comprise administering a composition comprising an effective amount of a Nucant and a GAG as described herein, or a composition comprising microspheres of a Nucant and a GAG as described herein, to an individual, wherein the composition is effective in inhibiting or preventing the growth and/or proliferation the cancer cell.

As indicated in Background section, Nucant compounds have been shown to bind surface nucleolin RGG domain. Moreover, it has also been shown that surface nucleolin is expressed at the surface of tumour cells, such as tumour cells derived from hepatic carcinoma (Semenkovich, C. F., Ostlund, R. E. J., Olson, M. O., and Yang, J. W. A protein partially expressed on the surface of HepG2 cells that binds lipoproteins specifically is nucleolin. (1990) Biochemistry 29, 9708-9713), T-lymphocyte leukaemia (Callebaut, C., Jacotot, E., Krust, B., Guichar, G., Blanco, J., Svab, J., Muller, S., Briand, J. P., and Hovanessian, A. G. Composé TASP inhibitors of HIV entry bind specifically to a 95-kDa cell surface protein. (1997) J. Biol. Chem. 272, 7159-7166; and Callebaut, C., Blanco, J., Benkirane, N., Krust, B., Jacotot, E., Guichard, G., Seddiki, N., Svab, J., Dam, E., Muller, S., Briand, J. P., and Hovanessian, A. G. Identification of V3 loop-binding proteins as potential receptors implicated in the binding of HIV particles to CD4(+) cells. (1998) J. Biol. Chem. 273, 21988-2199) and uterine cancer cells (Callebaut, C., Jacotot, E., Krust, B., Guichar, G., Blanco, J., Svab, J., Muller, S., Briand, J. P., and Hovanessian, A. G. Composé TASP inhibitors of HIV entry bind specifically to a 95-kDa cell surface protein. (1997) J. Biol. Chem. 272, 7159-7166), as well as at the surface of activated endothelial cells (Christian, S., Pilch, J., Akerman, M. E., Porkka, K., Laakkonen, P., and Ruoslahti, E. Nucleolin expressed at the cell surface is a marker of endothelial cells in angiogenic blood vessels. (2003) J. Cell Biol. 163, 871-878), cells which are involved in the angiogenesis process. Because the binding of the Nucants described herein to nucleolin is a generalized effect, the Nucant-containing compositions provided by the invention would be suitable for treating any known cancer. For example, types of cancer suitable for treatment with the compositions and methods provided by the invention include, Acute Lymphoblastic Leukemia; Acute Myeloid Leukemia; Adrenocortical Carcinoma; Adrenocortical Carcinoma; AIDS-Related Cancers; AIDS-Related Lymphoma; Anal Cancer; Appendix Cancer; Astrocytomas; Atypical Teratoid/Rhabdoid Tumor; Basal Cell Carcinoma; Bile Duct Cancer, Extrahepatic; Bladder Cancer; Bone Cancer, Osteosarcoma and Malignant Fibrous Histiocytoma; Brain Stem Glioma; Brain Tumor; Embryonal Tumors; Astrocytomas; Craniopharyngioma; Ependymoblastoma; Medulloepithelioma; Pineal Parenchymal Tumors of Intermediate Differentiation; Supratentorial Primitive Neuroectodermal Tumors and Pineoblastoma; Brain and Spinal Cord Tumors; Breast Cancer; Bronchial Tumors; Burkitt Lymphoma; Carcinoid Tumors; Cervical Cancer; Childhood Cancers; Chordoma; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Endometrial Cancer Ependymoblastoma; Ependymoma; Esophageal Cancer; Esthesioneuroblastoma; Ewing Sarcoma Family of Tumors; Extracranial Germ Cell Tumor; Extragonadal Germ Cell Tumor; Extrahepatic Bile Duct Cancer; Eye Cancer; Intraocular Melanoma; Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Hairy Cell Leukemia; Head and Neck Cancer; Heart Cancer; Hepatocellular (Liver) Cancer; Histiocytosis, Langerhans Cell; Hodgkin Lymphoma; Hodgkin Lymphoma, Childhood; Hypopharyngeal Cancer; Intraocular Melanoma; Islet Cell Tumors (Endocrine Pancreas); Kaposi Sarcoma; Kidney (Renal Cell) Cancer; Langerhans Cell Histiocytosis; Laryngeal Cancer; Laryngeal Cancer, Childhood; Lip and Oral Cavity Cancer; Lung Cancer, Non-Small Cell; Lung Cancer, Small Cell; Non-Hodgkin Lymphoma; Macroglobulinemia, Waldenström; Malignant Fibrous Histiocytoma of Bone and Osteosarcoma; Medulloblastoma; Medulloepithelioma; Melanoma; Merkel Cell Carcinoma; Mesothelioma; Metastatic Squamous Neck Cancer; Mouth Cancer; Multiple Endocrine Neoplasia Syndromes; Multiple Myeloma/Plasma Cell Neoplasm; Mycosis Fungoides; Myelodysplastic Syndromes; Myelodysplastic/Myeloproliferative Neoplasms; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oropharyngeal Cancer; Osteosarcoma and Malignant Fibrous Histiocytoma of Bone; Ovarian Cancer; Ovarian Germ Cell Tumor; Ovarian Low Malignant Potential Tumor; Pancreatic Cancer; Papillomatosis; Paranasal Sinus and Nasal Cavity Cancer; Parathyroid Cancer; Penile Cancer; Pharyngeal Cancer; Pineal Parenchymal Tumors of Intermediate Differentiation; Pineoblastoma and Supratentorial Primitive Neuroectodermal Tumors; Pituitary Tumor Plasma Cell Neoplasm/Multiple Myeloma; Pleuropulmonary Blastoma; Prostate Cancer; Rectal Cancer; Renal Cell (Kidney) Cancer; Renal Pelvis and Ureter, Transitional Cell Cancer; Respiratory Tract Cancer with Chromosome 15 Changes; Retinoblastoma; Rhabdomyosarcoma; Salivary Gland Cancer; Sarcoma, Ewing Sarcoma Family of Tumors; Sarcoma, Kaposi; Sarcoma, Soft Tissue; Sézary Syndrome Skin Cancer (Nonmelanoma or squamous cell); Skin Cancer (Melanoma); Skin Carcinoma, Merkel Cell; Stomach (Gastric) Cancer; Supratentorial Primitive Neuroectodermal Tumors; T-Cell Lymphoma, Cutaneous, see Mycosis Fungoides and Sézary Syndrome; Testicular Cancer; Throat Cancer; Thymoma and Thymic Carcinoma; Thyroid Cancer; Transitional Cell Cancer of the Renal Pelvis and Ureter; Urethral Cancer; Uterine Cancer, Endometrial; Uterine Sarcoma; Vaginal Cancer; Vulvar Cancer; Waldenström Macroglobulinemia; and Wilms Tumor.

It has also been surprisingly and unexpectedly discovered that the Nucants as described herein form microspheres when admixed with a GAG. Therefore, in an additional aspect, the invention provides methods of treating a disease or disorder, e.g., cancer, comprising the step of administering to a subject or an individual an effective amount of a therapeutic composition comprising microspheres of a Nucant and a GAG. In certain embodiments, the microspheres are formed prior to administration. In an additional embodiment, the microspheres are formed after administration to the subject or patient, e.g., in vivo.

When used for the treatment of cancer, compositions of the invention may further comprise a cytotoxic agent, such as for instance gemcitabine.

Figure 20:
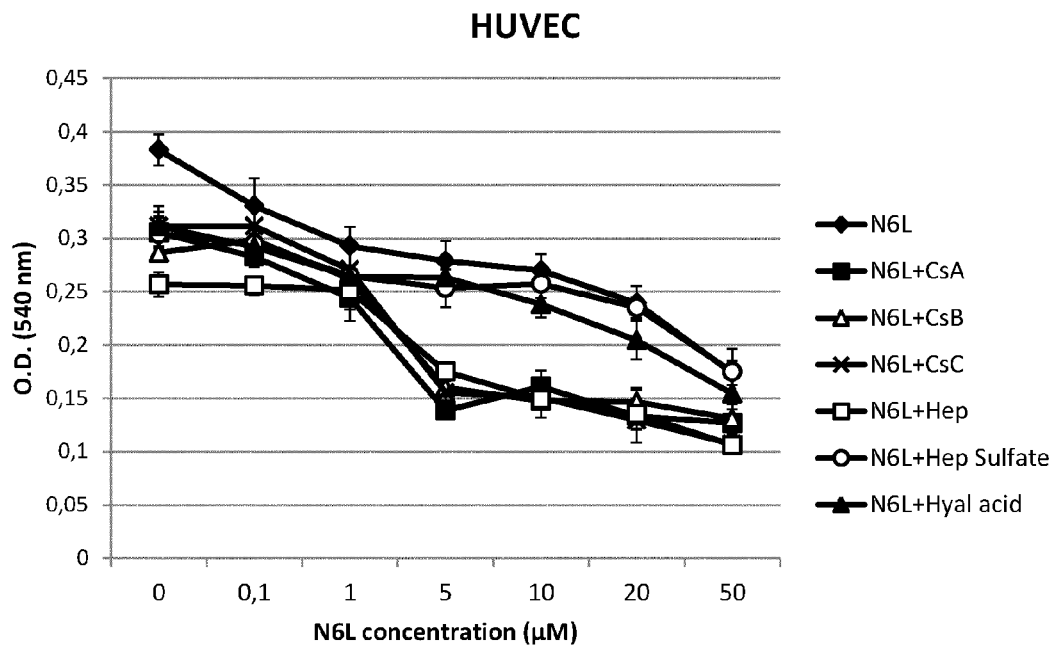
FIG. 20. Nanoparticles composed by the highly charged GAG molecules strongly inhibit proliferation of HUVEC cells, in contrast to N6L and nanoparticles composed by low charged GAG molecules that exert a slight inhibition. Similar number of HUVEC cells was treated with increasing concentrations of N6L or nanoparticles that were composed of N6L and different GAG molecules, in the presence of 5% FBS. Cells were treated every day for 4 days. At the end of the forth day, cell number was quantified using the MTT assay. We observed that N6L inhibited HUVEC proliferation in a dose dependent manner having an IC50=10 µM. However, our results showed that pre-incubation of N6L with the highly charged GAG molecules, heparin, chondroitin sulfate-A (Cs-A), chondroitin sulfate-B (Cs-B), chondroitin sulfate-C (Cs-C) resulted in the formation of nanoparticles that strongly inhibited HUVEC proliferation, having a maximal effect at a concentration of 5 µM (IC50=2.5 µM). Nanoparticles composed by higher concentrations of N6L exerted an effect similar to that of 5 µM. In contrast to the highly charged GAG molecules, N6L pre-incubation with the partially charged heparan sulfate or the uncharged hyaluronic acid did not form any nanoparticles and inhibited HUVEC proliferation in a similar manner to N6L (IC50=10 µM).
Figure 21:
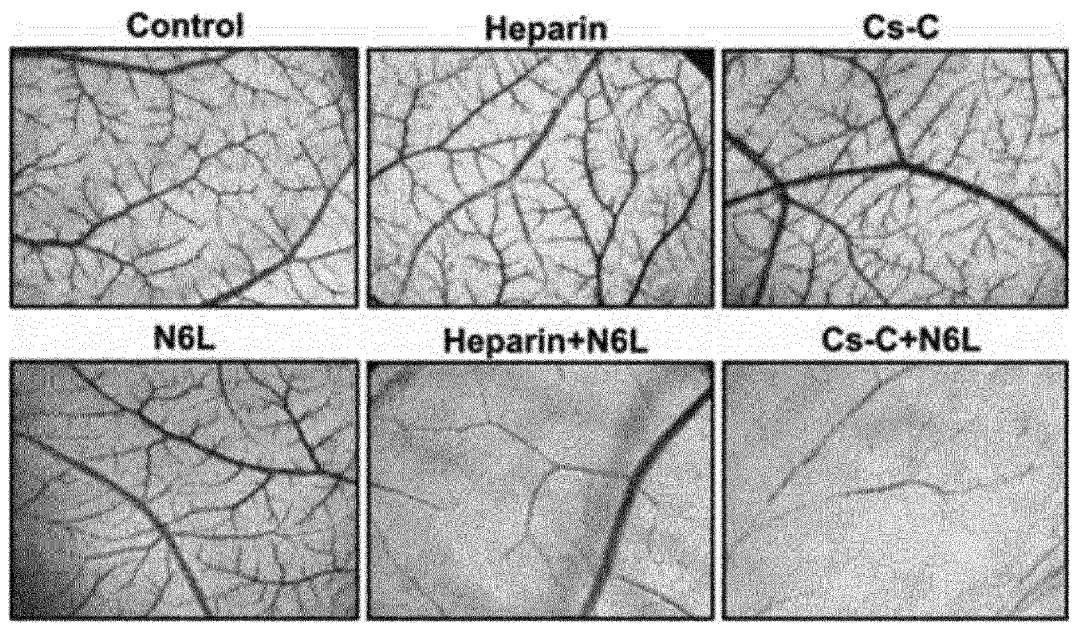
FIG. 21. Nanoparticles composed by N6L+heparin or N6L+Cs-C, but not N6L alone, strongly inhibit in vivo angiogenesis, as measured by the chicken embryo CAM assay. An 1 cm2 area of chicken embryo CAM, restricted by a silicon ring, was incubated with 20 µM N6L or nanoparticles composed by 20 µM N6L and 10 mg/ml heparin or Cs-C. 48 h later, total vessels length was quantified. We observed that N6L had no effect on the in vivo angiogenesis, in contrast to the heparin or Cs-C composed nanoparticles that inhibited the development of new blood vessels (50% and 70%, respectively). Results are mean values±SD from at least 3 independent experiments.
Figure 21:
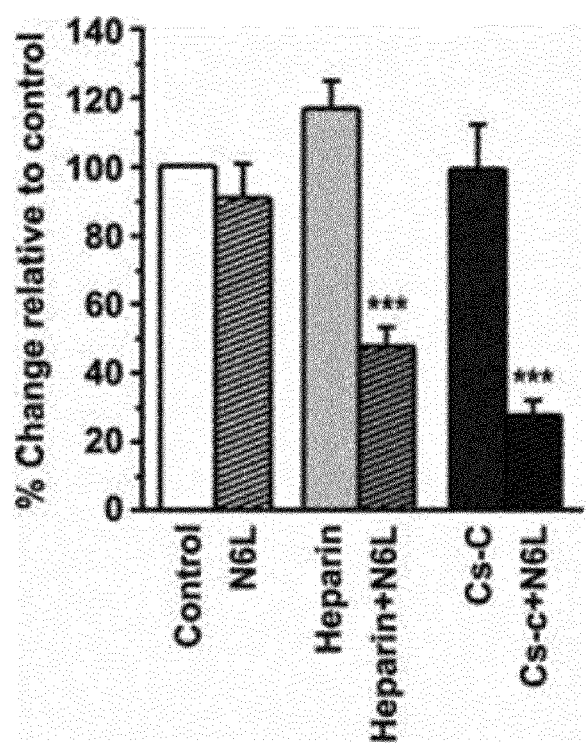
Figure 22:
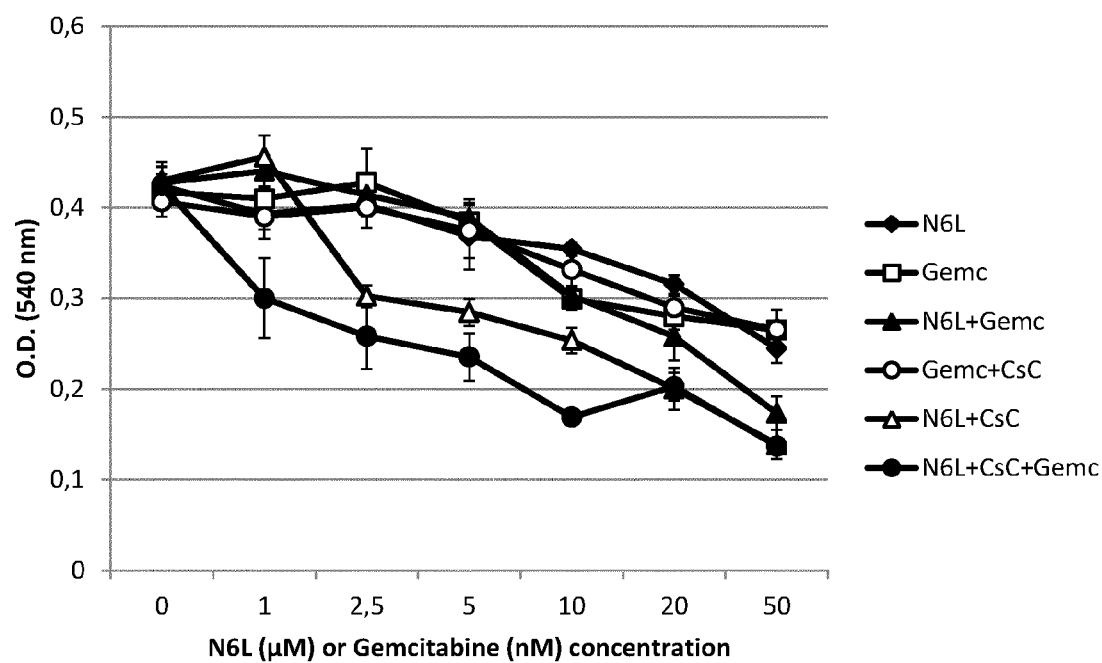
FIG. 22. Nanoparticles, but not N6L, induce the activity of gemcitabine. Similar number of PANC1 cells was treated with increasing concentrations of gemcitabine alone or in combination with N6L, Cs-C, or nanoparticles composed by Cs-C. Cells were treated every day for 4 days, in the presence of 5% FBS. At the end of the forth day, cell number was quantified using the MTT assay. Our results showed that gemcitabine slightly inhibited PANC1 proliferation. Furthermore, the mix of gemcitabine with N6L or Cs-C did not have any additive effect. However, an additive effect was observed in the case of mix of gemcitabine with nanoparticles.

In addition, Example 3 and FIGS. 20-21 shows that anti-angiogenic properties of Nucant compounds are also enhanced by incorporation of the Nucants into microspheres with GAGs. Compositions of the invention as described herein may thus also be for use in the treatment of disease involving deregulation of angiogenesis. The invention also relates to the use of a composition of the invention as described herein for the preparation of a for the treatment of disease involving deregulation of angiogenesis.

As disclosed in WO2007125210, Nucant compounds have been found to have anti-inflammatory activity; in particular, they inhibit the production of TNF-α, IL-6 and IL-8 as well as the expression of ICAM-1 by various cell types stimulated by LPS. These compounds are extremely interesting because, as mentioned earlier: no toxic effect of these compounds has been observed by the inventor, neither in vitro nor in vivo; these compounds are easy to synthesize, even on an industrial scale, under easily controlled conditions; these compounds have sufficient in vivo bioavailability of themselves not to need a particular pharmaceutical form to be developed.

In addition, the anti-inflammatory effect of Nucant compounds is at least partially linked to the fact that they exert anti-proliferative activity on inflammatory cells due to the surface nucleolin expression of proliferating inflammatory cells. The anti-inflammatory effect of Nucant compounds is thus also linked to their anti-proliferative activity on cells expressing surface nucleolin. This effect is potentialized by admixture with GAGs on cancer cells and should also be potentialized by admixture with GAGs for proliferating inflammatory cells.

The invention thus also relates to any composition of the invention as described herein, for use in the treatment of inflammatory diseases. The invention also relates to the use of any composition of the invention as described herein, for the preparation of a medicament for the treatment of inflammatory diseases.

The term "inflammatory disease" means any disease in which an inflammatory reaction has pathological consequences for the organism. In particular, inflammatory diseases in the context of the invention include autoimmune diseases (such as lupus or rheumatoid polyarthritis), septicaemia, septic shock, cardiac inflammatory diseases (carditis, and especially endocarditis, pericarditis, myocarditis, in particular those of an infectious origin such as those caused by *Staphylococcus aureus*), graft rejection, trauma, inflammatory diseases of the joints (notably, different forms of arthritis), inflammatory diseases of the gastrointestinal system (notably, colitis, enteritis, gastritis, gastroenteritis, and chronic inflammatory diseases of the intestine such as Crohn's disease and haemorrhagic rectocolitis (HRC)), inflammatory diseases of the skin (eczema, allergic contact dermatitis, psoriasis, dermatosis), inflammatory diseases of the respiratory system, especially chronic obstructive pulmonary disease (COPD), and allergies.

In an advantageous embodiment, the inflammatory disease is an autoimmune disease, in particular lupus or rheumatoid arthritis. In another advantageous embodiment, the inflammatory disease is septic shock. In yet another advantageous embodiment, the inflammatory disease is an endocarditis, particularly endocarditis of infectious origin, such as that caused by *Staphylococcus aureus*.

As disclosed in WO2009/141687, Nucant compounds have also been found to be useful for improving wound healing. The invention thus also relates to any composition of the invention as described herein, for use in improving wound healing. The invention also relates to the use of any composition of the invention as described herein, for the preparation of a medicament for improving wound healing.

In any aspect of the invention, the therapeutic composition of the invention can be in any pharmaceutically acceptable form and administered by any pharmaceutically acceptable route, for example, the therapeutic composition can be administered as an oral dosage, either single daily dose or unitary dosage form, for the treatment of a muscle disorder or conditions, e.g., diabetes. Such pharmaceutically acceptable carriers and excipients and methods of administration will be readily apparent to those of skill in the art, and include compositions and methods as described in the USP-NF 2008 (United States Pharmacopeia/National Formulary), which is incorporated herein by reference in its entirety. In certain aspects, the invention provides pharmaceutically acceptable formulations of the compounds described. These formulations include salts of the above compounds, e.g., acid addition salts, for example, salts of hydrochloric, hydrobromic, acetic acid, and benzene sulfonic acid.

The active compounds will generally be formulated for parenteral administration, e.g., formulated for injection via the intravenous, intraarthricular, intrathecal, intramuscular, sub-cutaneous, intra-lesional, or even intraperitoneal routes. The preparation of an aqueous composition that contains a cancer marker antibody, conjugate, inhibitor or other agent as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

A pharmacological composition or formulation refers to a composition or formulation in a form suitable for administration, e.g., systemic administration, into a cell or subject, preferably a human. By "systemic administration" is meant in vivo systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

Preparations for administration of the therapeutic of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's intravenous vehicles including fluid and nutrient replenishers, electrolyte replenishers, and the like. Preservatives and other additives may be added such as, for example, antimicrobial agents, anti-oxidants, chelating agents and inert gases and the like.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, intraperitoneal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful.

By pharmaceutically acceptable formulation is meant, a composition or formulation that allows for the effective distribution of the nucleic acid molecules of the instant invention in the physical location most suitable for their desired activity. Non-limiting examples of agents suitable for formulation with the nucleic acid molecules of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues, for example the CNS (Jolliet-Riant and Tillement, 1999, Fundam. Clin. Pharmacol., 13, 16-26); biodegradable polymers, such as poly(DL-lactide-coglycolide) microspheres for sustained release delivery after implantation (Emerich, D F et al, 1999, Cell Transplant, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999). Other non-limiting examples of delivery strategies, including CNS delivery of nucleic acid molecules include material described in Boado et al., 1998, J. Pharm. Sci., 87, 1308-1315; Tyler et al, 1999, FEBS Lett., 421, 280-284; Pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058. All these references are hereby incorporated herein by reference.

The invention also features the use of the composition comprising surface-modified liposomes containing poly (ethylene glycol) lipids (PEG-modified, or long-circulating liposomes or stealth liposomes). Nucleic acid molecules of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The compounds of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985) hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The formulations can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated to give controlled release of the active compound. For buccal administration the compositions may take the form of tablets or lozenges formulated in conventional manner.

Excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present. Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethan-e, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions suitable for injectable use include sterile aqueous solutions (where water soluble) or dispersions and sterile powders for the extemporaneous preparation of sterile injectable solutions or dispersion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g., sterile pyrogen-free water, before use. For intravenous administration, suitable carriers include physiological saline, bacteriostatic water, Cremophor™. (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

For administration to non-human animals, the therapeutic compositions of the invention can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water. The composition can also be administered to a subject in combination with other therapeutic compounds to increase the overall therapeutic effect. The use of multiple compounds to treat an indication can increase the beneficial effects while reducing the presence of side effects.

Some of the advantages of this invention are illustrated in the figures and examples given below, which are non-limiting on the scope of the invention. Additional, advantages and modifications will be apparent to those of skill in the art and include the application of routine techniques in the art and, as such, are expressly contemplated as being within the scope of the present invention.

EXAMPLES

It should be appreciated that the exemplary embodiments of the present invention should not be construed to be limited to the examples that are now described; rather, the exemplary embodiments of the present invention should be construed to include any and all applications provided herein and all variations within the skill of the ordinary artisan.

Example 1

Synergistic Effect of the Co-Administration of Different GAGs with Nucant 6L on Nucant 6L Anti Proliferative Properties Effect on the Growth of Human Pancreatic Cancer Cells (PANC-1, Human Pancreatic Carcinoma) Cells.

Figure 3:
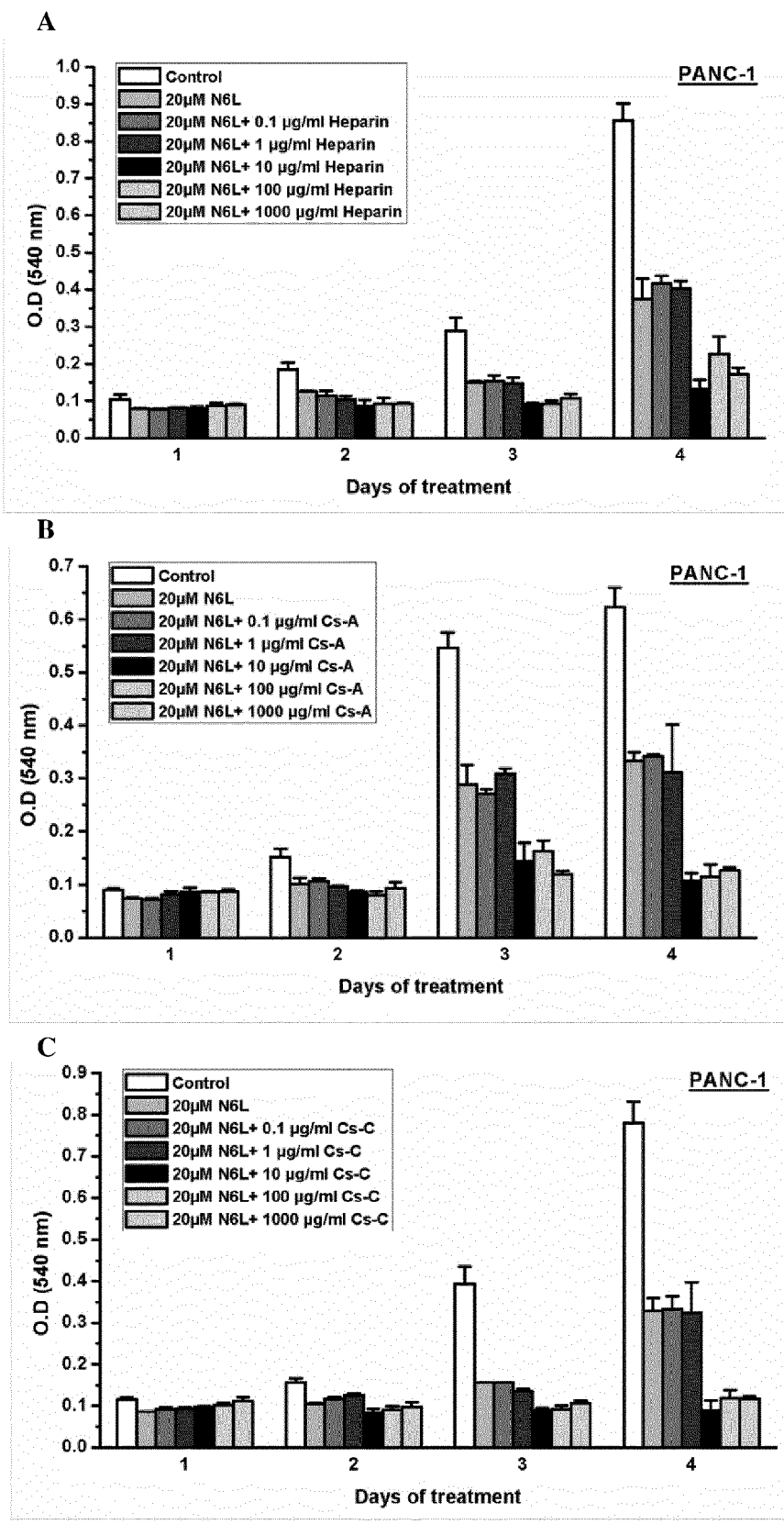
FIG. 3. Synergistic effect of the co-administration of compound Nucant 6L (N6L) and different GAGs. Effect of co-administration of N6L+different GAGs on the growth of PANC-1 (Human pancreatic carcinoma) cells: A. GAG=heparin; B. GAG=chondroitin sulfate A (Cs-A); and C. GAG=chondroitin sulfate C (Cs-C). Cells were treated every day with a mixture N6L/GAG (from about 20 μM N6L for 0 μg/ml to 1000 μg/ml GAG). The medium (DMEM 5% SVF) was changed every day. Proliferation was assessed by a MTT test. No effect on proliferation was observed with GAG alone.
Figure 5:
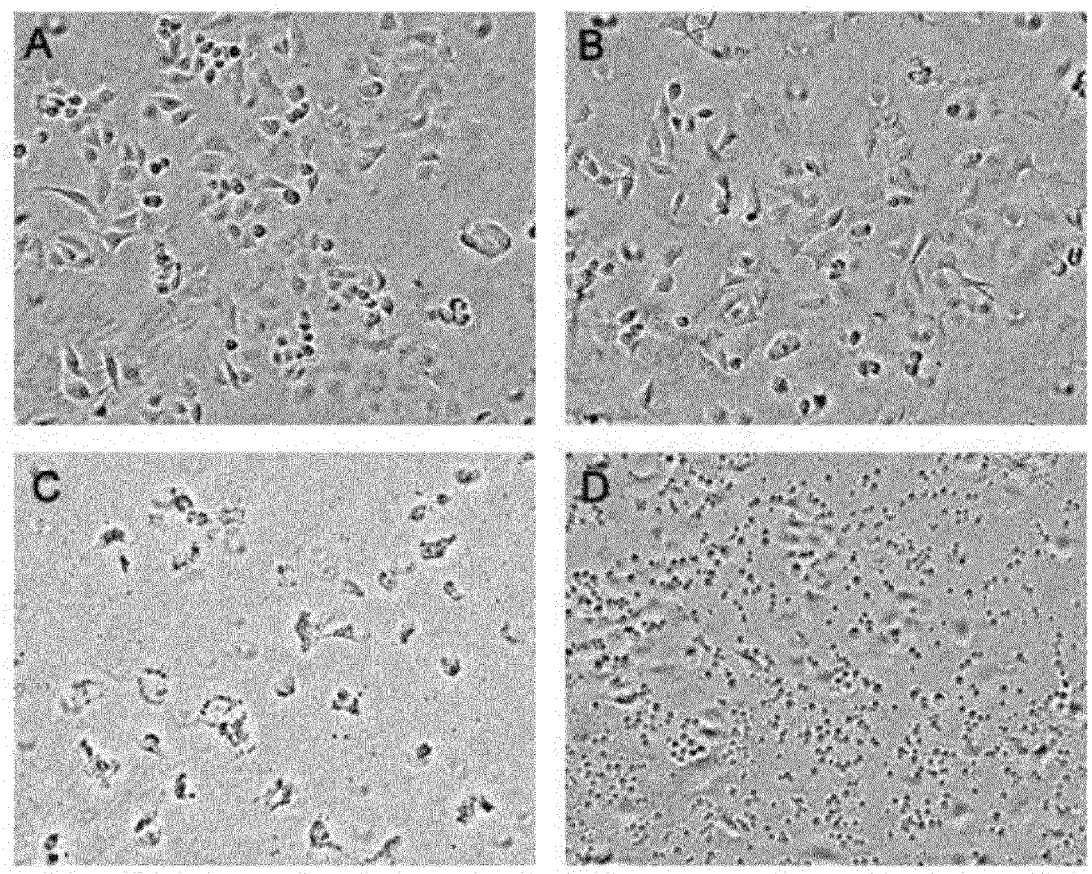
FIG. 5. Treatment of PANC-1 cells by N6L and heparin: A: PANC-1 cells control, B: PANC-1 cells treated with 20 μM of N6L, C: PANC-1 cells treated with a mixture of 20 μM of N6L and 10 μg/ml of heparin and D: PANC-1 cells treated with a mixture of 20 μM of N6L and 100 μg/ml of heparin.

Co-administration of N6L+different GAG on the growth of human pancreatic cancer cells (PANC-1, Human pancreatic carcinoma) cells (See FIG. 3). In FIG. 3A heparin is used as the exemplary GAG. In FIGS. 3B and C chondroitin sulfate A and chondroitin sulfate C are used in combination with N6L. Cells were treated every day with a mixture N6L/GAG (from about 20 μM/0 μg/ml to 1000 μg/ml GAG). The medium (DMEM 5% SVF) was changed every day. Proliferation was assessed by a MTT test. No effect on proliferation was observed with GAG alone. In FIG. 5 PANC-1 were either untreated (A) or treated with 20 μM of N6L (B), 20 μM of N6L and 10 μg/ml of heparin (C), or a mixture of 20 μM of N6L and 100 μg/ml of heparin (D).

Figure 9:
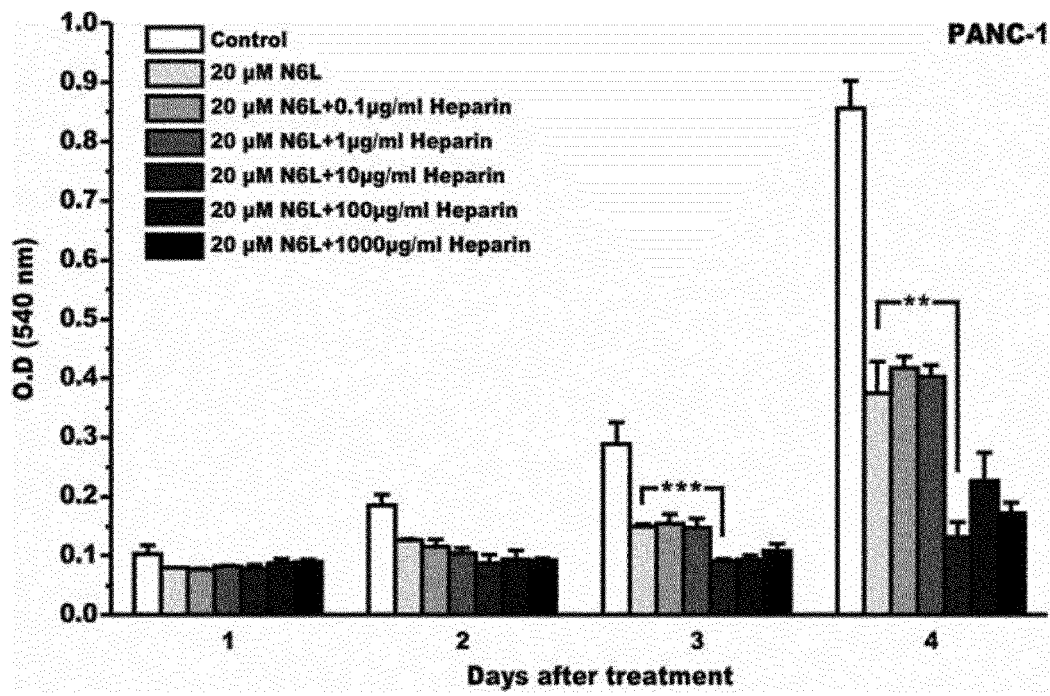
FIG. 9. Incubation of N6L with heparin results in the formation of nanoparticles that increase N6L inhibitory effect on anchorage-dependent proliferation of PANC1 cells. Similar number of PANC1 cells was treated with N6L or N6L that was pre-incubated with increasing concentrations of heparin, ranging from 0.1 to 1000 μg/ml. Cells were treated every day, for 4 days. At the end of the forth day, cell number was quantified using the MTT assay. We observed that after three days of treatment, N6L inhibited anchorage-dependent proliferation of PANC1 cells. However, our results showed that pre-incubation of N6L with 10, 100 or 1000 μg/ml heparin resulted in formation of nanoparticles that induced the inhibitory effect of the peptide. The maximal effect was observed at the concentration of 10 μg/ml of heparin and it is noteworthy that inhibition reached almost up to 90%. Results are mean values±SD of at least three independent experiments. $p<0.01$, *$p<0.001$.

In FIG. 9, PANC-1 cells were either untreated (Control) or treated with 20 μM of N6L alone or 20 μM of N6L admixed with 0.1 μg/ml, 1 μg/ml, 10 μg/ml, 100 μg/ml, or 1000 μg/ml heparin. As compared to the control group (not treated cells), N6L significantly inhibited anchorage-dependent proliferation of PANC1 cells after 3 and 4 days of treatment with inhibition ranging from 50% to 60%. Interestingly, pre-incubation of N6L with various concentration of heparin ranging from 10 μg/ml to 1000 μg/ml heparin resulted in potentiation of this inhibitory effect. The maximal effect was observed at the concentration of 10 μg/ml of heparin and it is noteworthy that inhibition reached to 86%, 4 days after treatment. Whatever the concentration of heparin used in this assay, no effect was observed when cells are incubated with heparin alone.

Figure 10:
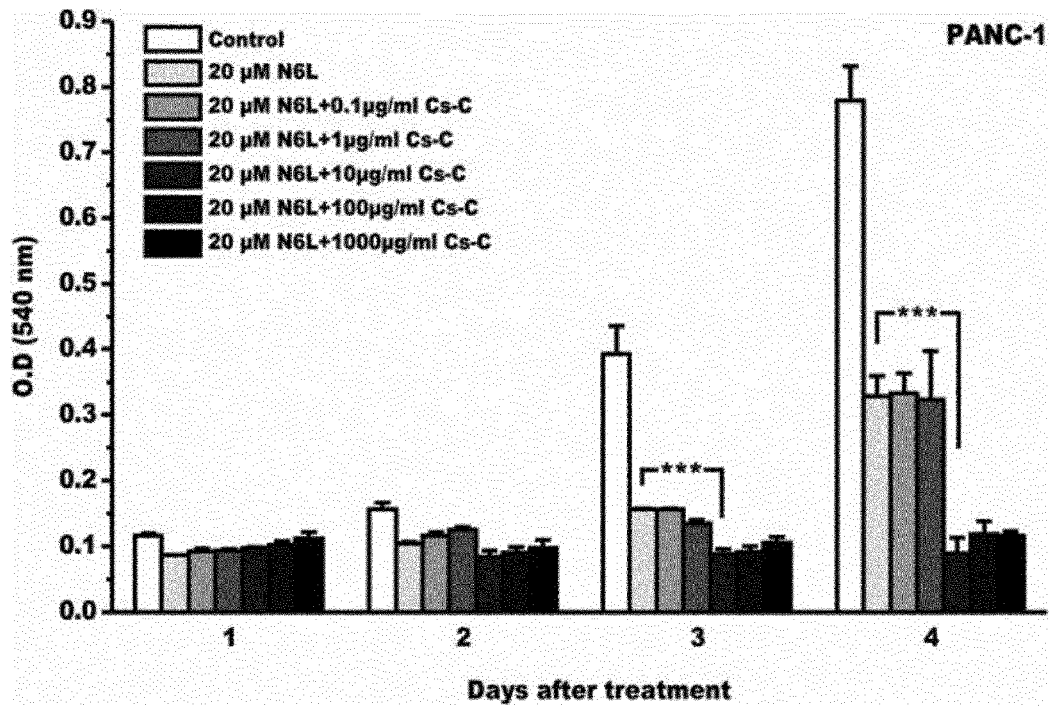
FIG. 10. Incubation of N6L with chondroitin sulfate-C (Cs-C) results in the formation of nanoparticles that increase N6L inhibitory effect on anchorage-dependent proliferation of PANC1 cells. Similar number of PANC1 cells was treated with N6L or N6L that was pre-incubated with increasing concentrations of Cs-C, ranging from 0.1 to 1000 µg/ml. Cells were treated every day, for 4 days. At the end of the forth day, cell number was quantified using the MTT assay. We observed that after three days of treatment, N6L inhibited anchorage-dependent proliferation of PANC1 cells. However, our results showed that pre-incubation of N6L with 10, 100 or 1000 µg/ml Cs-C resulted in formation of nanoparticles that induced the inhibitory effect of the peptide. The maximal effect was observed at the concentration of 10 µg/ml of Cs-C and it is noteworthy that inhibition reached almost up to 90%. Results are mean values±SD of at least three independent experiments. ***p<0.001.

In FIG. 10, PANC-1 cells were either untreated (Control) or treated with 20 μM of N6L alone or 20 μM of N6L admixed with 0.1 μg/ml, 1 μg/ml, 10 μg/ml, 100 μg/ml, or 1000 μg/ml chondroitin sulfate C (Cs-C). As compared to the control group (not treated cells), N6L significantly inhibited anchorage-dependent proliferation of PANC1 cells after 3 and 4 days of treatment with inhibition ranging from 50% to 60%. Interestingly, Pre-incubation of N6L with various concentration of heparin ranging from 10 μg/ml to 1000 μg/ml CS-C resulted in potentiation of this inhibitory effect. The maximal effect was observed at the concentration of 10 μg/ml of CS-C and it is noteworthy that inhibition reached almost up to 90%, 4 days after treatment. Whatever the concentration of CS-C used in this assay, no effect was observed when cells are incubated with CS-C alone.

Effect on Human Glioblastoma Cells (U87-MG, Human Glioblastoma-Astrocytoma)

Figure 4:
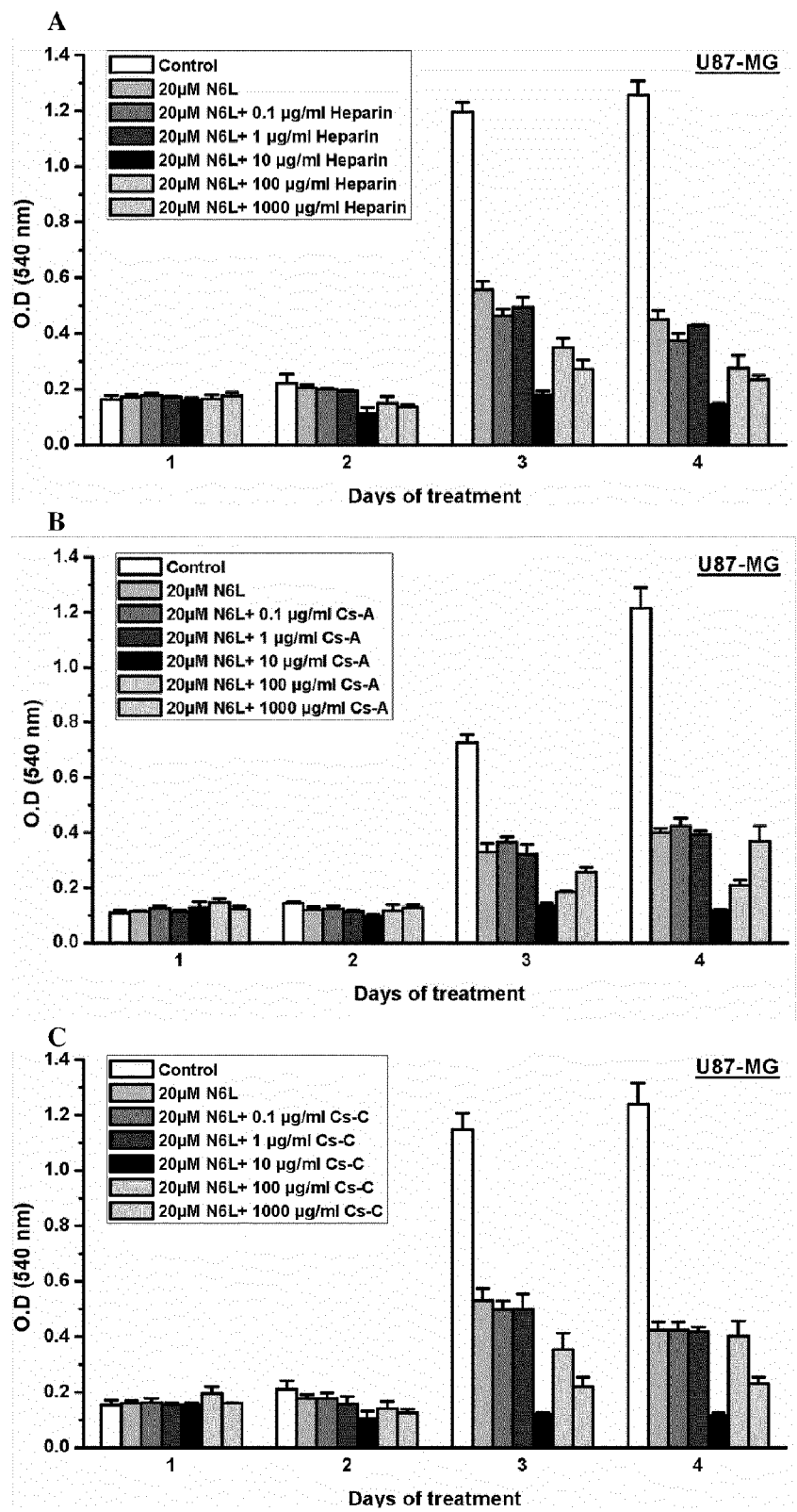
FIG. 4. Synergistic effect of the co-administration of compound Nucant 6L (N6L) and different GAGs. Effect of co-administration of N6L+different GAGs on the growth of U87-MG (Human glioblastoma-astrocytoma) cells: A. GAG=heparin; B. GAG=chondroitin sulfate A; and C. GAG=chondroitin sulfate C. Cells were treated every days with a mixture N6L/GAG (from about 20 μM N6L for 0 μg/ml to 1000 μg/ml GAG). The medium (DMEM 5% SVF) was changed every day. Proliferation was assessed by a MTT test. No effect on proliferation was observed with GAG.
Figure 6:
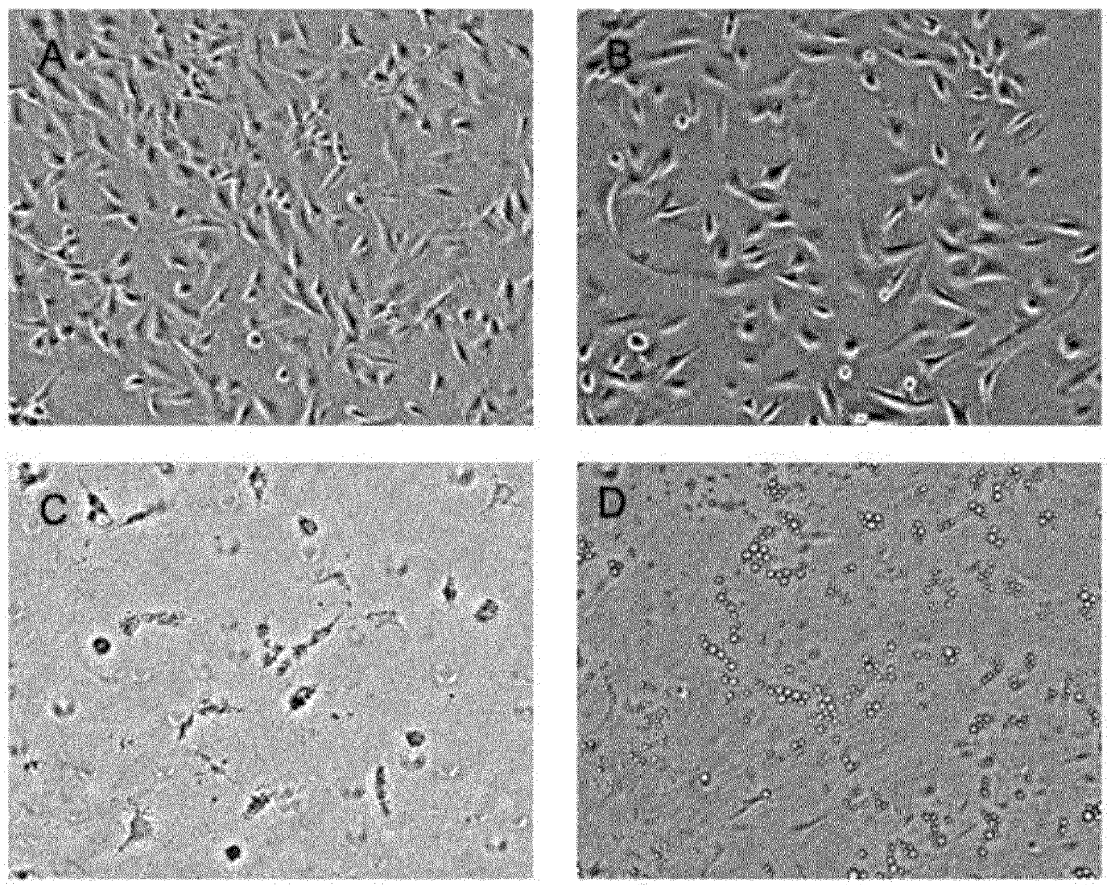
FIG. 6. Treatment of U87-MG cells by N6L and heparin: A: U87-MG cells control, B: U87-MG treated with 20 μM of N6L, C: U87-MG treated with a mixture of 20 μM of N6L and 10 μg/ml of heparin and D: U87-MG cells treated with a mixture of 20 μM of N6L and 100 μg/ml of heparin. Cells treated with the ratio N6L/GAG (20 μM/10 μg/ml) show "bubbles" which are much smaller than the one observed with other ratios which are localized on the cells.

Co-administration of N6L+different GAG on the growth of human glioblastoma cells (U87-MG, Human glioblastoma-astrocytoma) cells (See FIG. 4). In FIG. 4A heparin is used as the exemplary GAG. In FIGS. 4B and C chondroitin sulfate A and chondroitin sulfate C are used in combination with N6L. Cells were treated every days with a mixture N6L/GAG (from about 20 µM/0 µg/ml to 1000 µg/ml GAG). The medium (DMEM 5% SVF) was changed every day. Proliferation was assessed by a MTT test. No effect on proliferation was observed with GAG. In FIG. 6 U87-MG cells were either untreated (A) or treated with 20 µM of N6L (B), 20 µM of N6L and 10 µg/ml of heparin (C), or a mixture of 20 µM of N6L and 100 µg/ml of heparin (D).

Figure 11:
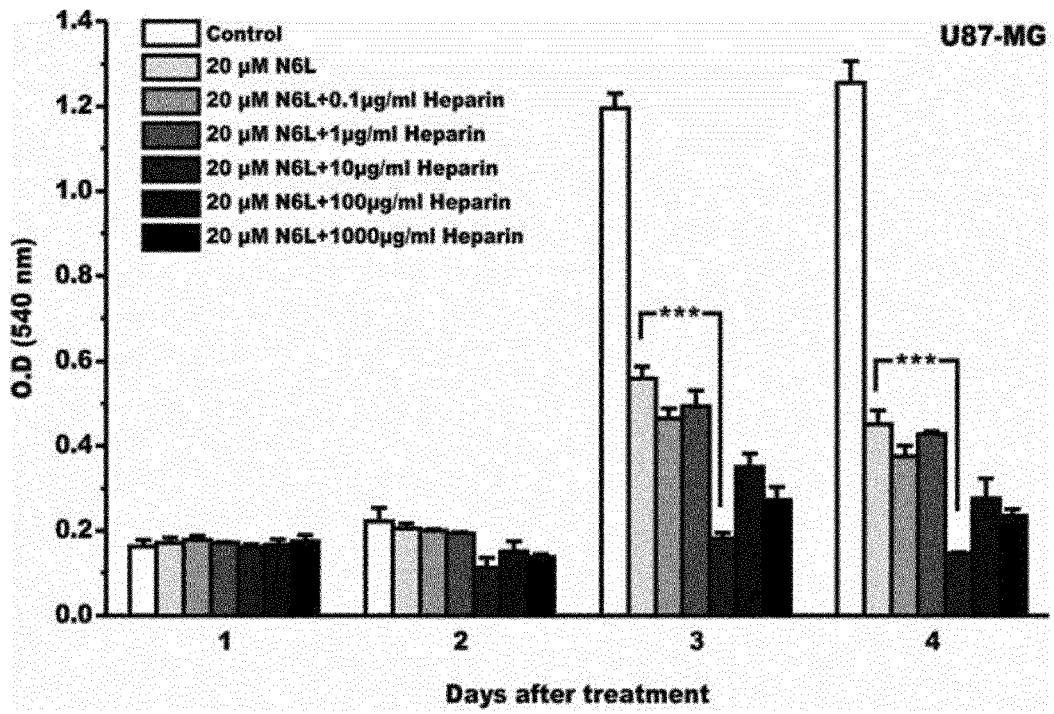
FIG. 11. Incubation of N6L with heparin results in the formation of nanoparticles that increase N6L inhibitory effect on anchorage-dependent proliferation of U87-MG cells. Similar number of U87-MG cells was treated with N6L or N6L that was pre-incubated with increasing concentrations of heparin, ranging from 0.1 to 1000 µg/ml. Cells were treated every day, for 4 days. At the end of the forth day, cell number was quantified using the MTT assay. We observed that after three days of treatment, N6L inhibited anchorage-dependent proliferation of U87-MG cells. However, our results showed that pre-incubation of N6L with 10, 100 or 1000 µg/ml heparin resulted in formation of nanoparticles that induced the inhibitory effect of the peptide. The maximal effect was observed at the concentration of 10 µg/ml of heparin and it is noteworthy that inhibition reached almost up to 90%. Results are mean values±SD of at least three independent experiments. ***p<0.001.

In FIG. 11, U87-MG cells were either untreated (Control) or treated with 20 µM of N6L alone or 20 µM of N6L admixed with 0.1 µg/ml, 1 µg/ml, 10 µg/ml, 100 µg/ml, or 1000 µg/ml heparin. As compared to the control group (not treated cells), N6L significantly inhibited anchorage-dependent proliferation of U87-MG cells after 3 and 4 days of treatment with inhibition ranging from 50% to 60%. Interestingly, Pre-incubation of N6L with various concentration of heparin ranging from 10 µg/ml to 1000 µg/ml heparin resulted in potentiation of this inhibitory effect. The maximal effect was observed at the concentration of 10 µg/ml of heparin and it is noteworthy that inhibition reached to 89%, 4 days after treatment. Whatever the concentration of heparin used in this assay, no effect was observed when cells are incubated with heparin alone.

Figure 12:
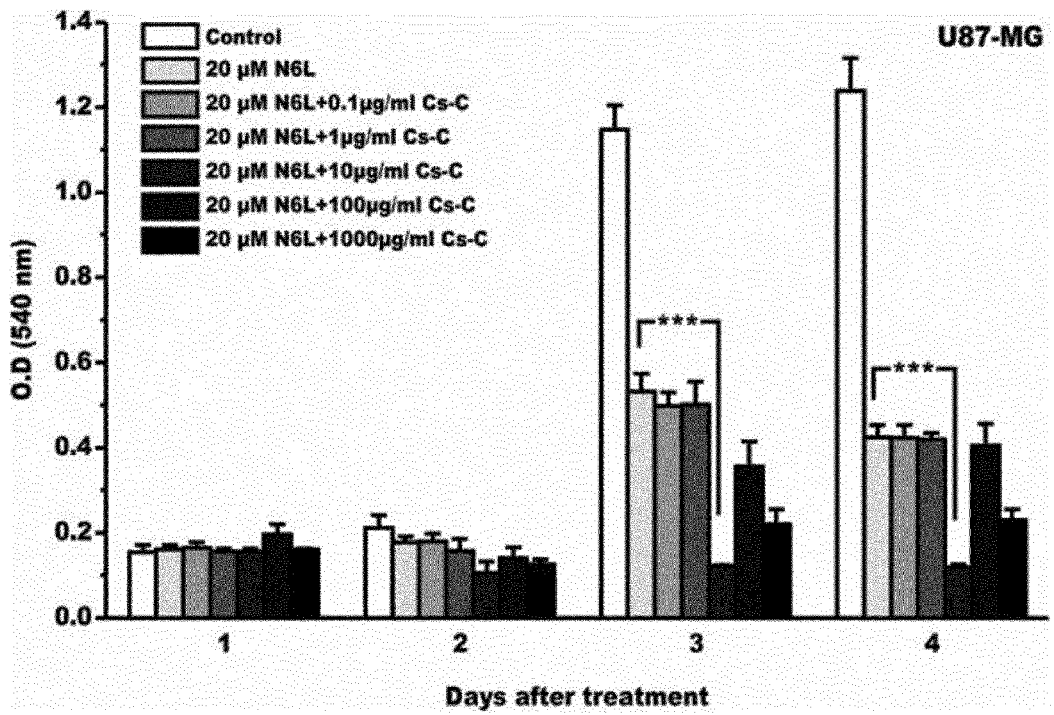
FIG. 12. Incubation of N6L with chondroitin sulfate-C (Cs-C) results in the formation of nanoparticles that increase N6L inhibitory effect on anchorage-dependent proliferation of U87-MG cells. Similar number of U87-MG cells was treated with N6L or N6L that was pre-incubated with increasing concentrations of Cs-C, ranging from 0.1 to 1000 µg/ml. Cells were treated every day, for 4 days. At the end of the forth day, cell number was quantified using the MTT assay. We observed that after three days of treatment, N6L inhibited anchorage-dependent proliferation of U87-MG cells. However, our results showed that pre-incubation of N6L with 10, 100 or 1000 µg/ml Cs-C resulted in formation of nanoparticles that induced the inhibitory effect of the peptide. The maximal effect was observed at the concentration of 10 µg/ml of Cs-C and it is noteworthy that inhibition reached almost up to 90%. Results are mean values±SD of at least three independent experiments. ***p<0.001.

In FIG. 12, U87-MG cells were either untreated (Control) or treated with 20 µM of N6L alone or 20 µM of N6L admixed with 0.1 µg/ml, 1 µg/ml, 10 µg/ml, 100 µg/ml, or 1000 µg/ml chondroitin sulfate C (Cs-C). As compared to the control group (not treated cells), N6L significantly inhibited anchorage-dependent proliferation of U87-MG cells after 3 and 4 days of treatment with inhibition ranging from 55% to 70%. Interestingly, Pre-incubation of N6L with various concentration of CS-C ranging from 10 µg/ml to 1000 µg/ml CS-C resulted in potentiation of this inhibitory effect. The maximal effect was observed at the concentration of 10 µg/ml of CS-C and it is noteworthy that inhibition reached to 90%, 4 days after treatment. Whatever the concentration of CS-C used in this assay, no effect was observed when cells are incubated with CS-C alone.

Figure 13:
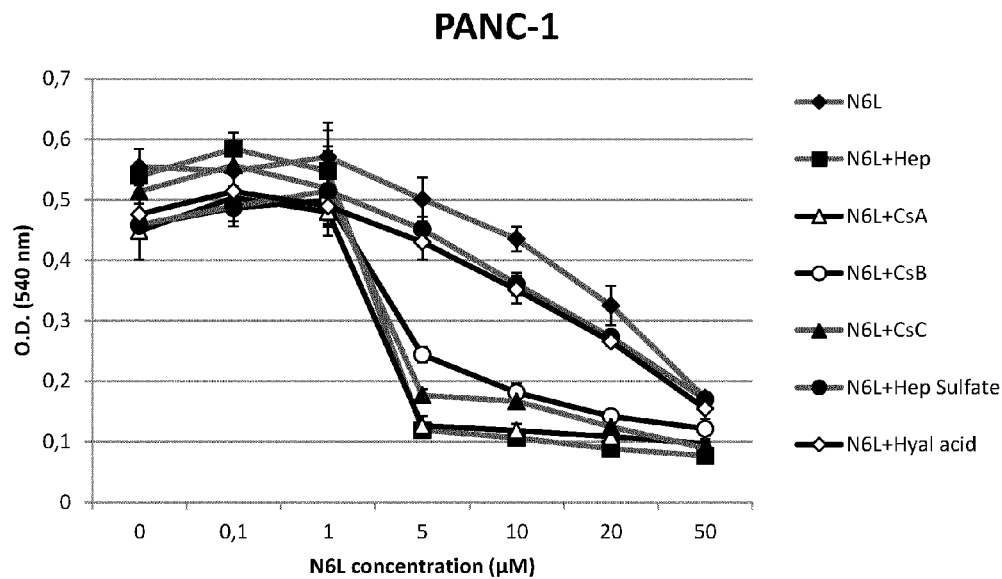
FIG. 13. Nanoparticles composed by the highly charged GAG molecules strongly inhibit anchorage-dependent proliferation of PANC1 cells, in contrast to N6L and nanoparticles composed by low charged GAG molecules that exert a slight inhibition. Similar number of PANC1 cells was treated with increasing concentrations of N6L or nanoparticles that were composed of increasing concentration of N6L and 10 µg/ml of different GAG molecules, in the presence of 5% FBS. Cells were treated every day, for 4 days. At the end of the forth day, cell number was quantified using the MTT assay. We observed that N6L inhibited the anchorage-dependent proliferation of PANC1 cells in a dose dependent manner having an IC50=15 µM. However, our results showed that pre-incubation of N6L with the highly charged GAG molecules, heparin, chondroitin sulfate-A (Cs-A), chondroitin sulfate-B (Cs-B), chondroitin sulfate-C (Cs-C) resulted in the formation of nanoparticles that strongly inhibited anchorage-dependent proliferation of PANC1 cells, having a maximal effect at a concentration of 5 µM (IC50=2.5 µM). Nanoparticles composed by higher concentrations of N6L exerted an effect similar to that of 5 µM. In contrast to the highly charged GAG molecules, N6L pre-incubation with the partially charged heparan sulfate or the uncharged hyaluronic acid did not form any nanoparticles and inhibited PANC1 proliferation in a similar manner to N6L.

Effect of N6L Pre-Incubated with Various Glycoaminoglycans on Anchorage-Dependent Proliferation of PANC1 Pancreatic Cancer Cell Line Treated all the Day To compare the efficacy of various glycoaminoglycans in the modulation of the effect of N6L on the anchorage-dependent proliferation of cancer cells, human pancreatic cancer cell line (PANC-1) were incubated with the mixture of N6L with these glycoaminoglycans (GAG) and cell proliferation was quantified via MMT assay (see FIG. 13).

Various concentration of N6L ranging from 0 to 50 µM were used, pre-incubated or not with 10 µg/ml of either heparin, CS-A, CS-B, CS-C heparan sulfate or hyaluronic acid. Cells were treated every day, for 4 days. At the end of the forth day, cell number was quantified using the MTT assay.

N6L used alone, inhibited the anchorage-dependent proliferation of PANC-1 cells in a dose dependent manner yielding an half maximum inhibitory concentration ($IC_{50}$) of 15 µM. As shown in FIG. 5, pre-incubation of N6L with the sulfated GAG molecules including either heparin, chondroitin sulfate-A (Cs-A), chondroitin sulfate-B (Cs-B), chondroitin sulfate-C (Cs-C) resulted in the potentiation of the effect of N6L used alone with a maximal effect at 5 µM and an $IC_{50}$ of 2.5 µM. In contrast, N6L pre-incubated with heparan sulfate or the hyaluronic acid inhibited the anchorage-dependent proliferation of PANC-1 cells in a similar manner to N6L.

Kinetics of the Inhibitory Effect of N6L Alone or N6L Pre-Incubated with Either Heparin or CS-C on PANC1 Pancreatic Cancer Cell Line PANC1 cells were treated with 20 µM N6L (control cell) or with N6L pre-incubated with either 10 µg/ml heparin or CS-C. Cells were treated either 1) at the first day and were allowed to proliferate for three more days or 2) the first and the second day and were allowed to proliferate for two more days or 3) the three first days and were allowed to proliferate for one more day and 4) for four days. At the end of the forth day, cell number was quantified using the MTT assay.

Figure 14:
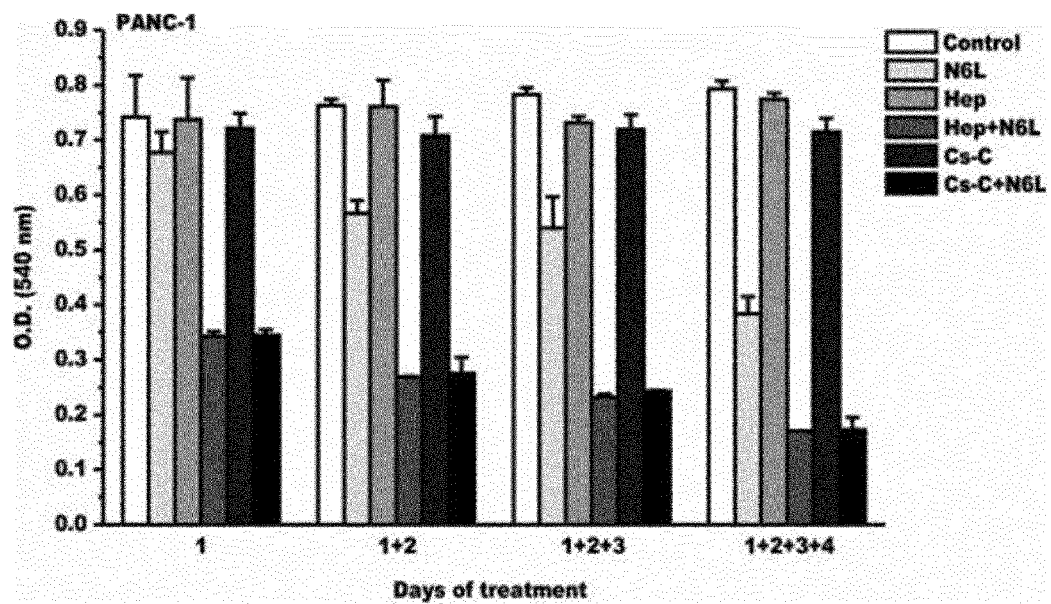
FIG. 14. Nanoparticles inhibitory effect on anchorage-dependent proliferation of PANC1 cells is observed after one day of treatment, while N6L exerts its effect after 4 treatments. Similar number of PANC1 cells was treated with 20 µM N6L or nanoparticles composed of 20 µM N6L and 10 µg/ml heparin or Cs-C, in the presence of 5% FBS. Cells were treated a. the first day and were allowed to proliferate for three more days, b. the first and the second day and were allowed to proliferate for two more days, c. the three first days and were allowed to proliferate for one more day and d. for four days. At the end of the forth day, cell number was quantified using the MTT assay. Our results showed that N6L did not exert any inhibitory effect after one day of treatment and its maximal effect (50% inhibition relative to control) was observed after four days. Interestingly, we observed that after one day of treatment, nanoparticles composed either by heparin or Cs-C inhibited PANC1 proliferation, in a manner similar to N6L activity after four days of treatment. Nanoparticles inhibitory effect was increased after every treatment and at the end of the four days treatment a small number of cells remained alive.

FIG. 14 shows that N6L did not exert any inhibitory effect after one day of treatment and its maximal effect corresponding to 50% inhibition relative to control, was observed after four days. Interestingly, a time dependent inhibition of cell proliferation in cells treated with N6L pre-incubated with GAG including heparin or CS-C was observed. In this case, inhibition of cell proliferation was observed after one day of treatment corresponding to 50% inhibition and more than 80% after 4 treatments.

Kinetics of the Inhibitory Effect of N6L Alone or N6L Pre-Incubated with Either Heparin or CS-C on U87-MG Glioblastoma Cancer Cell Line U87-MG cells were treated with 20 µM N6L (control cell) or with N6L pre-incubated with either 10 µg/ml heparin or CS-C. Cells were treated either 1) at the first day and were allowed to proliferate for three more days or 2) the first and the second day and were allowed to proliferate for two more days or 3) the three first days and were allowed to proliferate for one more day and 4) for four days. At the end of the forth day, cell number was quantified using the MTT assay.

Figure 15:
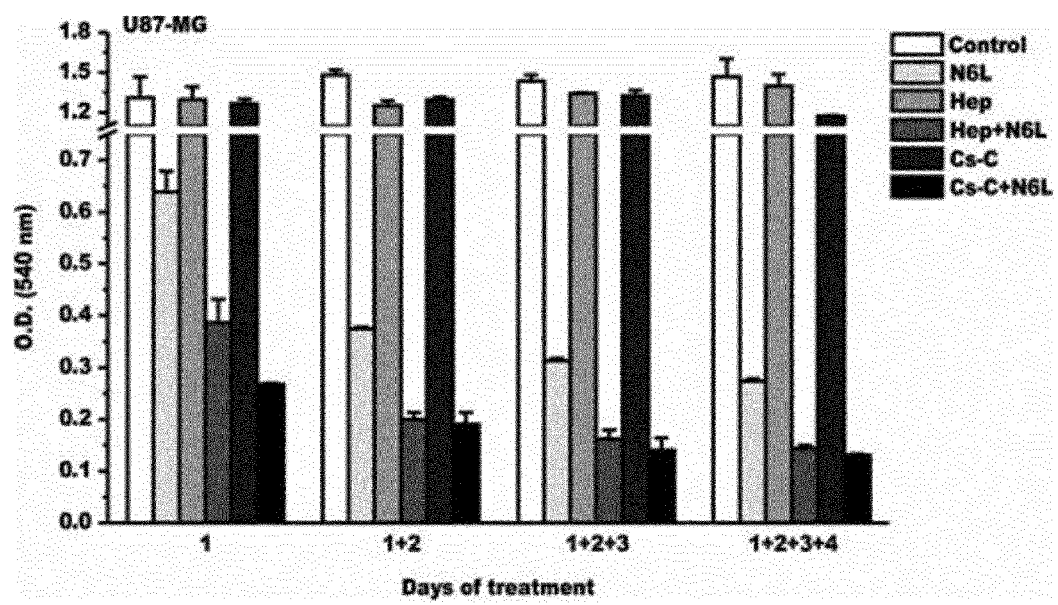
FIG. 15. One day of treatment of either N6L or nanoparticles inhibit anchorage-dependent proliferation of U87-MG cells, but nanoparticles effect is stronger than N6L. Similar number of U87-MG cells was treated with 20 µM N6L or nanoparticles composed of 20 µM N6L and 10 µg/ml heparin or CsC, in the presence of 5% FBS. Cells were treated a. the first day and were allowed to proliferate for three more days, b. the first and the second day and were allowed to proliferate for two more days, c. the three first days and were allowed to proliferate for one more day and d. for four days. At the end of the forth day, cell number was quantified using the MTT assay. We observed that after one day of treatment, both N6L and nanoparticles inhibited U87-MG proliferation, but the nanoparticles effect was stronger than N6L. Their inhibitory effect was increased after every treatment and at the end of the forth day some cells remained alive in the case of N6L, but the majority of the cells were dead in the case of nanoparticles.

FIG. 15 shows that N6L exert a slight inhibitory effect after one day of treatment and its maximal effect corresponding to 50% inhibition relative to control, was observed after four days. Interestingly, a time dependent inhibition of cell proliferation in cells treated with N6L pre-incubated with GAG including heparin or CS-C was observed. In this case, inhibition of cell proliferation was observed after one day of treatment corresponding to 80% inhibition and more than 90% after 4 treatments.

Admixture of N6L with GAGS Results in Formation of Microspheres

Figure 7:
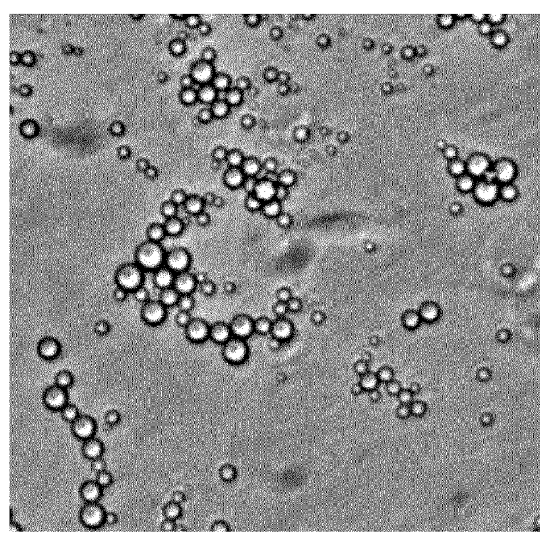
FIG. 7. Nucant-GAG microspheres. Microspheres observed with U87-MG cells using N6L 20 μM/heparin 100 μg/ml.
Figure 8:
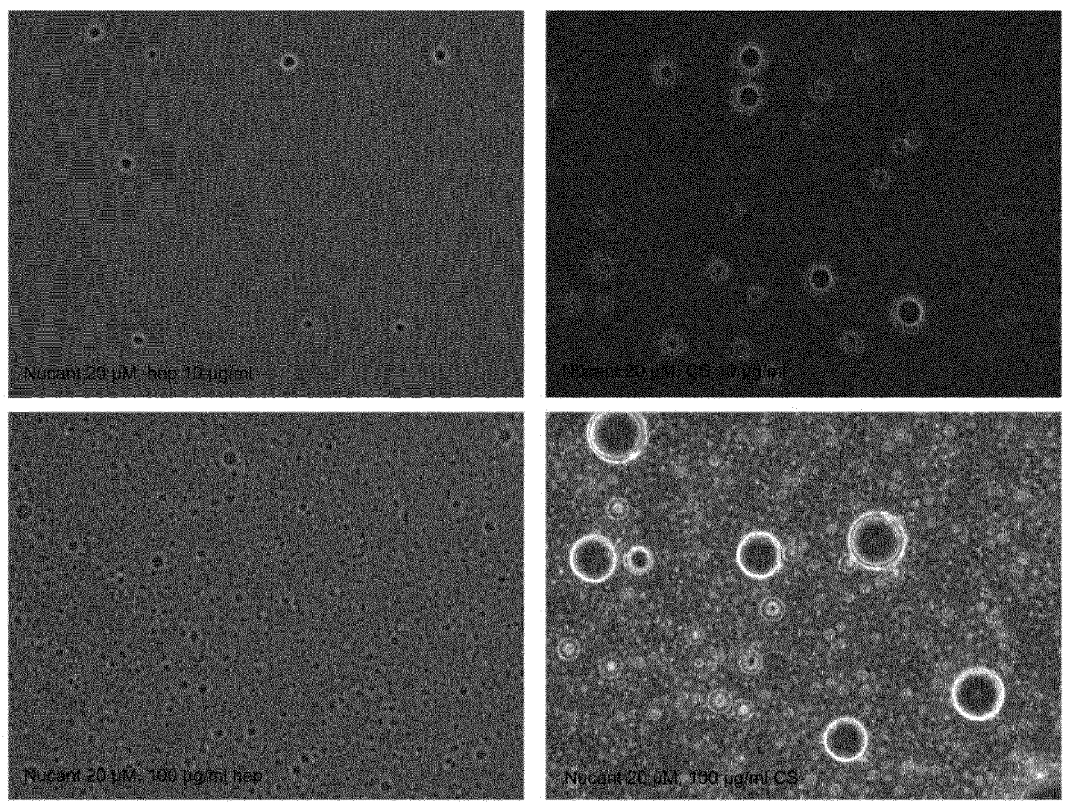
FIG. 8. The bubbles are microspheres constituted by N6L 20 μM and GAG. The largest ones observed with GAG 100 μg/ml have a size of approximately 500 nm. The size is positively correlated with the concentration of GAG in the medium.

Cells treated with the ratio N6L/GAG (20 µM/10 µg/ml and/or 100 µg/ml) show microspheres or "bubbles" which are much smaller than the one observed with other ratios which are localized on the cell (FIGS. 7 and 8). The bubbles are microspheres constituted by N6L and GAG. The largest ones observed with GAG 100 µg/ml have a size of approximately 500 nm. The size is positively correlated with the concentration of GAG in the medium. N6L together with GAG constitutes microspheres in which size is correlated to the concentration of GAG.

Conclusion

In summary, while no effect on proliferation was observed with GAG alone, heparin, chondroitin sulfate A, chondroitin sulfate B (now known as dermatan sulfate) and chondroitin sulfate C all enhance the anti-proliferative effect of N6L on PANC1 (human pancreatic cancer cells) and U87-MG (human glioblastoma cells) cancer cells (see FIGS. 3-6 and 9-12). No such enhancement of N6L anti-proliferative properties has been observed when using hyaluronan or heparin sulfate (data not shown and FIG. 13).

In addition, while repeated treatment (each day) significantly improves the anti-proliferative effect of N6L alone, it only slightly improves the anti-proliferative effect of N6L previously admixed with heparin or chondroitin sulfate (see FIGS. 14-15). Indeed, even a single treatment with N6L previously admixed with heparin or chondroitin sulfate C (Cs-C) resulted in a time-dependent inhibition of PANC1 and U87-MG cancer cells.

Admixture of N6L with GAGs resulted in interaction of both compounds and formation of microspheres (see FIGS. 7-8)

Example 2

Influence of Weight Ratio of Nucant6L to GAG on Potentialization of Nucant6L Antiproliferative Properties Approximately $5 \times 10^3$ of PANC1 (obtained from ATCC, American type culture collection cells resuspended in DMEM containing 10% of fetal bovine serum (FBS) were seeded into a 48-well culture plates and incubated at 37° C. during 24 hours. The culture medium then was changed to DMEM containing 0.5 FBS. Cells were then treated by N6L concentration ranging from 2.5 µM to 40 µM pre-incubated or not with Cs-C in a ponderal ratio between N6L and CS-C of 8 and 16 for 2 hours and then treated all the day during 7 days. At the end of the seventh day, cell number was quantified using the MTT assay.

Results are presented in FIGS. 16 to 19, and indicate that 2 hours of daily treatment with N6L pre-incubated with CS-C is sufficient to inhibit anchorage-dependent proliferation of cells. In addition, comparison of the growth curves indicates that a N6L/Cs-C weight ratio of 8 is more efficient than a N6L/Cs-C weight ratio of 16.

The time-dependent inhibition is observed at concentrations of N6L of 2.5 (FIG. 19) or greater (FIGS. 16-18) pre-incubated with CS-C.

Figure 16:
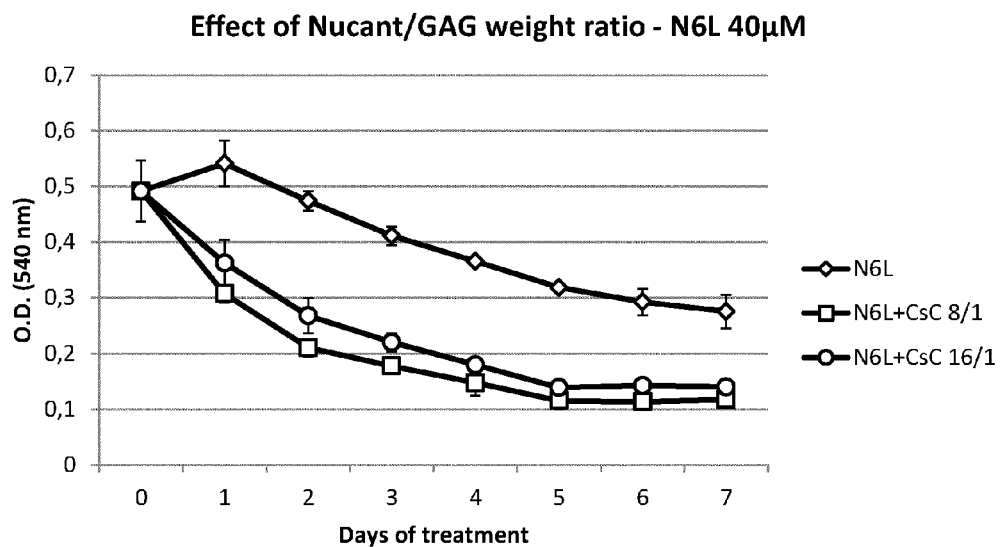
FIGS. 16, 17, 18, and 19. Study of the factors (treatment period and N6L concentration) that regulate nanoparticles activity. Similar number of PANC1 cells was treated every day for 2 h, with increasing concentrations of N6L or nanoparticles that were formed after mix of N6L with Cs-C in a final ratio 8:1 and 16:1. At the end of the seventh day, cell number was quantified using the MTT assay. Our results showed that N6L and nanoparticles activity was retained after seven days of 2 h daily treatment, proving that cells did not become resistant to the treatment, and indicating that 2 h of daily treatment is the minimal required time for N6L and nanoparticles to exert their biological activity. Furthermore, we observed that the nanoparticles composed by N6L and Cs-C at the ratio 8:1 inhibited stronger the anchorage-dependent proliferation of PANC1 cells than the ratio 16:1 or the N6L alone. Finally, we assume that the ratio between the N6L and the Cs-C is not the critical factor for the nanoparticles activity, since the effect was not the same for the nanoparticles that had the same ratio but were fainted by different concentrations of N6L and Cs-C.
Figure 17:
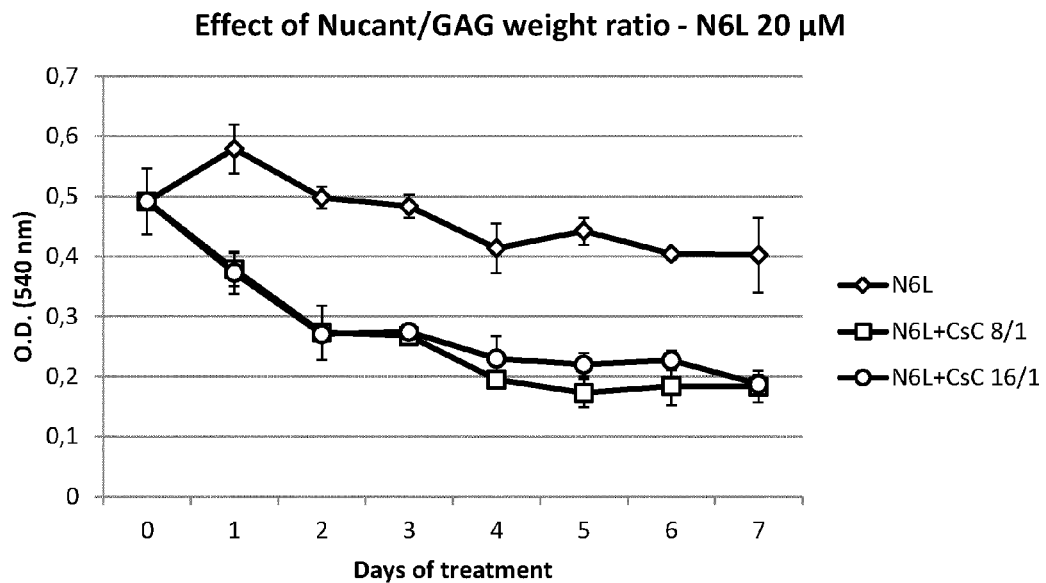
Figure 18:
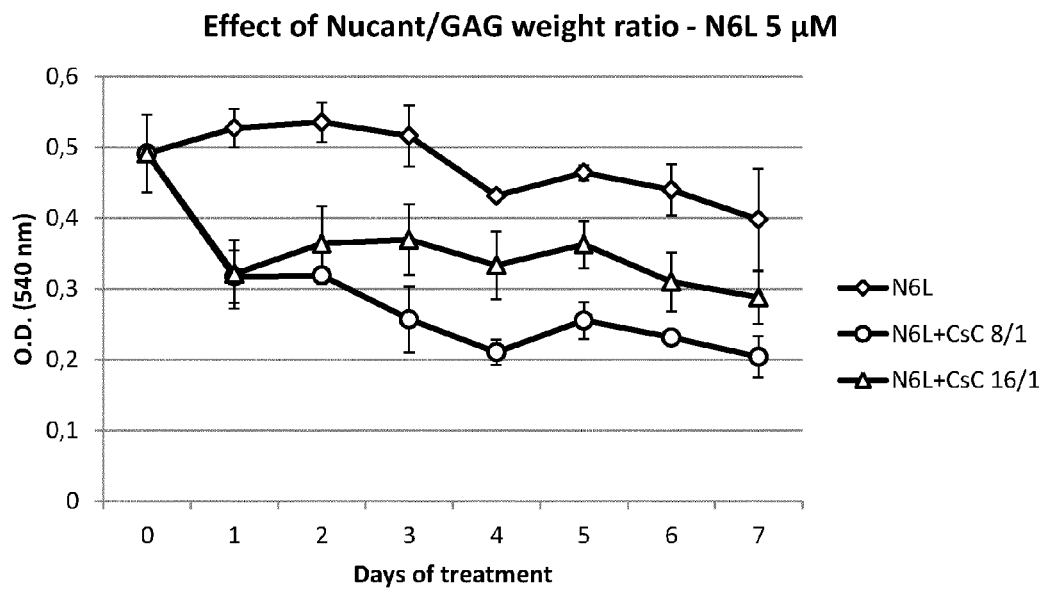
Figure 19:
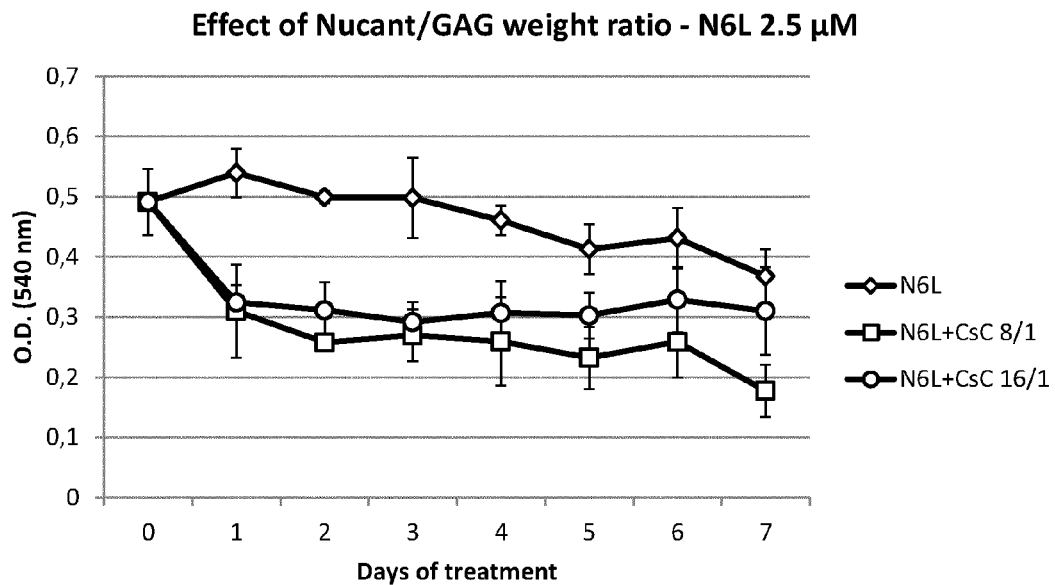

In addition, it has to be noted that while selection of an optimal N6L/Cs-C weight ratio of 8 is particularly important at low N6L concentrations (2.5 or 5 µM, see FIGS. 18-19), it is not as important at higher N6L concentrations (20 or 40 µM, see FIGS. 16-17).

Example 3

Synergistic Effect of the Co-Administration of Different GAGs with Nucant 6L on Nucant 6L Anti-Angiogenic Properties Study of the Effect of N6L Pre-Incubated with Various Glycoaminoglycans on Anchorage-Dependent Proliferation of Human Endothelial Cells (See FIG. 20)
Overview:
To compare the efficacy of various GAG in the modulation of the effect of N6L on the anchorage-dependent proliferation of human endothelial cells, HUVEC cells were challenged with the mixture of N6L and these GAG. Four days later, cell proliferation was quantified via MMT assay.
Methodology:
Similar number ($5 \times 10^3$) of HUVEC cells was treated with increasing concentrations of N6L ranging from 0.1 to 50 µM or pre-incubated or not with 10 µg/ml of either CS-A, CS-B, CS-C, heparin, heparan sulfate or hyaluronic acid. Cells were treated every day for 4 days. At the end of the forth day, cell number was quantified using the MTT assay.

Results:
N6L used alone, inhibited the anchorage-dependent proliferation of HUVEC cells in a dose dependent manner yielding a maximal effect at 50 µM. Interestingly, pre-incubation of N6L with sulfated GAG molecules including either heparin, chondroitin sulfate-A (Cs-A), chondroitin sulfate-B (Cs-B), chondroitin sulfate-C (Cs-C) resulted in the potentiation of the effect of N6L used alone with a maximal effect observed at 5 µM and an $IC_{50}$ of 2.5 µM. In contrast, N6L pre-incubated with heparan sulfate or the hyaluronic acid inhibited the anchorage-dependent proliferation of PANC-1 cells in a similar manner than N6L (FIG. 20).

Study of the Effect of N6L Pre-Incubated with Sulfated Glycoaminoglycans on In Vivo Angiogenesis (See FIG. 21)
Overview:
To analyse the effects of N6L pre-incubated with sulfated glycoaminoglycans on in vivo angiogenesis using chicken embryo chorioallantoic membrane assay.
Methodology:
Leghorn fertilized eggs were incubated for 4 days at 37° C. A window was then opened on the eggshell, exposing the CAM. The window was covered with sterile tape, and the eggs were returned to the incubator. On day 9 of embryo development, 20 ml of distilled water as a control or containing either 20 µM N6L, 10 ml heparin or 10 µg/ml CS-C alone or 20 µM N6L pre-incubated with either 10 µg/ml heparin or 10 µg/ml CS-C inside a silicone ring to restricted the area which is 1 cm². After 48 hours of incubation at 37° C., CAMs were fixed in situ with saline-buffered formalin, excised from the eggs, placed on slides, and left to dry in air. Photographs were taken and the total length of the vessels was quantified using PC image-analysis software (Scion Corporation, USA). Results are mean values±SD from at least 3 independent experiments.
Results:
As compared to the control performed with water, N6L used at the concentration of 20 µM, had no significant effect on the in vivo angiogenesis. In contrast, when 20 µM N6L was pre-incubated with either heparin or CS-C and applied to the chicken embryo chorioallantoic membrane a significant inhibition of the development of new blood vessel has been observed (50% and 70%, respectively, see FIG. 21). As control, no effect was observed when heparin or CS-C was applied alone on the chicken embryo chorioallantoic membrane. Results are mean values±SD from at least 3 independent experiments.
Conclusion
The above results show that admixture of Nucant compounds with GAGs n of only potentialize their anti-proliferative activity but also potentialize their anti-angiogenic activity.

Example 4

Synergistic Effect of N6L Pre-Incubated with CS-C and Gemcitanine

Overview:
The purpose of this study was to determine if N6L pre-incubated or not with CS-C and gemcitabine have a synergistic effect.
Methodology:
Approximately $5 \times 10^3$ of PANC1 (obtained from ATCC, American type culture collection cells resuspended in DMEM containing 10% of fetal bovine serum (FBS) were seeded into a 48-well culture plates and incubated at 37° C. during 24 hours. The culture medium then was changed to DMEM containing 5 FBS. Cells were then treated by N6L concentration ranging from 1 µM to 50 µM pre-incubated or not with Cs-C in the presence or absence of various concentration of gemcitabine ranging from 1 nM to 50 nM all the day during 4 days. At the end of the fourth day, cell number was quantified using the MTT assay.

Results:

In this experimental conditions, a slight inhibition of cell proliferation by gemcitabine has been observed and no potentiation effect is found when gemcitabine is pre-incubated with CS-C. As expected, pre-incubation of N6L with Cs-C gave rise to a potentiation effect compared to N6L alone. Interestingly, addition of gemcitabine to the mixture of N6L+CS-C resulted in a further synergistic effect.

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following

REFERENCES

The following references are incorporated herein by reference in their entirely for all purposes.

Aldrian-Herrada et al., 1998, Nucleic Acids Res., 26, 4910-4916;
Alete et al., FEBS J., 2006; 273:4668-81
Atherton, E.; Sheppard, R. C. (1989). Solid Phase peptide synthesis: a practical approach. Oxford, England: IRL Press;
Bast, R. C. et al, New England J. Med., 309:883-887 (1983)
Bellet, D. H. et al, Proc. Natl. Acad. Sci., USA, 81:3869-3873 (1984)
Boado, 1995, Adv. Drug Delivery Rev., 15, 73-107;
Boado et al., 1998, J. Pharm. Sci., 87, 1308-1315;
Callebaut, C., Jacotot, E., Krust, B., Guichar, G., Blanco, J., Svab, J., Muller, S., Briand, J. P., and Hovanessian, A. G. (1997) J. Biol. Chem. 272, 7159-7166
Callebaut, C., Blanco, J., Benkirane, N., Krust, B., Jacotot, E., Guichard, G., Seddiki, N., Svab, J., Dam, E., Muller, S., Briand, J. P., and Hovanessian, A. G. (1998) J. Biol. Chem. 273, 21988-2199
Carpino L. A. (1993). J. Am. Chem. Soc. 115 (10): 4397-4398
Christian, S., Pilch, J., Akerman, M. E., Porkka, K., Laakkonen, P., and Ruoslahti, E. (2003) J. Cell Biol. 163, 871-878
Emerich, D F et al, 1999, Cell Transplant, 8, 47-58
Engleton et al., Peptides 9:1431-1439 (1997)
Gregoriadis, Liposome Technology, Vols. I to III, 2nd ed. (CRC Press, Boca Raton Fla. (1993)
Hayes, D. F. et al, J. Clin. Invest., 75:1671 (1985),
Hedin, A. et al, Proc. Natl. Acad. Sci., USA. 80:3470 (1983),
Herlyn, M. et al, J. Clin. Immunol., 2:135 (1982),
Ishiwata et al., Chem. Pharm. Bull. 1995, 43, 1005-1011
Jolliet-Riant and Tillement, 1999, Fundam. Clin. Pharmacol., 13, 16-26
Killian, C. S. et al, J. Natl. Cancer Inst., 76:179 (1986),
Killian, C. S. et al, Cancer Res., 45:886 (1985),
Klug, T. L. et al, Cancer Res., 44:1048 (1984),
Kreuter et al., Brain Res. 674:171-174 (1995)
Krust et al., PNAS, 2001 Nov. 20; 98(24):14090-095;
Lasic et al. Chem. Rev. 1995, 95, 2601-2627;
Merrifield R. B. (1963). J. Am. Chem. Soc. 85 (14): 2149-2154;
Metzgar, R. S. et al, Proc. Natl. Acad. Sci., USA. 81:5242 (1984),
Nisole et al., AIDS Res. Hum. Retroviruses, 2000 Feb. 10; 16(3):237-49;
Nisole et al., J. Biol. Chem., 2002 Jun. 7; 277(23)20877-86;
Nisole et al., J. Biol. Chem., 1999 Sep. 24; 274(39):27875-84;
Papsidero, L. D. et al, Cancer Res., 44:4653 (1984),
Pardridge et al., 1995, PNAS USA., 92, 5592-5596;
Pekary, A. E. et al, Clin. Chem., 30:1213-1215 (1984),
Prog Neuropsychopharmacol Biol Psychiatry, 23, 941-949, 1999
Semenkovich, C. F., Ostlund, R. E. J., Olson, M. O., and Yang, J. W. (1990) Biochemistry 29, 9708-9713
Stewart, J. M.; Young, J. D. (1984). Solid phase peptide synthesis, 2nd edition, Rockford: Pierce Chemical Company, 91;
Tyler et al, 1999, FEBS Lett., 421, 280-284;
Tyler et al., 1999, PNAS USA., 96, 7053-7058 U.S. Pat. No. 4,522,811
U.S. Pat. No. 3,773,919
WO2007/125210
WO2009/141687

The invention claimed is:

1. A composition comprising:
   a) a polyvalent synthetic compound comprising a linear peptide support on which at least 3 pseudopeptide units are grafted, said pseudopeptide units being of formula:

$Y_1\text{-}\psi\text{-}Z\text{-}Y_2$, wherein:
   $Y_1$ and $Y_2$ are selected independently from amino acids having a basic side chain;
   Z is selected from: proline or derivatives thereof; and
   ψ represents a reduced bond (—$CH_2NH$—), a retro-inverso bond (—NHCO—), a methyleneoxy bond (—$CH_2O$—), a thiomethylene bond (—$CH_2$—S—), a carba bond (—$CH_2CH_2$—), a ketomethylene bond (—CO—$CH_2$—), a hydroxyethylene bond (—CHOH—$CH_2$—), a (—N—N) bond, an E-alkene bond or a (—CH═CH—) bond; and
   b) a glycosaminoglycan (GAG).

2. The composition of claim 1, wherein said support comprises:
   a) a cyclic hexapeptide consisting of alternating alkaline (A) residues of configuration D and Lysine (K) residues of configuration L; or
   b) 5 lysine residues linked by amide bonds at the ε amino group of each Lysine residue or
   c) a linear peptide of sequence SEQ ID NO: 1, SEQ ID NO: 2, SEQ ID NO: 3, SEQ ID NO: 4, SEQ ID NO: 8, SEQ ID NO: 9, SEQ ID NO: 13, SEQ ID NO: 14, SEQ ID NO: 15, SEQ ID NO: 18, SEQ ID NO: 19, SEQ ID NO: 22 and SEQ ID NO: 24.

3. The composition of claim 1, wherein said pseudopeptide units are grafted directly on said support.

4. The composition of claim 1, wherein the compound comprises between 3 and 15 pseudopeptide units.

5. The composition of claim 1, wherein Z is proline (P).

6. The composition of claim 1, wherein $Y_1$ and $Y_2$ are independently selected from arginine (R) and lysine (K).

7. The composition of claim 1, wherein the compound is selected from compounds of formula:

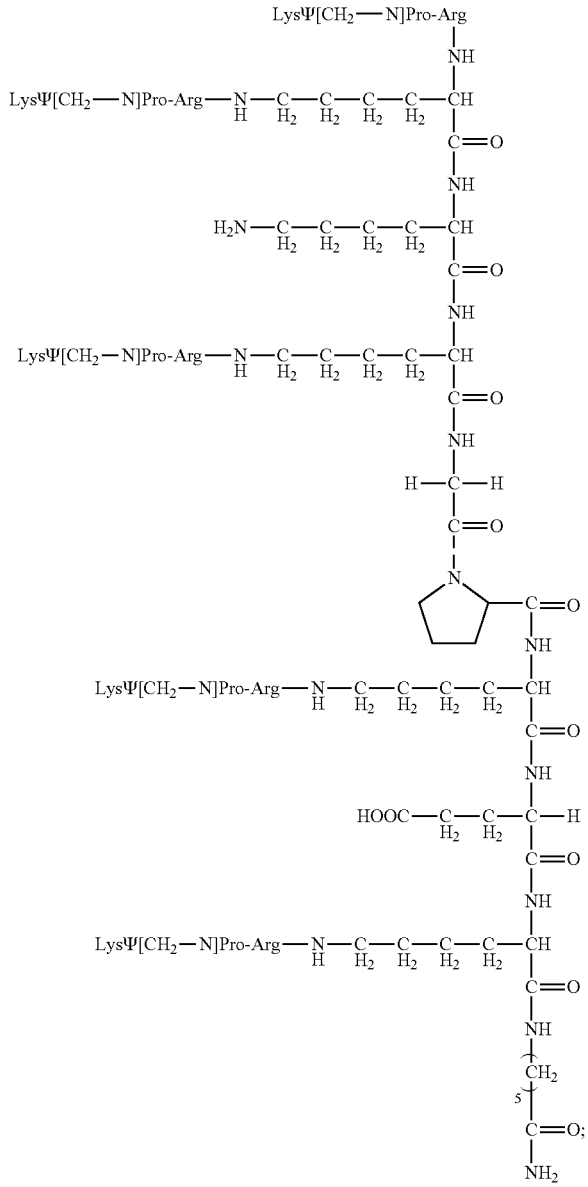

-continued
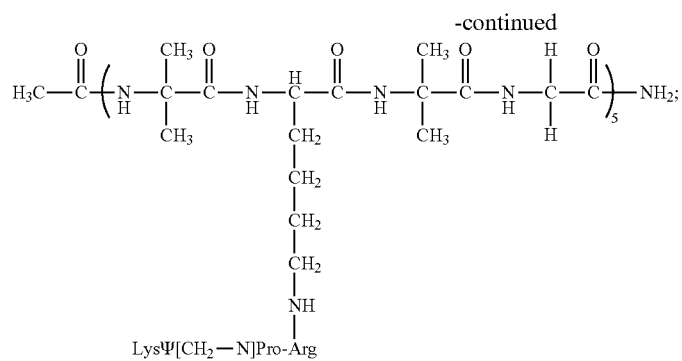
Nucant 2
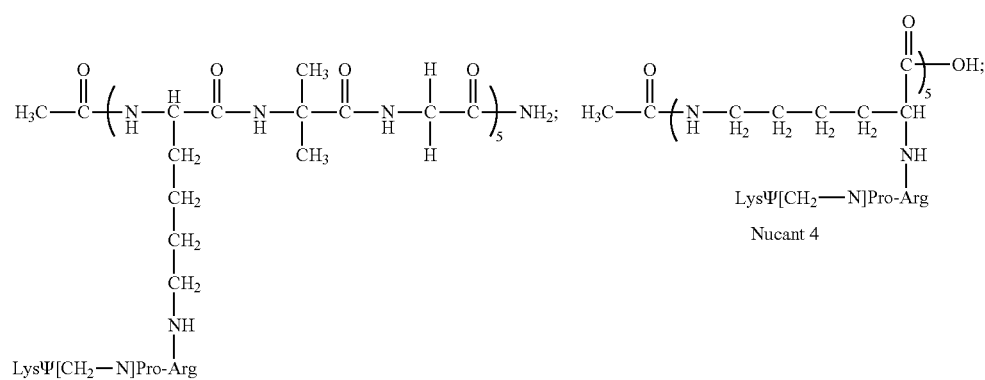
Nucant 3    Nucant 4
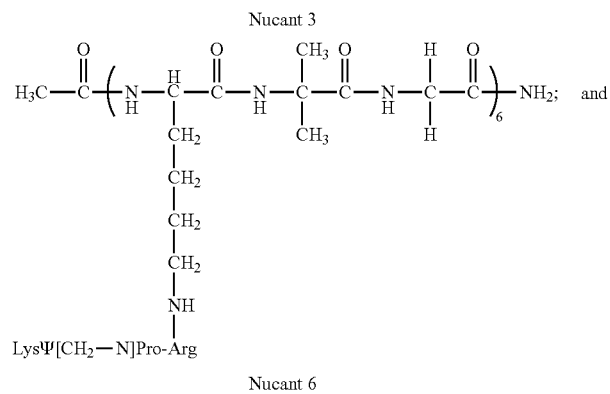
Nucant 6
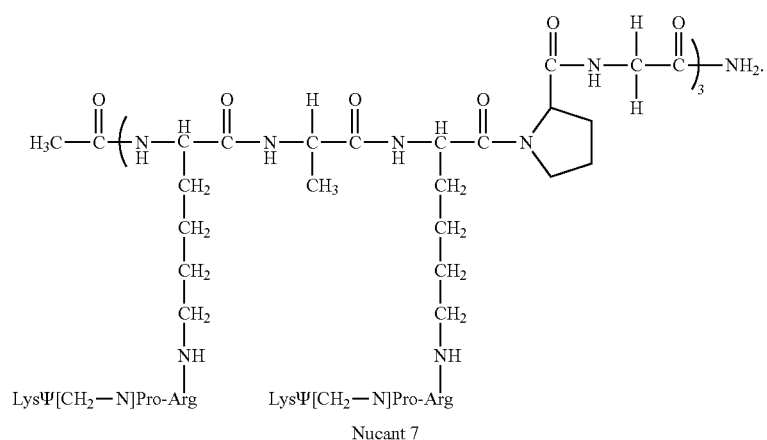
Nucant 7

8. The composition of claim 1, wherein the lysine residues in the pseudopeptide units are all in D configuration or all in L configuration.

9. The composition of claim 1 or 7, wherein the GAG is selected from heparin, chondroitin sulfate A, chondroitin sulfate B, chondroitin sulfate C, and combinations thereof.

10. The composition of claim 1, wherein the composition comprises at least 1 μM of the polyvalent synthetic compound.

11. The composition of claim 1, wherein the weight ratio of the polyvalent synthetic compound to the GAG is comprised between 0.01 and 24.

12. The composition of claim 1, wherein the polyvalent synthetic compound is admixed with the GAG.

13. The composition of claim 12, wherein another active compound such as but not limited to a cytotoxic agent is admix to it.

14. A method of treating a disease involving deregulation of cell proliferation and/or angiogenesis, comprising administering the composition of claim 1 to a patient in need thereof.

15. A method of treating an inflammatory disease, comprising administering the composition of claim 1 to a patient in need thereof.

16. A method of improving wound healing, comprising administering the composition of claim 1 to a patient in need thereof.

17. A method of inhibiting proliferation, comprising administering the composition of claim 1 to a patient in need thereof, wherein the inhibition is mediated by inhibiting nucleolin through nucleolin binding.

* * * * *

SEQUENCE LISTING

<160> NUMBER OF SEQ ID NOS: 25

<210> SEQ ID NO 1
<211> LENGTH: 10
<212> TYPE: PRT
<213> ORGANISM: Artificial Sequence
<220> FEATURE:

```
<223> OTHER INFORMATION: Synthetic peptide

<400> SEQUENCE: 1

Lys Lys Lys Gly Pro Lys Glu Lys Gly Cys
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Lys Lys Lys Lys Gly Cys
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide

<400> SEQUENCE: 3

Lys Lys Lys Lys Gly Pro Lys Lys Lys Gly Ala
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: Xaa is (2S)-2-aminohexanamide

<400> SEQUENCE: 4

Lys Lys Lys Gly Pro Lys Glu Lys Xaa
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Lysinyl proline
<220> FEATURE:
<221> NAME/KEY: BINDING
<222> LOCATION: (3)..(3)
<223> OTHER INFORMATION: N6-Arg-Pro-Lysinyl
<220> FEATURE:
<221> NAME/KEY: BINDING
<222> LOCATION: (5)..(5)
<223> OTHER INFORMATION: N6-Arg-Pro-Lysinyl
<220> FEATURE:
<221> NAME/KEY: BINDING
<222> LOCATION: (8)..(8)
<223> OTHER INFORMATION: N6-Arg-Pro-Lysinyl
<220> FEATURE:
<221> NAME/KEY: BINDING
<222> LOCATION: (10)..(10)
<223> OTHER INFORMATION: N6-Arg-Pro-Lysinyl
<220> FEATURE:
<221> NAME/KEY: MOD_RES
```

```
<222> LOCATION: (11)..(11)
<223> OTHER INFORMATION: Xaa is (2S)-2-aminohexanamide

<400> SEQUENCE: 5

Pro Arg Lys Lys Lys Gly Pro Lys Glu Lys Xaa
1               5                   10

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Aib (2-aminoisobutyric acid)
<220> FEATURE:
<221> NAME/KEY: MOD_RES
<222> LOCATION: (3)..(3)
<223> OTHER INFORMATION: Aib (2-aminoisobutyric acid)

<400> SEQUENCE: 6

Xaa Lys Xaa Gly
1

<210> SEQ ID NO 7
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib (2-aminoisobutyric acid)

<400> SEQUENCE: 7

Lys Xaa Gly
1

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Aib (2-aminoisobutyric acid)
<220> FEATURE:
<221> NAME/KEY: MOD_RES
<222> LOCATION: (3)..(3)
<223> OTHER INFORMATION: Aib (2-aminoisobutyric acid)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: MOD_RES
<222> LOCATION: (7)..(7)
<223> OTHER INFORMATION: Aib (2-aminoisobutyric acid)
<220> FEATURE:
<221> NAME/KEY: MOD_RES
<222> LOCATION: (9)..(9)
<223> OTHER INFORMATION: Aib (2-aminoisobutyric acid)
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
```

-continued

<222> LOCATION: (13)..(13)
<223> OTHER INFORMATION: Aib (2-aminoisobutyric acid)
<220> FEATURE:
<221> NAME/KEY: MOD_RES
<222> LOCATION: (15)..(15)
<223> OTHER INFORMATION: Aib (2-aminoisobutyric acid)
<220> FEATURE:
<221> NAME/KEY: MOD_RES
<222> LOCATION: (17)..(17)
<223> OTHER INFORMATION: Aib (2-aminoisobutyric acid)
<220> FEATURE:
<221> NAME/KEY: MOD_RES
<222> LOCATION: (19)..(19)
<223> OTHER INFORMATION: Aib (2-aminoisobutyric acid)

<400> SEQUENCE: 8

Xaa Lys Xaa Gly Xaa Lys Xaa Gly Xaa Lys Xaa Gly Xaa Lys Xaa Gly
1               5                   10                  15

Xaa Lys Xaa Gly
            20

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib (2-aminoisobutyric acid)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (14)..(14)
<223> OTHER INFORMATION: Aib (2-aminoisobutyric acid)

<400> SEQUENCE: 9

Lys Xaa Gly Lys Xaa Gly Lys Xaa Gly Lys Xaa Gly Lys Xaa Gly
1               5                   10                  15

<210> SEQ ID NO 10
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Aib (2-aminoisobutyric acid)
<220> FEATURE:
<221> NAME/KEY: BINDING
<222> LOCATION: (2)..(2)
<223> OTHER INFORMATION: N6-Arg-Pro-Lysinyl
<220> FEATURE:
<221> NAME/KEY: MOD_RES
<222> LOCATION: (3)..(3)
<223> OTHER INFORMATION: Aib (2-aminoisobutyric acid)
<220> FEATURE:
<221> NAME/KEY: MOD_RES
<222> LOCATION: (5)..(5)
<223> OTHER INFORMATION: Aib (2-aminoisobutyric acid)

```
<220> FEATURE:
<221> NAME/KEY: BINDING
<222> LOCATION: (6)..(6)
<223> OTHER INFORMATION: N6-Arg-Pro-Lysinyl
<220> FEATURE:
<221> NAME/KEY: MOD_RES
<222> LOCATION: (7)..(7)
<223> OTHER INFORMATION: Aib (2-aminoisobutyric acid)
<220> FEATURE:
<221> NAME/KEY: MOD_RES
<222> LOCATION: (9)..(9)
<223> OTHER INFORMATION: Aib (2-aminoisobutyric acid)
<220> FEATURE:
<221> NAME/KEY: BINDING
<222> LOCATION: (10)..(10)
<223> OTHER INFORMATION: N6-Arg-Pro-Lysinyl
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (13)..(13)
<223> OTHER INFORMATION: Aib (2-aminoisobutyric acid)
<220> FEATURE:
<221> NAME/KEY: BINDING
<222> LOCATION: (14)..(14)
<223> OTHER INFORMATION: N6-Arg-Pro-Lysinyl
<220> FEATURE:
<221> NAME/KEY: MOD_RES
<222> LOCATION: (15)..(15)
<223> OTHER INFORMATION: Aib (2-aminoisobutyric acid)
<220> FEATURE:
<221> NAME/KEY: MOD_RES
<222> LOCATION: (17)..(17)
<223> OTHER INFORMATION: Aib (2-aminoisobutyric acid)
<220> FEATURE:
<221> NAME/KEY: BINDING
<222> LOCATION: (18)..(18)
<223> OTHER INFORMATION: N6-Arg-Pro-Lysinyl
<220> FEATURE:
<221> NAME/KEY: MOD_RES
<222> LOCATION: (19)..(19)
<223> OTHER INFORMATION: Aib (2-aminoisobutyric acid)

<400> SEQUENCE: 10

Xaa Lys Xaa Gly Xaa Lys Xaa Gly Xaa Lys Xaa Gly Xaa Lys Xaa Gly
1               5                   10                  15

Xaa Lys Xaa Gly
            20

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: N6-Arg-Pro-Lysinyl
<220> FEATURE:
<221> NAME/KEY: MOD_RES
<222> LOCATION: (2)..(2)
<223> OTHER INFORMATION: Aib (2-aminoisobutyric acid)
<220> FEATURE:
<221> NAME/KEY: BINDING
<222> LOCATION: (4)..(4)
<223> OTHER INFORMATION: N6-Arg-Pro-Lysinyl
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: BINDING
<222> LOCATION: (7)..(7)
```

```
<223> OTHER INFORMATION: N6-Arg-Pro-Lysinyl
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: BINDING
<222> LOCATION: (10)..(10)
<223> OTHER INFORMATION: N6-Arg-Pro-Lysinyl
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: BINDING
<222> LOCATION: (13)..(13)
<223> OTHER INFORMATION: N6-Arg-Pro-Lysinyl
<220> FEATURE:
<221> NAME/KEY: MOD_RES
<222> LOCATION: (14)..(14)
<223> OTHER INFORMATION: Aib (2-aminoisobutyric acid)

<400> SEQUENCE: 11

Lys Xaa Gly Lys Xaa Gly Lys Xaa Gly Lys Xaa Gly Lys Xaa Gly
1               5                   10                  15

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide

<400> SEQUENCE: 12

Lys Ala Lys Pro Gly
1               5

<210> SEQ ID NO 13
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl lysine
<220> FEATURE:
<221> NAME/KEY: MOD_RES
<222> LOCATION: (15)..(15)
<223> OTHER INFORMATION: Amide glycine

<400> SEQUENCE: 13

Lys Ala Lys Pro Gly Lys Ala Lys Pro Gly Lys Ala Lys Pro Gly
1               5                   10                  15

<210> SEQ ID NO 14
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Aib (2-aminoisobutyric acid)
<220> FEATURE:
<221> NAME/KEY: MOD_RES
<222> LOCATION: (1)..(1)
<223> OTHER INFORMATION: Acetyl lysine
<220> FEATURE:
<221> NAME/KEY: MOD_RES
<222> LOCATION: (3)..(3)
```

```
<223> OTHER INFORMATION: Aib (2-aminoisobutyric acid)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: MOD_RES
<222> LOCATION: (7)..(7)
<223> OTHER INFORMATION: Aib (2-aminoisobutyric acid)
<220> FEATURE:
<221> NAME/KEY: MOD_RES
<222> LOCATION: (9)..(9)
<223> OTHER INFORMATION: Aib (2-aminoisobutyric acid)
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (13)..(13)
<223> OTHER INFORMATION: Aib (2-aminoisobutyric acid)
<220> FEATURE:
<221> NAME/KEY: MOD_RES
<222> LOCATION: (15)..(15)
<223> OTHER INFORMATION: Aib (2-aminoisobutyric acid)
<220> FEATURE:
<221> NAME/KEY: MOD_RES
<222> LOCATION: (17)..(17)
<223> OTHER INFORMATION: Aib (2-aminoisobutyric acid)
<220> FEATURE:
<221> NAME/KEY: MOD_RES
<222> LOCATION: (19)..(19)
<223> OTHER INFORMATION: Aib (2-aminoisobutyric acid)
<220> FEATURE:
<221> NAME/KEY: MOD_RES
<222> LOCATION: (21)..(21)
<223> OTHER INFORMATION: Aib (2-aminoisobutyric acid)
<220> FEATURE:
<221> NAME/KEY: MOD_RES
<222> LOCATION: (23)..(23)
<223> OTHER INFORMATION: Aib (2-aminoisobutyric acid)
<220> FEATURE:
<221> NAME/KEY: MOD_RES
<222> LOCATION: (24)..(24)
<223> OTHER INFORMATION: Amide glycine

<400> SEQUENCE: 14

Xaa Lys Xaa Gly Xaa Lys Xaa Gly Xaa Lys Xaa Gly Xaa Lys Xaa Gly
1               5                   10                  15

Xaa Lys Xaa Gly Xaa Lys Xaa Gly
            20

<210> SEQ ID NO 15
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl lysine
<220> FEATURE:
<221> NAME/KEY: MOD_RES
<222> LOCATION: (2)..(2)
<223> OTHER INFORMATION: Aib (2-aminoisobutyric acid)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: MOD_RES
```

```
<222> LOCATION: (11)..(11)
<223> OTHER INFORMATION: Aib (2-aminoisobutyric acid)
<220> FEATURE:
<221> NAME/KEY: MOD_RES
<222> LOCATION: (14)..(14)
<223> OTHER INFORMATION: Aib (2-aminoisobutyric acid)
<220> FEATURE:
<221> NAME/KEY: MOD_RES
<222> LOCATION: (17)..(17)
<223> OTHER INFORMATION: Aib (2-aminoisobutyric acid)
<220> FEATURE:
<221> NAME/KEY: MOD_RES
<222> LOCATION: (18)..(18)
<223> OTHER INFORMATION: Amide glycine

<400> SEQUENCE: 15

Lys Xaa Gly Lys Xaa Gly Lys Xaa Gly Lys Xaa Gly Lys Xaa Gly Lys
1               5                   10                  15

Xaa Gly

<210> SEQ ID NO 16
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl lysine
<220> FEATURE:
<221> NAME/KEY: BINDING
<222> LOCATION: (1)..(1)
<223> OTHER INFORMATION: N6-Arg-Pro-Lysinyl
<220> FEATURE:
<221> NAME/KEY: MOD_RES
<222> LOCATION: (2)..(2)
<223> OTHER INFORMATION: Aib (2-aminoisobutyric acid)
<220> FEATURE:
<221> NAME/KEY: BINDING
<222> LOCATION: (4)..(4)
<223> OTHER INFORMATION: LYS-X-PRO-ARG-LYS. X is the (-CH2NH-) binding
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: BINDING
<222> LOCATION: (7)..(7)
<223> OTHER INFORMATION: N6-Arg-Pro-Lysinyl
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: BINDING
<222> LOCATION: (10)..(10)
<223> OTHER INFORMATION: N6-Arg-Pro-Lysinyl
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: BINDING
<222> LOCATION: (13)..(13)
<223> OTHER INFORMATION: N6-Arg-Pro-Lysinyl
<220> FEATURE:
<221> NAME/KEY: MOD_RES
<222> LOCATION: (14)..(14)
<223> OTHER INFORMATION: Aib (2-aminoisobutyric acid)
<220> FEATURE:
<221> NAME/KEY: BINDING
<222> LOCATION: (16)..(16)
<223> OTHER INFORMATION: N6-Arg-Pro-Lysinyl
<220> FEATURE:
<221> NAME/KEY: MOD_RES
```

```
<222> LOCATION: (17)..(17)
<223> OTHER INFORMATION: Aib (2-aminoisobutyric acid)
<220> FEATURE:
<221> NAME/KEY: MOD_RES
<222> LOCATION: (18)..(18)
<223> OTHER INFORMATION: Amide glycine

<400> SEQUENCE: 16

Lys Xaa Gly Lys Xaa Gly Lys Xaa Gly Lys Xaa Gly Lys Xaa Gly Lys
1               5                   10                  15

Xaa Gly

<210> SEQ ID NO 17
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl lysine
<220> FEATURE:
<221> NAME/KEY: BINDING
<222> LOCATION: (1)..(1)
<223> OTHER INFORMATION: N6-Arg-Pro-Lysinyl
<220> FEATURE:
<221> NAME/KEY: BINDING
<222> LOCATION: (3)..(3)
<223> OTHER INFORMATION: N6-Arg-Pro-Lysinyl
<220> FEATURE:
<221> NAME/KEY: BINDING
<222> LOCATION: (6)..(6)
<223> OTHER INFORMATION: N6-Arg-Pro-Lysinyl
<220> FEATURE:
<221> NAME/KEY: BINDING
<222> LOCATION: (8)..(8)
<223> OTHER INFORMATION: N6-Arg-Pro-Lysinyl
<220> FEATURE:
<221> NAME/KEY: BINDING
<222> LOCATION: (11)..(11)
<223> OTHER INFORMATION: N6-Arg-Pro-Lysinyl
<220> FEATURE:
<221> NAME/KEY: BINDING
<222> LOCATION: (13)..(13)
<223> OTHER INFORMATION: N6-Arg-Pro-Lysinyl
<220> FEATURE:
<221> NAME/KEY: MOD_RES
<222> LOCATION: (15)..(15)
<223> OTHER INFORMATION: Amide glycine

<400> SEQUENCE: 17

Lys Ala Lys Pro Gly Lys Ala Lys Pro Gly Lys Ala Lys Pro Gly
1               5                   10                  15

<210> SEQ ID NO 18
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Aib (2-aminoisobutyric acid)
<220> FEATURE:
<221> NAME/KEY: MOD_RES
<222> LOCATION: (1)..(1)
<223> OTHER INFORMATION: Acetyl lysine
<220> FEATURE:
<221> NAME/KEY: MOD_RES
<222> LOCATION: (3)..(3)
<223> OTHER INFORMATION: Aib (2-aminoisobutyric acid)
<220> FEATURE:
```

```
<221> NAME/KEY: MOD_RES
<222> LOCATION: (5)..(5)
<223> OTHER INFORMATION: Aib (2-aminoisobutyric acid)
<220> FEATURE:
<221> NAME/KEY: MOD_RES
<222> LOCATION: (7)..(7)
<223> OTHER INFORMATION: Aib (2-aminoisobutyric acid)
<220> FEATURE:
<221> NAME/KEY: MOD_RES
<222> LOCATION: (9)..(9)
<223> OTHER INFORMATION: Aib (2-aminoisobutyric acid)
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (13)..(13)
<223> OTHER INFORMATION: Aib (2-aminoisobutyric acid)
<220> FEATURE:
<221> NAME/KEY: MOD_RES
<222> LOCATION: (15)..(15)
<223> OTHER INFORMATION: Aib (2-aminoisobutyric acid)
<220> FEATURE:
<221> NAME/KEY: MOD_RES
<222> LOCATION: (17)..(17)
<223> OTHER INFORMATION: Aib (2-aminoisobutyric acid)
<220> FEATURE:
<221> NAME/KEY: MOD_RES
<222> LOCATION: (19)..(19)
<223> OTHER INFORMATION: Aib (2-aminoisobutyric acid)
<220> FEATURE:
<221> NAME/KEY: MOD_RES
<222> LOCATION: (20)..(20)
<223> OTHER INFORMATION: Amide glycine

<400> SEQUENCE: 18

Xaa Lys Xaa Gly Xaa Lys Xaa Gly Xaa Lys Xaa Gly Xaa Lys Xaa Gly
1               5                   10                  15

Xaa Lys Xaa Gly
            20

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl lysine
<220> FEATURE:
<221> NAME/KEY: MOD_RES
<222> LOCATION: (2)..(2)
<223> OTHER INFORMATION: Aib (2-aminoisobutyric acid)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (14)..(14)
<223> OTHER INFORMATION: Aib (2-aminoisobutyric acid)
<220> FEATURE:
<221> NAME/KEY: MOD_RES
<222> LOCATION: (15)..(15)
<223> OTHER INFORMATION: Amide glycine
```

-continued

```
<400> SEQUENCE: 19

Lys Xaa Gly Lys Xaa Gly Lys Xaa Gly Lys Xaa Gly Lys Xaa Gly
1               5                   10                  15

<210> SEQ ID NO 20
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Aib (2-aminoisobutyric acid)
<220> FEATURE:
<221> NAME/KEY: MOD_RES
<222> LOCATION: (1)..(1)
<223> OTHER INFORMATION: Acetyl lysine
<220> FEATURE:
<221> NAME/KEY: BINDING
<222> LOCATION: (2)..(2)
<223> OTHER INFORMATION: N6-Arg-Pro-Lysinyl
<220> FEATURE:
<221> NAME/KEY: MOD_RES
<222> LOCATION: (3)..(3)
<223> OTHER INFORMATION: Aib (2-aminoisobutyric acid)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: BINDING
<222> LOCATION: (6)..(6)
<223> OTHER INFORMATION: N6-Arg-Pro-Lysinyl
<220> FEATURE:
<221> NAME/KEY: MOD_RES
<222> LOCATION: (7)..(7)
<223> OTHER INFORMATION: Aib (2-aminoisobutyric acid)
<220> FEATURE:
<221> NAME/KEY: MOD_RES
<222> LOCATION: (9)..(9)
<223> OTHER INFORMATION: Aib (2-aminoisobutyric acid)
<220> FEATURE:
<221> NAME/KEY: BINDING
<222> LOCATION: (10)..(10)
<223> OTHER INFORMATION: N6-Arg-Pro-Lysinyl
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (13)..(13)
<223> OTHER INFORMATION: Aib (2-aminoisobutyric acid)
<220> FEATURE:
<221> NAME/KEY: BINDING
<222> LOCATION: (14)..(14)
<223> OTHER INFORMATION: N6-Arg-Pro-Lysinyl
<220> FEATURE:
<221> NAME/KEY: MOD_RES
<222> LOCATION: (15)..(15)
<223> OTHER INFORMATION: Aib (2-aminoisobutyric acid)
<220> FEATURE:
<221> NAME/KEY: MOD_RES
<222> LOCATION: (17)..(17)
<223> OTHER INFORMATION: Aib (2-aminoisobutyric acid)
<220> FEATURE:
<221> NAME/KEY: BINDING
<222> LOCATION: (18)..(18)
<223> OTHER INFORMATION: N6-Arg-Pro-Lysinyl
<220> FEATURE:
<221> NAME/KEY: MOD_RES
<222> LOCATION: (19)..(19)
<223> OTHER INFORMATION: Aib (2-aminoisobutyric acid)
<220> FEATURE:
<221> NAME/KEY: MOD_RES
```

```
<222> LOCATION: (20)..(20)
<223> OTHER INFORMATION: Amide glycine

<400> SEQUENCE: 20

Xaa Lys Xaa Gly Xaa Lys Xaa Gly Xaa Lys Xaa Gly Xaa Lys Xaa Gly
1               5                   10                  15

Xaa Lys Xaa Gly
            20

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl lysine
<220> FEATURE:
<221> NAME/KEY: BINDING
<222> LOCATION: (1)..(1)
<223> OTHER INFORMATION: N6-Arg-Pro-Lysinyl
<220> FEATURE:
<221> NAME/KEY: MOD_RES
<222> LOCATION: (2)..(2)
<223> OTHER INFORMATION: Aib (2-aminoisobutyric acid)
<220> FEATURE:
<221> NAME/KEY: BINDING
<222> LOCATION: (4)..(4)
<223> OTHER INFORMATION: N6-Arg-Pro-Lysinyl
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: BINDING
<222> LOCATION: (7)..(7)
<223> OTHER INFORMATION: N6-Arg-Pro-Lysinyl
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: BINDING
<222> LOCATION: (10)..(10)
<223> OTHER INFORMATION: N6-Arg-Pro-Lysinyl
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: BINDING
<222> LOCATION: (13)..(13)
<223> OTHER INFORMATION: N6-Arg-Pro-Lysinyl
<220> FEATURE:
<221> NAME/KEY: MOD_RES
<222> LOCATION: (14)..(14)
<223> OTHER INFORMATION: Aib (2-aminoisobutyric acid)
<220> FEATURE:
<221> NAME/KEY: MOD_RES
<222> LOCATION: (15)..(15)
<223> OTHER INFORMATION: Amide glycine

<400> SEQUENCE: 21

Lys Xaa Gly Lys Xaa Gly Lys Xaa Gly Lys Xaa Gly Lys Xaa Gly
1               5                   10                  15

<210> SEQ ID NO 22
<211> LENGTH: 12
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MOD_RES
<222> LOCATION: (1)..(1)
<223> OTHER INFORMATION: Acetyl Lysine
<220> FEATURE:
<221> NAME/KEY: MOD_RES
<222> LOCATION: (2)..(2)
<223> OTHER INFORMATION: Aib (2-aminoisobutyric acid)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (12)..(12)
<223> OTHER INFORMATION: Amide glycine

<400> SEQUENCE: 22

Lys Xaa Gly Lys Xaa Gly Lys Xaa Gly Lys Xaa Gly
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl lysine
<220> FEATURE:
<221> NAME/KEY: BINDING
<222> LOCATION: (1)..(1)
<223> OTHER INFORMATION: N6-Arg-Pro-Lysinyl
<220> FEATURE:
<221> NAME/KEY: MOD_RES
<222> LOCATION: (2)..(2)
<223> OTHER INFORMATION: Aib (2-aminoisobutyric acid)
<220> FEATURE:
<221> NAME/KEY: BINDING
<222> LOCATION: (4)..(4)
<223> OTHER INFORMATION: N6-Arg-Pro-Lysinyl
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: BINDING
<222> LOCATION: (7)..(7)
<223> OTHER INFORMATION: N6-Arg-Pro-Lysinyl
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: BINDING
<222> LOCATION: (10)..(10)
<223> OTHER INFORMATION: N6-Arg-Pro-Lysinyl
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (12)..(12)
<223> OTHER INFORMATION: Amide glycine

<400> SEQUENCE: 23
```

```
Lys Xaa Gly Lys Xaa Gly Lys Xaa Gly Lys Xaa Gly
1               5                   10
```

<210> SEQ ID NO 24
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl Lysine
<220> FEATURE:
<221> NAME/KEY: MOD_RES
<222> LOCATION: (2)..(2)
<223> OTHER INFORMATION: Aib (2-aminoisobutyric acid)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (14)..(14)
<223> OTHER INFORMATION: Aib (2-aminoisobutyric acid)
<220> FEATURE:
<221> NAME/KEY: MOD_RES
<222> LOCATION: (17)..(17)
<223> OTHER INFORMATION: Aib (2-aminoisobutyric acid)
<220> FEATURE:
<221> NAME/KEY: MOD_RES
<222> LOCATION: (20)..(20)
<223> OTHER INFORMATION: Aib (2-aminoisobutyric acid)
<220> FEATURE:
<221> NAME/KEY: MOD_RES
<222> LOCATION: (23)..(23)
<223> OTHER INFORMATION: Aib (2-aminoisobutyric acid)
<220> FEATURE:
<221> NAME/KEY: MOD_RES
<222> LOCATION: (24)..(24)
<223> OTHER INFORMATION: Amide glycine

<400> SEQUENCE: 24

```
Lys Xaa Gly Lys Xaa Gly Lys Xaa Gly Lys Xaa Gly Lys Xaa Gly Lys
1               5                   10                  15
Xaa Gly Lys Xaa Gly Lys Xaa Gly
            20
```

<210> SEQ ID NO 25
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl lysine
<220> FEATURE:
<221> NAME/KEY: BINDING
<222> LOCATION: (1)..(1)
<223> OTHER INFORMATION: N6-Arg-Pro-Lysinyl
<220> FEATURE:
<221> NAME/KEY: MOD_RES
<222> LOCATION: (2)..(2)
<223> OTHER INFORMATION: Aib (2-aminoisobutyric acid)

```
<220> FEATURE:
<221> NAME/KEY: BINDING
<222> LOCATION: (4)..(4)
<223> OTHER INFORMATION: N6-Arg-Pro-Lysinyl
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: BINDING
<222> LOCATION: (7)..(7)
<223> OTHER INFORMATION: N6-Arg-Pro-Lysinyl
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: BINDING
<222> LOCATION: (10)..(10)
<223> OTHER INFORMATION: N6-Arg-Pro-Lysinyl
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: BINDING
<222> LOCATION: (13)..(13)
<223> OTHER INFORMATION: N6-Arg-Pro-Lysinyl
<220> FEATURE:
<221> NAME/KEY: MOD_RES
<222> LOCATION: (14)..(14)
<223> OTHER INFORMATION: Aib (2-aminoisobutyric acid)
<220> FEATURE:
<221> NAME/KEY: BINDING
<222> LOCATION: (16)..(16)
<223> OTHER INFORMATION: N6-Arg-Pro-Lysinyl
<220> FEATURE:
<221> NAME/KEY: MOD_RES
<222> LOCATION: (17)..(17)
<223> OTHER INFORMATION: Aib (2-aminoisobutyric acid)
<220> FEATURE:
<221> NAME/KEY: BINDING
<222> LOCATION: (19)..(19)
<223> OTHER INFORMATION: N6-Arg-Pro-Lysinyl
<220> FEATURE:
<221> NAME/KEY: MOD_RES
<222> LOCATION: (20)..(20)
<223> OTHER INFORMATION: Aib (2-aminoisobutyric acid)
<220> FEATURE:
<221> NAME/KEY: BINDING
<222> LOCATION: (22)..(22)
<223> OTHER INFORMATION: N6-Arg-Pro-Lysinyl
<220> FEATURE:
<221> NAME/KEY: MOD_RES
<222> LOCATION: (23)..(23)
<223> OTHER INFORMATION: Aib (2-aminoisobutyric acid)
<220> FEATURE:
<221> NAME/KEY: MOD_RES
<222> LOCATION: (24)..(24)
<223> OTHER INFORMATION: Amide glycine

<400> SEQUENCE: 25

Lys Xaa Gly Lys Xaa Gly Lys Xaa Gly Lys Xaa Gly Lys Xaa Gly Lys
1               5                   10                  15

Xaa Gly Lys Xaa Gly Lys Xaa Gly
            20
```